US008586719B2

(12) United States Patent
Chan et al.

(10) Patent No.: US 8,586,719 B2
(45) Date of Patent: Nov. 19, 2013

(54) TRITERPENES FOR MODULATING GENE EXPRESSION AND CELL MEMBRANE, AND AS ANTIPROTOZOAL AGENTS

(75) Inventors: Pui-Kwong Chan, Sugarland, TX (US); May Sung Mak, Hong Kong (CN)

(73) Assignee: Pacific Arrow Limited (CN)

( * ) Notice: Subject to any disclaimer, the term of this patent is extended or adjusted under 35 U.S.C. 154(b) by 341 days.

(21) Appl. No.: 12/856,322

(22) Filed: Aug. 13, 2010

(65) Prior Publication Data

US 2010/0317606 A1 Dec. 16, 2010

Related U.S. Application Data

(63) Continuation-in-part of application No. PCT/US2009/034115, filed on Feb. 13, 2009, and a continuation-in-part of application No. 12/344,682, filed on Dec. 29, 2008, and a continuation-in-part of application No. PCT/US2008/002086, filed on Feb. 15, 2008, which is a continuation-in-part of application No. PCT/US2007/077273, filed on Aug. 30, 2007, and a continuation-in-part of application No. 11/683,198, filed on Mar. 7, 2007, which is a continuation-in-part of application No. PCT/US2006/016158, filed on Apr. 27, 2006, and a continuation-in-part of application No. 11/289,142, filed on Nov. 28, 2005, now Pat. No. 7,488,753, and a continuation-in-part of application No. 11/267,523, filed on Nov. 4, 2005, now abandoned, and a continuation-in-part of application No. PCT/US2005/031900, filed on Sep. 7, 2005, and a continuation-in-part of application No. 11/131,551, filed on May 17, 2005, now Pat. No. 7,262,285, and a continuation-in-part of application No. 11/117,760, filed on Apr. 27, 2005, now Pat. No. 7,727,561, application No. 12/856,322, which is a continuation-in-part of application No. 12/392,795, filed on Feb. 25, 2009, now Pat. No. 8,334,269, and a continuation-in-part of application No. 12/541,713, filed on Aug. 14, 2009, and a continuation-in-part of application No. 12/714,598, filed on Mar. 1, 2010, and a continuation-in-part of application No. 12/195,112, filed on Aug. 20, 2008, now abandoned.

(60) Provisional application No. 61/038,277, filed on Mar. 20, 2008, provisional application No. 61/054,308, filed on May 19, 2008, provisional application No. 60/890,380, filed on Feb. 16, 2007, provisional application No. 60/947,705, filed on Jul. 3, 2007, provisional application No. 60/795,417, filed on Apr. 27, 2006, provisional application No. 60/841,727, filed on Sep. 1, 2006, provisional application No. 60/890,380, filed on Feb. 16, 2007, provisional application No. 60/675,282, filed on Apr. 27, 2005, provisional application No. 60/675,284, filed on Apr. 27, 2005.

(51) Int. Cl.
C07H 15/256 (2006.01)
C07C 35/44 (2006.01)

(52) U.S. Cl.
CPC .............. C07H 15/256 (2013.01); C07C 35/44 (2013.01)
USPC ......................................... 536/4.4; 536/18.1

(58) Field of Classification Search
None
See application file for complete search history.

(56) References Cited

U.S. PATENT DOCUMENTS

| | | | |
|---|---|---|---|
| 6,197,306 B1 | 3/2001 | Murali et al. | |
| 6,231,859 B1 | 5/2001 | Kensil | |
| 6,444,233 B1 | 9/2002 | Arntzen et al. | |
| 6,616,943 B2 | 9/2003 | Wang et al. | |
| 6,689,398 B2 | 2/2004 | Haridas et al. | |
| 6,746,696 B2 | 6/2004 | Arntzen et al. | |
| 6,872,713 B1* | 3/2005 | Maes et al. ................. | 514/169 |
| 6,962,720 B2 | 11/2005 | Haridas et al. | |
| 7,105,186 B2 | 9/2006 | Arntzen et al. | |

(Continued)

FOREIGN PATENT DOCUMENTS

| | | |
|---|---|---|
| AU | 2002348988 | 11/2007 |
| AU | 2004281707 | 9/2011 |

(Continued)

OTHER PUBLICATIONS

Germonprez et al., "New pentacyclic triterpene saponins with strong anti-leishmanial activity from the leaves of Maesa balansae" Tetrahedron (2004) vol. 60 pp. 219-228.*

(Continued)

Primary Examiner — Eric S Olson
(74) Attorney, Agent, or Firm — Law Offices of Albert Wai-Kit Chan, PLLC

(57) ABSTRACT

This invention provides methods, processes, compounds and compositions for modulating the gene expression or secretion of adhesion proteins, angiopoietins or their receptors to cure diseases, for anti-angiogenesis and for treating parasites, wherein the adhesion proteins or receptors comprise fibronectin, integrins family, myosin, vitronectin, collagen, laminin, glycosylation cell surface proteins, polyglycans, cadherin, heparin, tenascin, CD 54 , CAM, elastin and FAK; wherein the angiopoietins comprise angiopoietin 1, angiopoietin 2, angiopoietin 3, angiopoietin 4, angiopoietin 5, angiopoietin 6, angiopoietin 7, angiopoietin-like 1, angiopoietin-like 2, angiopoietin-like 3, angiopoietin-like 4, angiopoietin-like 5, angiopoietin-like 6, and angiopoietin-like 7; wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer, cervical cancer, esophageal cancer, testicular cancer, spleenic cancer, kidney cancer, lymphatic cancer, pancreas cancer, stomach cancer and thyroid cancer.

10 Claims, 3 Drawing Sheets

(56) References Cited

U.S. PATENT DOCUMENTS

Figure 1:
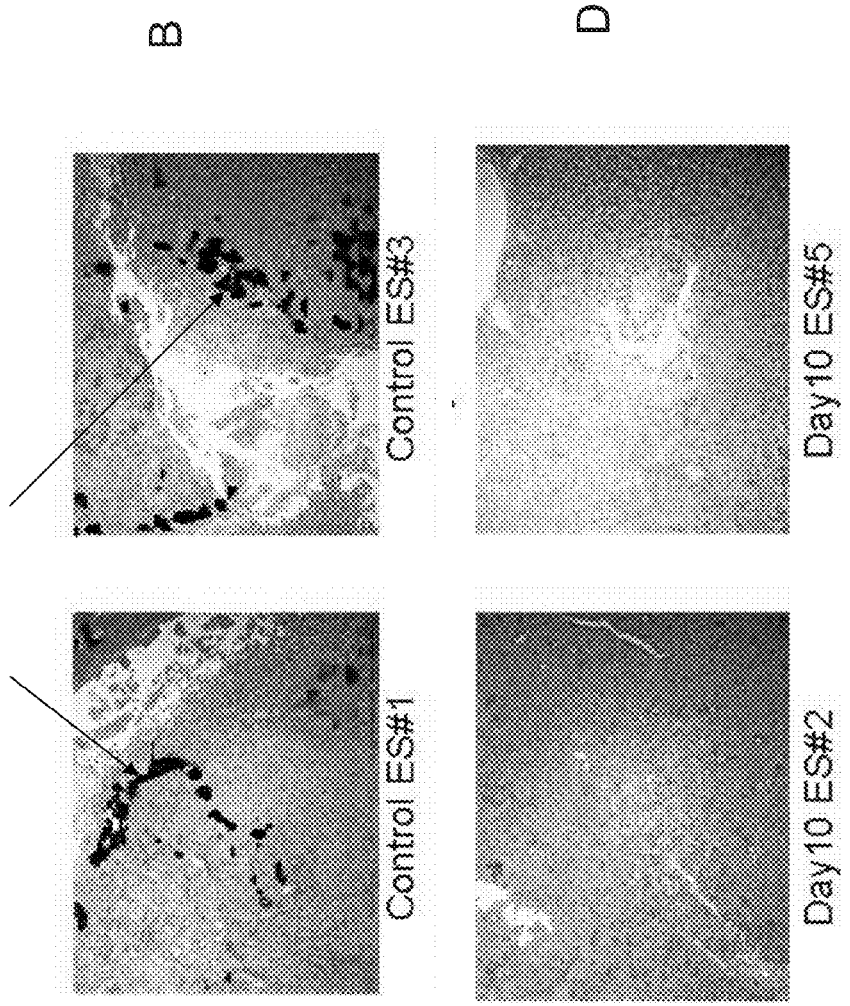

| | | |
|---|---|---|
| 7,262,285 B2 | 8/2007 | Chan et al. |
| 7,488,753 B2 | 2/2009 | Chan et al. |
| 7,514,412 B2 | 4/2009 | Chan et al. |
| 7,524,824 B2 | 4/2009 | Chan et al. |
| 7,670,632 B2 | 3/2010 | Arntzen et al. |
| 7,727,561 B2 | 6/2010 | Chan et al. |
| 7,780,974 B2 | 8/2010 | Gutterman et al. |
| 8,334,269 B2 | 12/2012 | Chan et al. |
| 2001/0053365 A1* | 12/2001 | Friede et al. ............... 424/187.1 |
| 2003/0082293 A1 | 5/2003 | Wang et al. |
| 2003/0096030 A1 | 5/2003 | Wang et al. |
| 2004/0138151 A1 | 7/2004 | Maes et al. |
| 2005/0209445 A1 | 9/2005 | Gokaraju et al. |
| 2005/0220910 A1 | 10/2005 | Chan et al. |
| 2005/0245470 A1 | 11/2005 | Chan et al. |
| 2005/0276872 A1 | 12/2005 | Chan et al. |
| 2005/0277601 A1 | 12/2005 | Chan et al. |
| 2006/0111310 A1 | 5/2006 | Chan et al. |
| 2006/0122129 A1 | 6/2006 | Chan et al. |
| 2006/0183687 A1 | 8/2006 | Cory |
| 2006/0263458 A1 | 11/2006 | Mak et al. |
| 2007/0161580 A1 | 7/2007 | Chan et al. |
| 2007/0196517 A1 | 8/2007 | San Martin |
| 2007/0212329 A1 | 9/2007 | Bruck et al. |
| 2007/0243269 A1 | 10/2007 | McNeff et al. |
| 2007/0245470 A1 | 10/2007 | Nguyen et al. |
| 2007/0249711 A1 | 10/2007 | Choi et al. |
| 2007/0254847 A1 | 11/2007 | Liu et al. |
| 2008/0058273 A1 | 3/2008 | Yang et al. |
| 2008/0064762 A1 | 3/2008 | Fuchs et al. |
| 2008/0096938 A1 | 4/2008 | Evindar et al. |
| 2008/0112925 A1 | 5/2008 | Hancock |
| 2008/0119420 A1 | 5/2008 | Liu et al. |
| 2009/0041877 A1 | 2/2009 | Mak et al. |
| 2009/0156515 A1 | 6/2009 | Chan et al. |
| 2010/0004190 A1 | 1/2010 | Chan et al. |
| 2010/0204169 A1* | 8/2010 | Chan et al. ..................... 514/33 |

FOREIGN PATENT DOCUMENTS

| | | |
|---|---|---|
| AU | 2009200988 | 3/2013 |
| CA | 2451740 | 12/2003 |
| CA | 2541425 | 1/2013 |
| CN | 93111010.6 | 5/1994 |
| CN | 1092991 A | 10/1994 |
| CN | 1092992 A | 10/1994 |
| CN | 1236792 C | 1/2006 |
| EP | 1463412 | 10/2004 |
| HK | 05102536.2 | 3/2005 |
| JP | 61-007285 | 1/1986 |
| JP | 61-130232 | 6/1986 |
| JP | 02-247196 | 10/1990 |
| JP | 2002-515430 A | 5/2002 |
| JP | 2005-500395 | 1/2005 |
| JP | 2006-070018 | 3/2006 |
| JP | 4815558 | 9/2011 |
| JP | 4880479 | 2/2012 |
| JP | 5087400 | 9/2012 |
| KR | 10-2004-7002889 | 2/2004 |
| KR | 10-1135824 | 4/2012 |
| NZ | 530449 | 10/2007 |
| NZ | 130542 | 4/2010 |
| NZ | 546138 | 4/2010 |
| NZ | 554037 | 8/2011 |
| SG | 102310 | 3/2006 |
| SG | 120666 | 10/2008 |
| TW | 091119471 | 8/2002 |
| TW | 93140030 | 12/2004 |
| TW | 94130519 | 12/2005 |
| WO | 0038700 | 7/2000 |
| WO | WO 03/017919 | 3/2003 |
| WO | WO 2005/037200 | 4/2005 |
| WO | WO 2005/063273 | 7/2005 |
| WO | WO 2006/029221 | 3/2006 |
| WO | WO 2006/116656 | 11/2006 |
| WO | PCT/US2008/02086 | 2/2008 |
| WO | WO 2008/028060 | 3/2008 |
| WO | WO 2008/028060 A2 | 3/2008 |
| WO | 2011009032 | 1/2011 |

OTHER PUBLICATIONS

Maes et al., "Comparative Activities of the Triterpene Saponin Maesabalide III and Liposomal Amphotericin B (AmBisome) against *Leishmania donovani* in Hamsters" Antimicrobial Agents and Chemotherapy (2004) vol. 48 No. 6 pp. 2056-2060.*
Apers et al., "Antiviral, Haemolytic and Molluscicidal Activities of Triterpenoid Saponins from Maesa lanceolata: Establishment of Structure-Activity Relationships" Planta Medica (2001) vol. 67 pp. 528-532.*
U.S. Appl. No. 12/392,795, filed Mar. 20, 2009, Chan et al.
U.S. Office Action for Mak, et al., U.S. Appl. No. 11/412,659, filed Apr. 27, 2006, Dated Mar. 8, 2007.
U.S. Notice of Allowability for Chan, et al., U.S. Appl. No. 11/131,551, filed May 17, 2005, Dated May 11, 2007.
U.S. Office Action for Chan, et al., U.S. Appl. No. 10/906,303, filed Feb. 14, 2005, Dated Feb. 12, 2007.
U.S. Office Action for Chan, et al., U.S. Appl. No. 11/117,745, filed Apr. 27, 2005, Dated Mar. 12, 2007.
U.S. Office Action for Chan, et al., U.S. Appl. No. 11/117,760, filed Apr. 27, 2005, Dated Jun. 29, 2007.
U.S. Office Action for Chan, et al., U.S. Appl. No. 11/117,760, filed Apr. 27, 2005, Dated Aug. 20, 2007.
U.S. Office Communication for Chan, et al., U.S. Appl. No. 11/117,760, filed Apr. 27, 2005, Dated Feb. 8, 2008.
U.S. Office Action for Chan, et al., U.S. Appl. No. 11/117,745, filed Apr. 27, 2005, Dated Aug. 22, 2007.
U.S. Final Office Action for Mak, et al., U.S. Appl. No. 11/412,659, filed Apr. 27, 2006, Dated Sep. 5, 2007.
U.S. Office Action for Chan, et al., U.S. Appl. No. 11/131,551, filed May 17, 2005, Dated Jan. 22, 2007.
U.S. 0ffice Action for Chan, et al., U.S. Appl. No. 11/289,142, filed Nov. 28, 2005, Dated Sep. 27, 2007.
U.S. Office Action for Chan, et al., U.S. Appl. No. 11/267,523, filed Nov. 4, 2005, Dated Sep. 27, 2007.
U.S. Office Action for Chan, et al., U.S. Appl. No. 11/117,745, filed Apr. 27, 2005, Dated Jan. 25, 2008.
U.S. Office Communication for Chan, et al., U.S. Appl. No. 10/906,303, filed Feb. 14, 2005, Dated Jan. 4, 2008.
U.S. Office Action for Mak, et al., U.S. Appl. No. 11/412,659, filed Apr. 27, 2006, Dated Feb. 20, 2008.
U.S. Office Action for Chan, et al., U.S. Appl. No. 11/289,142, filed Nov. 28, 2005, Dated Apr. 14, 2008.
U.S. Office Action for Chan, et al., U.S. Appl. No. 10/906,303, filed Feb. 14, 2005, Dated Jul. 27, 2007.
U.S. Advisory Action for Chan, et al., U.S. Appl. No. 11/289,142, filed Nov. 28, 2005, Dated Jul. 28, 2008.
U.S. Office Action for Chan, et al., U.S. Appl. No. 11/117,760, filed Apr. 27, 2005, Dated Mar. 18, 2009.
U.S. Office Action for Chan, et al., U.S. Appl. No. 11/683,198, filed Mar. 7, 2007, Dated May 1, 2009.
U.S.Office Action for Mak, et al., U.S. Appl. No. 12/195,112, filed Aug. 20, 2008, Dated May 19, 2009.
U.S. Office Action for Chan, et al., U.S. Appl. No. 11/683,198, filed Mar. 7, 2007, Dated Feb. 18. 2010.
U.S. Office Action for Mak, et al., U.S. Appl. No. 12/195,112, filed Aug. 20, 2008, Dated Feb, 18, 2010.
U.S. Office Action for Chan, et al., U.S. Appl. No. 11/683,198, filed Mar. 7, 2007, Dated Sep. 10, 2008.
PCT Written Opinion of the International Searching Authority for PCT/US2004/033359, filed Oct. 8, 2004 for Pacific Arrow Limited et al., dated Apr. 12, 2005.
PCT International Search Report for PCT/US2004/033359, filed Oct. 8, 2004 for Pacific Arrow Limited et al., dated Apr. 12, 2005.
PCT Written Opinion of the International Searching Authority for PCT/US2004/043465, filed Dec. 23, 2004 for Pacific Arrow Limited et al., dated May 17, 2005.

(56) References Cited

OTHER PUBLICATIONS

PCT International Search Report for PCT/US2004/043465, filed Dec. 23, 2004 for Pacific Arrow Limited et al., dated May 17, 2005.
PCT International Search Report for Pacific Arrow Limited, et al., Int'l App'l No. PCT/US2005/031900, filed Sep. 7, 2005, Dated Feb. 6, 2007.
PCT Written Opinion of the International Searching Authority for Pacific Arrow Limited, et al., Int'l App'l No. PCT/US2005/031900, filed Sep. 7, 2005, Dated Feb. 6, 2007.
PCT International Preliminary Report on Patentability issued on Mar. 22, 2007 for Pacific Arrow Limited, et al., Int'l App'l No. PCT/US2005/031900.
PCT International Preliminary Report on Patentability for Pacific Arrow Limited et al., Int'l App'l No. PCT/US2004/033359, filed Oct. 8, 2004, Dated Apr. 11, 2006.
PCT International Search Report issued on Nov. 13, 2006 for Pacific Arrow Limited et al., International App'l No. PCT/US2006/016158.
PCT Written Opinion of the International Searching Authority issued on Nov. 13, 2006 for Pacific Arrow Limited et al., International App'l No. PCT/US2006/016158.
PCT International Preliminary Report on Patentability issued on Feb. 7, 2006 for Pacific Arrow Limited et al., Int'l App'l No. PCT/US2004/043465.
PCT International Preliminary Report on Patentability for Pacific Arrow Limited, et al., Int'l App'l No. PCT/US2006/016158, filed Apr. 27, 2006, Dated Oct. 30, 2007.
PCT International Search Report issued on Jul. 7, 2008 for Pacific Arrow Limited et al., Int'l App'l No. PCT/US2008/002086.
PCT Written Opinion of the International Searching Authority issued on Jul. 7, 2008 for Pacific Arrow Limited et al., Int'l App'l No. PCT/US2008/002086.
Notice of Acceptance for Wang, Yun, Australia Patent App'l No. 2002348988, filed Jan. 21, 2004, Dated Jul. 26, 2007.
Notice of Acceptance for Wang, Yun, New Zealand App'l No. 530449, filed Jan. 6, 2004, Dated Jun. 29, 2007.
Supplementary European Search Report for Wang, Yun, European App'l No. 02781502.6, filed Feb. 25, 2004, Dated Jul. 6, 2005.
European Office Communication for Wang, Yun, European App'l No. 02781502.6, filed Feb. 25, 2004, Dated Jul. 20, 2007.
European Office Communication for Wang, Yun, European App'l No. 02781502.6, filed Feb. 25, 2004, Dated Oct. 12, 2005.
New Zealand Examination Report for Wang, Yun, New Zealand App'l No. 530449, filed Jan. 6, 2004, Dated Feb. 15, 2006.
New Zealand Examination Report for Wang, Yun, New Zealand App'l No. 530449, filed Jan. 6, 2004, Dated Apr. 10, 2007.
Australian Letters Patent No. 2002348988, Nov. 8, 2007, Wang, Yun, "Composition comprising Wenguanguo Extracts, Methods for Preparing Same and Uses Thereof".
New Zealand Letters Patent No. 530449, Oct. 11, 2007, Wang, Yun, "Composition comprising Wenguanguo Extracts, Methods for Preparing Same and Uses Thereof".
Chinese Office Action for Wang, Yun, Chinese Publication No. CN 1236792C, filed Jan. 18, 2006, Dated Aug. 27, 2004.
Chinese Office Action for Wang, Yun, Chinese Publication No. CN 1236792C, filed Jan. 18, 2006, Dated May 27, 2005.
Taiwan Office Action for Wang, Yun, Taiwan Application No. 091119471, filed Aug. 28, 2002, Dated Sep. 14, 2004.
Taiwan Office Action for Wang, Yun, Taiwan Application No. 091119471, filed Aug. 28, 2002, Dated Apr. 26, 2005.
PCT International Search Report for Pacific Arrow Limited et al., International App'l No. PCT/US07/77273, filed Aug. 30, 2007, Dated Aug. 4, 2008.
PCT Written Opinion of the International Searching Authority for Pacific Arrow Limited et al., International App'l No. PCT/US07/77273, filed Aug. 30, 2007, Dated Aug. 4, 2008.
New Zealand Office Action, May 8, 2009, for New Zealand Application No. 554037, filed Sep. 7, 2005.
Japan Office Action for Japan Patent Application No. 2003-522442, Nov. 4, 2008, International No. PCT/IB02/04750, filed Aug. 28, 2002, Fountain Silver Limited, "Composition comprising Wenguanoguo Extracts, Methods for Perparing Same and Uses Thereof".
Korean Office Action for Korean Application No. 10-2004-7002889, Nov. 21, 2008, International Application No. PCT/IB02/04750, filed Aug. 28, 2002, Fountain Silver Limited, "Composition Comprising Weguanoguo Extracts, Methods for Preparing Same and Uses Thereof".
Canadian Office Action for Canadian Application No. 2,451,740, Nov. 7, 2008, Fountain Silver Limited, "Composition Comprising Wenguanoguo Extracts, Methods for Preparing Same and Uses Thereof".
New Zealand Office Action, Aug. 12, 2009, New Zealand Application No. 546138, filed Mar. 22, 2007.
New Zealand Office Action, Sep. 22, 2009, New Zealand Application No. 546138, filed Mar. 27, 2006.
Supplementary European Search Report issued on Oct. 13, 2009 for Pacific Arrow Limited et al., European Patent Application No. 04815530.3.
Supplementary European Search Report issued on Oct. 13, 2009 for Pacific Arrow Limited et al., European Patent Application No. 04809909.7.
PCT Written Opinion of the International Searching Authority, Jun. 2, 2009, International App'l No. PCT/US09/34115, filed Feb. 13, 2009.
PCT Written Opinion of the International Searching Authority, Aug. 4, 2008, International App'l No. PCT/US07/77273, filed Aug. 30, 2007.
Notice of Allowability for Chan et al., U.S. Appl. No. 10/906,303, filed Feb. 14, 2005, dated Nov. 26, 2008.
Notice of Allowability for Chan et al., U.S. Appl. No. 11/117,745, filed Apr. 27, 2005, dated Dec. 2, 2008.
Notice of Allowability for Chan et al., U.S. Appl. No. 11/289,142, filed Nov. 28, 2005, dated No. Oct. 1, 2008.
PCT Notification of Transmittal of the International Search Report and the Written Opinion of the International Searching Authority, or the Declaration for PCT/US09/34115, filed Feb. 13, 2009 for Pacific Arrow Limited et al., dated Jun. 2, 2009.
PCT International Preliminary Report on Patentability, Mar. 12, 2009, International App'l No. PCT/US2007/077273, filed Aug. 30, 2007.
PCT Notification of Transmittal of International Preliminary Examination Report for PCT/IB02/04750, filed Aug. 28, 2002 for Fountain Silver Limited et al., dated Jun. 3, 2003.
PCT International Search Report for PCT/US2009/034115, filed Feb. 13, 2009 for Pacific Arrow Limited et al., dated Jun. 2, 2009.
Supplementary European Search Report issued on Oct. 22, 2009 for Mak et al., European Patent Application No. 05810263.3, PCT/US2005031900.
Australian Office Action for Australian Patent No. 2004281707, Feb. 19, 2010, Pacific Arrow Limited.
European Office Communication for Pacific Arrow Limited, et al., European App'l No. EP 06751723.5-2123, Dated Jan. 15, 2010.
European Office Communication for Mak May Sung, at al., European App'l No. EP 0581026.3-2123, Dated Dec. 29, 2009.
China Office Action for Pacific Arrow Limited, et al., China App'l No. 2004800367617, Dated Jan. 15, 2010.
European Office Communication for Pacific Arrow Limited, et al., European App'l No. EP 04809909.7-2123, Dated Apr. 19, 2010.
European Office Communication for Pacific Arrow Limited, et al., European App'l No. EP 04815530.3-2123, Dated Apr. 19, 2010.
European Office Communication for Mak May Sung, et al., European App'l No. EP 05810263.3-2123, Dated Apr. 19, 2010.
European Office Communication for Pacific Arrow Limited, et al., European App'l No. EP 07841638.5-2123, Dated Apr. 19, 2010.
Chinese Office Action, Mar. 27, 2009 for Pacific Arrow Limited, Chinese application No. 2005800375247, filed Jul. 26, 2007.
Chinese Office Action, Apr. 21, 2010 for Pacific Arrow Limited, Chinese application No. 2005800375247, filed Jul. 26, 2007.
New Zealand Letters Patent No. 546138, Apr. 8, 2010, Pacific Arrow Limited, at al. "Composition Comprising *Xanthoceras sorbifofia* Extracts, Compounds Isolated From Same. Methods for Perparing Same and Uses Thereof".

(56) References Cited

OTHER PUBLICATIONS

Canadian Office Action for Canadian Application No. 2,451,740, May 26, 200, Fountain Silver Limited, "Composition Comprising Wenguanoguo Extracts, Methods for Perparing Same and Uses Thereof".

PCT Preliminary Report on Patentability for PCT/US2009/034115, filed Feb. 13, 2009 for Pacific Arrow Limited et al., dated Aug. 26, 2010.

PCT Written Opinion of the International Searching Authority for PCT/US09/34115, filed Feb. 13, 2009 for Pacific Arrow Limited et al., dated Jun. 2, 2009.

PCT Written Opinion of the International Searching Authority for PCT/US10/42220, filed Jul. 16, 2010 for Pacific Arrow Limited et al., dated Sep. 2, 2010.

PCT International Search Report for PCT/US10/42240, filed Jul. 16, 2010 for Pacific Arrow Limited et al., dated Sep. 2, 2010.

Arda, Nazly. "Saniculoside N from *Sanicula europaea L*." Journal of Natural Products (1997), 60(11), 1170-1173.

Azam, Amir. "A triterpenoidal sapogenin from the seeds of *Dodonaea viscosa* Linn." Indian Journal of Chemistry, Section B: Organic Chemistry Including Medicinal Chemistry (1993), 32B(4), 513-514.

Barre, Juanita T. "A bioactive triterpene from *Lantana camara*." Phytochemistry (1997), 45(2), 321-324.

Barua, Arun K. "Triterpenoids. XXIX. Structure of barringtogenol B—a new triterpenoid sapogenin from *Barringtonia acutengula*." Tetrahedron (1968), 24(3), 1113-17.

Beeby, Philip J. "Angeloyl chloride: synthesis and utilization in the partial synthesis of lantadene A (rehrnannic acid)." Tetrahedron Letters (1977), (38), 3379-82.

Brown, J. M. M. "The relation of chemical structure to the icterogenic and photosensitizing action of some naturally occurring and synthetic triterpene acids." South African Journal of Laboratory and Clinical Medicine (1963), 9 262-72.

Brown, J. M. M. "Biliary excretion in the rabbit. II. The relation between the chemical structure of certain natural or synthetic pentacyclic triterpenes and their icterogenic activity. 2. The substituents on carbon atoms 17, 29, 20, and 22" Proc. Roy. Soc. (London) Ser. B (1964), 160(979), 246-57.

Chen, Y J. "Studies on the constituents of *Xanthoceras sorbifolia* Bunge. (I)." Shoyakugaku Zasshi (1984), 38(2), 203-6.

Chen, Y J. "Studies on the constituents of *Xanthoceras sorbifolia* Bunge. II." Chemical & pharmaceutical bulletin (Sep. 1984), 32(9), 3378-83.

Chen, Y J. "Studies on the constituents of *Xanthoceras sorbifolia* Bunge. III." Chemical & Pharmaceutical Bulletin (1985), 33(1), 127-34.

Chen, et al. "Studies on the constituents of *Xanthoceras sorbifolia* Bunge. IV. Structures of the minor prosapogenins." Chemical & Pharmaceutical Bulletin (1985), 33(3), 1043-8.

Chen, et al. "Studies on the constituents of *Xanthoceras sorbifolia* Bunge. V. Major saponins from the fruits of *Xanthoceras sorbifolia* Bunge." Chemical & Pharmaceutical Bulletin (1985), 33(4), 1387-94.

Cheng, et al. "Two new sterols in husk of *Xanthoceras sorbifolia*." Zhongcaoyao (2001), 32(3), 199-201.

Chakravarty, et al. "Triterpenoid prosaponins from leaves of *Maesa chisia* var. angustifolia." Phytochemistry (1987), 26(8). 2346-9.

Cui, et al. "2D NMR structure determination of five flavonoids from the wood of *Xanthoceras sorbifolia* Bunge." Shenyang Yaoxueyuan Xuebac (1991), 8(1), 36-8, 57.

Cui, et al. "Blood-activating constituents of Wenguanmu (*Xanthoceras sorbifolia*)." Zhongcaoyao (1987), 18(7), 297-8, 296.

Cui, et al. "The application of the microcomputer in the study of Chinese herb and natural drugs, 1. The Basic program used for the design of liquid-liquid extraction and forecasting the results of extraction and separation." Shenyang Yaoxueyuan Xuebao (1986), 3(2), 79-64.

Eakins, et al, "The effect of three triterpene acids and sporidesmin on the enzyme activities of rat liver plasma membranes." Chemico-Biological Interactions (1978), 21(1), 117-24.

Eakins, et al. "Studies on bile secretion with the aid of the isolated perfused rat liver. II. The effect of two further pentacyclic triterpenes, asiatic acid and 22-angeloyloxyoleanolicacid." Chemico-Biological Interactions (1978), 21(1), 79-87.

Hart, et al. "New triterpenes of *Lantana camera*. A comparative study of the constituents of several taxa." Australian Journal of Chemistry (1976), 29(3), 655-71.

Hopkins, et al, "Eicosenoic acid and other fatty acids of Sapindaceae seed oils." Lipids (1967), 2(3). 258-60.

Hu, et al. "Preparation of high-heating value synthetic liquid fuels." Faming Zhuanli Shenqing Gongkai Shuomingshu (1999), 4 pp.

Hu, et al. "Preparation of liquid fuels having high caloric value." Faming Zhuanli Shenqing Gongkai Shuomingshu (1994), 5 pp.

Huang, et al. "Chemical constituents of Wenguanmu (*Xanthoceras sorbifolia*) (I)." Zhongcaoyao (1987), 18(5), 199-202.

Huang, et al. "Preliminary studies on absorption and accumulation of atmospheric lead and cadmium by woody plants." Linye Kexue (1982), 18(1), 93-7.

Kim, et al. "Fatty-acid composition of vegetable oils," Choson Minjujuui Inmin Konghwaguk Kwahagwon Tongbo (1985), (3), 43-6.

Koike, et al. "New Triterpenoid saponins from *Maese japonica*." Journal of Natural Products (1999), 62(2), 228-232.

Kuang, et al. "Anti-inflammatory effects of n-butanol extract of *Xanthoceras sorbifolia* Bunge." Shenyang Yaoke Daxue Xuebao (2001), 18(1), 53-56.

Li, et al. "Medicine for enhancing mental activity." Faming Zhuanli Shenqing Gongkai Shuomingshu (1994), 7 pp.

Li, et al. "*Xanthoceras sorbifolia* fruit extracts for enhancing mental activity." Faming Zhuanli Shenqing Gongkai Shuomingshu (1994), 6 pp.

Li, et al. "Identification of fatty acids in the kernel oil of *Xanthoceras sorbifolia* Bge. with GC-MS." Zhiwu Ziyuan Yu Huanjing (1993), 2(2), 28-32.

Li, et al. "Isolation and structural determination of triterpene alcohols and 4-methylsterols in unsaponifiable fraction of the oil from *Xanthoceras sorbifolia* Bge." Linye Kexue (1984), 20(4), 397-402.

Li, et al. "Eremophilenolides and other constituents from the roots of *Ligularia sagitta*." Planta Medica (2003), 69(4), 356-360.

Li, et al. "New guaianolides and xanthine oxidase inhibitory flavonols from *Ajania fruticulosa*." Journal of Natural Products (1999), 62(7), 1053-1055.

Liu, et al. "The components of *Cacalia tangutica*." Bulletin of the Korean Chemical Society (2004), 25(7), 1078-1080.

Ma, et al. "A novel protoilludane sesquiterpene from the wood of *Xanthoceras sorbifolia*." Chinese Chemical Letters (2004), 15(1), 65-67.

Ma, et al. "Screening of Chinese and Mongolian herbal drugs for anti-human immunodeficiency virus type 1 (HIV-1) activity." Phytotherapy Research (2002), 16(S1), 186-189.

Ma, et al. "Inhibitory effects on HIV-1 protease of constituents from the wood of *Xanthoceras sorbifolia*." Journal of natural products (Feb. 2000), 63(2), 238-42.

Mahato, at al. "New triterpenoids from *Lantana camera*: Isomerisation of the angeloyl moiety of lantadene a during catalytic hydrogenation." Journal of the Indian Chemical Society (1999), 76(11-12), 723-726.

Meng, et al. "Antifungal highly oxygenated guaianolides and other constituents from *Ajania fruticulosa*."Phytochemistry (2001), 58(7), 1141-1145.

Nakamura, et al. "Inhibitory effects of some traditional medicines on proliferation of HIV-1 and its protease." Yakugaku Zasshi (2004), 124(8), 519-529.

Nathaji, et al. "Molecular structure of lantadene-B&C. triterpenoids of *Lantana camara*, red variety: lantadene-B, 22•-angeloyloxy-3-oxoolean-12-en-28-oic acid; lantacene-C, 22•-(S)-2'-methyl butanoyloxy-3-oxoolean-12-en-28-cic acid." Journal of Crystaliographic and Spectroscopic Research (1993), 23(6), 469-72.

(56) References Cited

OTHER PUBLICATIONS

Plouvier, et al. "Fraxoside and coumarin heterosides occurring in various botanical groups." Comptes Rendus des Seances de l'Academie des Sciences, Serie D: Sciences Naturelles (1968), 267 (22), 1883-5.
Plouvier, et al. "Flavone heterosides: kaempferol 3-rhamnoglucoside, mynricitrin, linarin, and saponarin." Comptes Rendus des Seances de l'Academie des Sciences, Serie : Sciences Naturelles (1966), 262(12), 1368-71.
Plouvier, et al."Oil of the seeds of *Xanthoceras orbifolia* Bunge and of *Koelreuteria paniculata* Laxm." Compt. rend. (1946), 222 916-17.
Sakurai, et al. "Assamicin I and II, novel triterpenoid saponins with insulin-like activity from *Aesculus assamica* Griff." Bioorganic & Medicinal Chemistry Letters (2002), 12(5), 807-810.
Semikhov, et al. "Comparative study of the amino acid composition of the embryo in grasses (*Poeceae*) and other flowering plants." Botanicheskii Zhurrai (Sankt-Peterburg, Russian Federation) (1994). 79(3), 63-92.
Sharma, et al. "Molecular structure, polymorphism, and toxicity of iantadene A, the pentacyclic triterpenoid from the hepatotoxic plant *Lantana camera*." Journal of biochemical toxicology (1991 Spring). 6(1), 57-63.
Shang-Jiang, et al. "Constituents of Shashen (*Adenophora axilliflora*)." Planta Medica (1986), (4), 317-20.
Sindambiwe, et al. "Triterpenoid saponins from *Maesa lanceolata*." Phytochemistry (1996), 41(1), 269-77.
Singh, et al. "Biotransformation of lantadene A (22•-angeloyloxy-3-oxoolean-12-en-28-oic acid), the pentacyclic triterpenoid, by *Alcaligenes faecalis*." Biodegradation (1999), 10(5), 373-381.
Tian, et al. "Study on the vegetative storage proteins in temperate hardwoods of fifteen families." Xibei Zhiwu Xuebao (2000), 20(5), 835-841.
"Triterpenoids. XVI. The constitution of rehmannic acid." Journal of the Chemical Society, Abstracts (1954), 900-3.
Tuntiwachwuttikul, et al. "A triterpenold saponin from *Maesa ramentacea*." Phytochemistry (1997), 44(3), 491-495.
Voutquenne, et al. "Triterpenoid saponins and acylated prosapogenins from *Harpullia austro-caledonica*." Phytochemistry (2002), 59(8), 825-832.
Wang, et al. "Chemical constituents of the oil and kernels of *Xanthoceras sorbifolia* Bunge." Zhiwu Xuebao (1981), 23(4), 331-3.
Waechter, et al. "Antitubercular Activity of Triterpenoids from *Lippia turbinata*." Journal of Natural Products (2001), 64(1), 37-41.
Yan, et al. "Separation, identification and determination of the unsaponifiable matters in vegetable oils." Beijing Shifan Daxue Xuebao, Ziran Kexueban (1985), (1),53-8.
Yan, et al. "Isolation, content analysis and structural determination of sterols in unsaponifiable fraction of the oil from *Xanthoceras sorbifolia* Bge." Linye Kexue (1984), 20(4), 389-96.
Yang, et al. "Extraction of total saponin, fat, protein, and saccharide from *Xanthoceras sorbifolia*." Faming Zhuanli Shenqing Gongkai Shuomingshu (2002), 4 pp.
Yang, et al. "Application of the extract of *Xanthoceras sorbifolia* shell in preparing the food and medicine for improving brain functions." Faming Zhuanli Shenqing Gongkai Shuomingshu (2002), 6 pp.
Yang, et al. "Two new triterpenoid saponins from the seeds of *Aesculus chinensis*." Chinese Chemical Letters (2000), 11(2), 139-142.
Zhang, et al. "Quantitative determination of myricetin and quercetin in *Xanthoceras sorbifolia* Bunge by HPLC." Shenyang Yaoke Daxue Xuebao (2000), 17(3), 194-196.
Zhang, et al. "Studies on chemical constituents of *Xanthoceras sorbifolia* Bunge." Yaoxue Xuebao (2000), 35(2), 124-127.
Zhao, et al. "Four new triterpene saponins from the seeds of *Aesculus chinensis*." Journal of Asian Natural Products Research (2003), 5(3), 197-203.
Zhao, et al. "Three new triterpene saponins from the seeds of *Aesculus chinensis*." Chemical & Pharmaceutical Bulletin (2001), 49(5), 626-628.
Zeng, et al. "Triterpenoids from *Mosla chinensis*." Indian Journal of Chemistry, Section B: Organic Chemistry Including Medicinal Chemistry (2000), 39B(11), 875-878.
Aper et al. "New acylated triterpenoid saponins from *Maese lanceolata*." Phytochemistry 52 (1999) 1121-1131.
D'Acquarica et al. "Isolation and structure elucidation of four new triterpenoid estersaponins from fruits of *Pittosporum tobira* AIT." Tetrahedron 58 (2002) 10127-10136.
Jiang et al. "Six Triterpenoid Saponins from *Maesa Laxiflora*." J. Nat. Prod. 1999. 62, 873-876.
Lu et al. "Triterpenoid saponins from the roots of tea plants (*Camellia sinensis* var. assamica)." Phytochemistry 53 (2000) 941-946.
Seo et al. "A New Triterpene Saponin from Pittosporum viridlflorum from the Madagascar Rainforest." J. Nat. Prod. 2002, 65. 65-6.
Yang et al. "Anti-HIV-1 Protease Triterpenoid Saponins from the Seeds of *Aesculus chinensis*." J. Nat. Prod. 1999, 62, 1510-1513.
Voutquenne et al. "Structure—Activity Relationships of Haemolytic Saponins" Pharmaceutical Biology (2002), vol. 40, No. 4, pp. 253-262.
Siroti, C., "Aescin: Pharmacology, Pharmacokinetic Profile" Pharmacological Research(2001) vol. 44, No. 3, pp. 183-193.
Oda, K. et al., "Adjuvant and Haemolytic Activities of 47 Saponins Derived from Medicinal and Food Plants" Biol. Chem. (2000) vol. 381, pp. 67-74.
Chan, Pui-Kwong, 2007, "Acylation with diangeloyl groups at C21-22 positions in triterpenoid saponins is essential for cytotoxcity towards tumor cells", Biochemical Pharmacology 73:(2007): 341-350.
Lavaud et al., 1992, "Saponins from *Steganotaenia Araliacea*", Phycochemistry, 31(9):3177-3181.
Li et al., 2005, "Two New Triterpenes from the Husks of *Xanthoceras Sorbifolia*", Planta Medica, 71: 1068-1070.
The Merck Manual of Diagnosis and Therapy, 17th Edition, 1999, Published by Merck Research Laboratories, pp. 397-398,948-949, 1916, and 1979-1981.
The Oxford Textbook of Oncology, 1995, Published by Oxford University Press, 447-453.
Zhang et al., 2007, "Cytotoxic triterpenoid saponins from the fruits of *Aesculus pavia* L", Phytochemistry 68(2007):2075-2086.
Voutquenne et al,, 2005, "Haemolytic Acylated Triterpenoid saponins from *Harpullia austro-caledonica*". Phytochemistry, vol. 66: 825-826.
Ma et al, 2008, "Cytotoxic Triterpenoid Saponins Acylated with Monoterpenic Acid from *Pithecellobium lucidum*",Journal of Natural Products, Vol, 71(1): 41-46.
Ushijima et al, 2008. "Triterpene Glycosides from the Roots of *Codonopsis lanceolal*", Chemical & Pharmaceutical Bulletin, vol. 56(3) 308-314.
Yadava et al., 2008, "New antibacterial triterpenoid saponin from *Lactuca scariola*", Fitoterapia, vol. 1:1-5.
Wang et al., 2008, "Bioactive Triterpene Saponins from the Roots of *Phytolacca Americana*", Journal of Natural Products, vol. 71(1): 35-40.
Chang et al, 2007, "Biologically Active Triterpenoid Saponins from *Ardisia japonica*", Journal of Natural Products, vol. 70(2): 179-187.
Akihisa et al, 2006, "Cancer Chemopreventive Effects and Cytotoxic Activities of the Triterpene Acids from the Resin of *Boswellia carteri*", Biological & Pharmaceutical Bulletin, vol. 29(9):1976-1979.
Liang, et al., 2006, "Triterpenoid Saponins from *Lysimachia davurica*", Chemical & Pharmaceutical Bulletin, vol. 54 (10):1380-1383.
Fujioka, et al., 2006, "Antiproliferative Constituents from *Umbelliferae* Plants. New Triterpenoid Glycosides from the Fruits of *Bupleurum rotundifolium*", Chemical & Pharmaceutical Bulletin, vol. 54 (12):1694-1704.
Rabi, et al., 2007, "Novel triterpencoid 25-hydroxy-3-oxoolean-12-en-28-oic acid induces growth arrest and apoptosis in breast cancer cells", Breast Cancer Research & Treatment, vol. 101:27-36.
Sporn, et al., 2007, "Platforms and Networks in Triterpenoid Pharmacology", Drug Development Research, vol. 68:174-182 (2007).

(56) References Cited

OTHER PUBLICATIONS

Puiffe, et al., 2007, "Characterization of Ovarian Cancer Ascites on Cell Invasion, Proliferation, Spheroid Formation, and Gene Expression in an In Vitro Model of Epithelial Ovarian Cancer" Neoplasia, vol. 9(10):820-829.
Ricciardelli, et al., 2006, "Extracellular Matrix of Ovarian Tumors". Seminars in Reproductive Medicine, vol. 24(4): 270-282.
Bang. et al., 2007, "Facile Synthesis of Trisaccharide Moiety Corresponding to Antitumor Activity in Triterpenoid Saponins Isolated from *Pullsatilla* Roots", Chemical & Pharmaceutical Bulletin, vol. 55(12): 1734-1739.
Talmadge, James E., 2008 "Follistatin as an Inhibitor of Experimental Metastasis", Clinical Cancer Research, vol. 14(3) 624-626.
Wei, et al., 2004, "Anti-inflammatory Triterpenoid Saponins from the Seeds of *Aesculus chinensis*", Chemical & Pharmaceutical Bulletin, vol. 52(10): 1246-1248.
Zhu et al, "Preliminary test of chemical constituents of wenguanguo and its multipurpose utilization". Reaearch of Land and natural Resources (1): 69-71, 1997 Arda, et al. "Saniculoside N from *Sanicula europaea*L." Journal of Natural Products (1997), 60(11), 1170-1173.
Maes, et al. "In vitro and in vivo activities of a triterpenoid saponin extract (px-6518) from the plant *Maesa balansae* against visceral *leishmania* species." Antimicrobial agents and chemotherapy, Jan. 2004, p. 130-136.
Murakami, et al. "New hypoglycemic constituents in "gymnemic acid" from gymnerna sylvestre." Chem. Pharm. Bull. 44(2) 469-471 (1996).
Na, et al. "Protein tyroshine phosphatase 1B inhibitory activity of triterpenes isolated from astilbe koreana." Bioorg Med Chem Lett. Jun. 15, 2006;16(12): 3273-6.
Zhou, et al. "The first naturally occurring tie2 kinase inhibitor." Org Lett. Dec. 13, 2001:3(25): 4047-9.
Konoshima, et al. "Antitumor Agents, 82. Cytotoxic Sapogenols from Aesculus Hippocastanum", Journal of Natural Products vol. 49, No. 4, pp. 650-656, Jul.-Aug. 1986.
2006 Chemical Abstracts Catalog, published 2006 by Chemical Abstracts Service, p. 52.
Apers Sandra et al., "Antiviral, haemolytic and molluscicidal activities of triterpenoid saponins from *Maesa lanceoiata*:Establishment of structure-activity relationships", Planta Medina, vol. 67, No. 6, Aug. 2001, pp. 528-532.
Ahmad V U et al., "The Sapogenins from Dodonaea-Viscosa", Fitoterapia, vol. 58, No. 5, 1987, pp. 361-362.
Dizes C et al., "Harpuloside a triterpenoid saponin *Harpullia ramiflora*", Phytochemistry, Pergamon Press, GB, vol. 48, No. 7, Aug. 1, 1998, pp. 1229-1232.
Cheng, et al. "Two new sterols in the husk of *Xanthoceras sorbifolia*." Chinese Traditional and Herbal Drugs (2001), 32(3), 199-201.
Cancer cell invasion and metastasis, King's college london, Strand, London WC2R 2Ls, UK, (2010).
U.S. Office Action, Jan. 19, 2011, for Chan et al., U.S. Appl. No. 12/344,682, filed Dec. 29, 2008.
U.S. Office Action, May 20, 2011, for Chan et al., U.S. Appl. No. 12/392,795, filed Feb. 25, 2009.
Notice of Allowability for Chan et al., U.S. Appl. No. 11/683,198, filed Mar. 7, 2007, Dated May 5, 2011.
US Office Action, May 12, 2011, for Chan et al., U.S. Appl. No. 12/714,598, filed Mar. 1, 2010.
U.S. Office Action, Oct. 27, 2011, for Chan et al., U.S. Appl. No. 12/344,682, filed Dec. 29, 2008.
PCT Written Opinion of the International Searching Authority, Dec. 6, 2011, for Pacific Arrow Limited, Int'l App'l No. PCT/US2011/044233, filed Jul. 15, 2011.
PCT International Search Report Dec. 6, 2011, for Pacific Arrow Limited, Int'l App'l No. PCT/US2011/044233, filed Jul. 15, 2011.
U.S. Office Action, Dec. 28, 2011, for Chan et al., U.S. Appl. No. 12/714,598, filed Mar. 1, 2010.
U.S. Notice of Allowance, Jan. 30, 2012, for Chan et al., U.S. Appl. No. 11/683,198, filed Mar. 7, 2007.
U.S. Office Action, Mar. 20, 2012, for Chan et al., U.S. Appl. No. 12/344,682, filed Dec. 29, 2008.
U.S. Office Action, Apr. 17, 2012, for Chan et al., U.S. Appl. No. 12/392,795, filed Feb. 25, 2009.
Notice of Allowability for Chan et al., U.S. Appl. No. 12/392,795, filed Feb. 25, 2009, Dated Aug. 15, 2012.
PCT Written Opinion of the International Searching Authority, Oct. 2, 2012, for Pacific Arrow Limited, Int'l App'l No. PCT/US12/46716, filed Jul. 13, 2012.
PCT International Search Report, Oct. 2, 2012, for Pacific Arrow Limited, Int'l App'l No. PCT/US12/46716, filed Jul. 13, 2012.
U.S. Office Action, Dec. 21, 2011, for Chan et al., U.S. Appl. No. 12/541,713, filed Aug. 14, 2009.
U.S. Office Action, Jun. 26, 2012, for Chan et al., U.S. Appl. No. 12/541,713, filed Aug. 14, 2009.
U.S. Office Action, Oct. 15, 2012, for Chan et al., U.S. Appl. No. 13/259,480, filed Sep. 23, 2011.
U.S. Office Action, Feb. 1, 2013, for Chan et al., U.S. Appl. No. 13/259,480, filed Sep. 23, 2011.
U.S. Office Action, Apr. 11, 2013, for Chan et al., U.S. Appl. No. 11/683,198, filed Mar. 7, 2007.
European Office Communication, Feb. 13, 2012, for Pacific Arrow Limited, European App'l No. EP 07841638.5-2123, filed Mar. 27, 2009.
European Office Communication, Feb. 13, 2012, for Pacific Arrow Limited, European App'l No. EP 05810263.3-2123, filed Mar. 30, 2007.
European Office Communication, Feb. 13, 2012, for Pacific Arrow Limited, European App'l No. EP 04815530.3-2123, filed Jul. 19, 2006.
European Office Communication, Mar. 5, 2012 for Pacific Arrow Limited, European App'l No. EP 04809909.7-2123, filed Mar. 27, 2006.
European Office Communication, Apr. 26, 2012 for Pacific Arrow Limited, European App'l No. EP 09721583.4-2123, filed Sep. 7, 2010.
European Office Communication, Jun. 4, 2012 for Pacific Arrow Limited, European App'l No. EP 02781502.6-2112, filed Feb. 25, 2004.
Australian Office Action, Mar. 18, 2011 for Pacific Arrow Limited, Australian Patent Application No. 2004281707, filed Oct. 8, 2004.
Notice of Acceptance for Pacific Arrow Limited, Australian Patent App'l No. 2004281707, filed Mar. 23, 2006, Dated May 26, 2011.
Australian Office Action, Feb. 6, 2012 for Pacific Arrow Limited, Australian App'l No. 2009208069, filed Aug. 7, 2009.
Australian Office Action, Feb. 6, 2012 for Pacific Arrow Limited, Australian App'l No. 2005282437, filed Mar. 19, 2007.
Australian Office Action, Feb. 6, 2012 for Pacific Arrow Limited, Australian App'l No. 2009200988, filed Mar. 10, 2009.
Australian Office Action, Jun. 21, 2012 for Pacific Arrow Limited, Australian App'l No. 2008244648, filed Aug. 21, 2009.
New Zealand Office Action, Mar. 7, 2011 for Pacific Arrow Limited, New Zealand App'l No. 587973, filed Sep. 14, 2010.
New Zealand Office Action, Mar. 28, 2011 for Pacific Arrow Limited, New Zealand App'l No. 554037, filed Mar. 19, 2007.
New Zealand Office Action, Sep. 24, 2010, for Pacific Arrow Limited, New Zealand App'l No. 579194, filed Aug. 21, 2009.
New Zealand Office Action, Jan. 11, 2012, for Pacific Arrow Limited, New Zealand App'l No. 579194, filed Aug. 21, 2009.
New Zealand Office Action, Mar. 26, 2012, for Pacific Arrow Limited, New Zealand App'l No. 598934, filed Mar. 21, 2012.
Japan Final Office Action, Feb. 23, 2009, for Fountain Silver Limited, Japan App'l No. 2003-522442, filed Feb. 5, 2004.
Japan Office Action, Jan. 14, 2011, for Pacific Arrow Limited, Japan App'l No. 2006-534419, filed Mar. 22, 2006.
Japan Office Action, Mar. 18, 2011, for Pacific Arrow Limited, Japan app'l No. 2006-547422, filed Jun. 16, 2006.
Japan Office Action, Jun. 3, 2011 for Pacific Arrow Limited, Japan App'l No. 2006-534419, filed Mar. 22, 2006.
Japanese Notice of Allowance, Nov. 15, 2011, for Pacific Arrow Limited, Japanese app'l No. 2006-547422, filed Jun. 16, 2006.
Japanese Office Action, Nov. 21, 2011, for Pacific Arrow Limited, Japanese app'l No. 2007-530484, filed Mar. 2, 2007.

(56) References Cited

OTHER PUBLICATIONS

Japanese Office Action, May 8, 2012, for Pacific Arrow Limited, Japanese app'l No. 2007-530484, filed Mar. 2, 2007.
Korean Office Action, Jun. 3, 2011 for Pacific Arrow Limited, Korean App'l No. 10-2006-7008896, filed May 8, 2006.
Korean Office Action, Jun. 22, 2012 for Pacific Arrow Limited, Korean App'l No. 10-2007-7007902, filed Apr. 6, 2007.
Canadian Office Action, Sep. 8, 2011, for Fountain Silver Limited et al., Canadian App'l No. 2,451,740, filed Dec. 18, 2003.
Canadian Notice of Allowance, Oct. 5, 2011, for Pacific Arrow Limited et al, Canadian App'l No. 2541425, filed Oct. 8, 2004.
Canadian Office Action, Jan. 31, 2012, for Pacific Arrow Limited, Canadian Application No. 2,579,231, filed Mar. 6, 2007.
Canadian Office Action, Jul. 5, 2012, for Fountain Silver Limited et al., Canadian App'l No. 2,451,740, filed Dec. 18, 2003.
Canadian Office Action, May 21, 2013, for Fountain Silver Limited et al., Canadian App'l No. 2,451,740, filed Dec. 18, 2003.
Canadian Office Action, Feb. 26, 2013, for Pacific Arrow Limited, Canadian App'l No. 2,579,231, filed Mar. 6, 2007.
Taiwan Office Action, Mar. 3, 2011 for Pacific Arrow Limited, Taiwan App'l No. 093140030, filed Dec. 22, 2004.
Taiwan Office Action, Jan. 18, 2012 for Pacific Arrow Limited, Taiwan App'l No. 094130519, filed Sep. 6, 2005.
Chinese Office Action, Jun. 3, 2011 for Pacific Arrow Limited, Chinese application No. 200880012065.0, filed Oct. 14, 2009.
Chinese Office Action, Jun. 14, 2011, for Pacific Arrow Limited, Chinese App'l No. 200480036761.7, filed Jun. 8, 2006.
Chinese Office Action, Oct. 28, 2011, for Pacific Arrow Limited, Chinese App'l No. 200480038698.0, filed Jun. 23, 2006.
Chinese Office Action, Sep. 28, 2011, for Pacific Arrow Limited, Chinese App'l No. 200480036761.7, filed Jun. 8, 2006.
Chinese Office Action, Mar. 23, 2011, for Pacific Arrow Limited, Chinese App'l No. 200780040744.4, filed Apr. 30, 2009.
Chinese Notice of Allowance, Feb. 1, 2011, for Pacific Arrow Limited, Chinese app'l No. 200580037524.7, filed Apr. 30, 2007.
Chinese Office Action, Apr. 9, 2012, for Pacific Arrow Limited, Chinese App'l No. 200780040744.4, filed Apr. 30, 2009.
Yang et al. "The Influence of aquaporin-1 and microvessel density on ovarian carcinogenesis and ascites formation", International Journal of Gynecological Cancer, vol. 16, No. 51, Feb. 1, 2006, pp. 400-405.
Germonprez N. et al. "In vitro and in vivo anti-leishmanial activity of triterpenoid saponins isolated from *Maesa balansae* and some chemical derivatives", Journal of Medicinal Chemistry, vol. 48 No. 1 (Jan. 13, 2005), p. 32-37.
Chemical Abstracts Service, Columbus, Ohio, US, Germonprez N. et al., "Antileishmanial saponins from *Maesa*" Tap Chi Hoa Hoc, 41(spec.), 125-130, (2003).
Dan Peer, et al. "Nanocarriers as an emerging platform for cancer therapy." Nature Publishing Group (2007), 751-760.

* cited by examiner

TRITERPENES FOR MODULATING GENE EXPRESSION AND CELL MEMBRANE, AND AS ANTIPROTOZOAL AGENTS

This application is a Continuation-in-part of International App'l No. PCT/US2009/034115, filed Feb. 13, 2009, which claims benefit of U.S. Ser. No. 61/038,277 filed Mar. 20, 2008, U.S. Ser. No. 61/054,308, filed May 19, 2008, and is a Continuation-in-part of U.S. Ser. No. 12/344,682, filed Dec. 29, 2008 and International App'l No. PCT/US2008/002086, filed Feb. 15, 2008, which is a continuation-in-part of International App'l No. PCT/US2007/077273, filed Aug. 30, 2007, which claims benefit of U.S. Ser. No. 60/890,380, filed on Feb. 16, 2007, U.S. Ser. No. 60/947,705, filed on Jul. 3, 2007, and is a continuation-in-part of U.S. Ser. No. 11/683, 198, filed on Mar. 7, 2007, which claims benefit of U.S. Ser. Nos. 60/795,417, filed on Apr. 27, 2006, 60/841,727, filed on Sep. 1, 2006, 60/890,380, filed on Feb. 16, 2007, and is a continuation-in-part of International Application No. PCT/US2006/016158, filed Apr. 27, 2006, which claims benefit of U.S. Ser. Nos. 60/675,282, filed Apr. 27, 2005 and U.S. Ser. No. 60/675,284, filed Apr. 27, 2005 and is a continuation-in-part of the following applications (1) U.S. Ser. No. 11/289, 142, filed Nov. 28, 2005; (2) U.S. Ser. No. 11/267,523, filed Nov. 4, 2005; (3) International Application No. PCT/US05/31900, filed Sep. 7, 2005 (which claims the benefit of U.S. Ser. Nos. 60/617,379, filed Oct. 8, 2004, 60/613,811, filed Sep. 27, 2004, and 60/607,858, filed Sep. 7, 2004); (4) U.S. Ser. No. 11/131,551, filed May 17, 2005; and (5) U.S. Ser. No. 11/117,760, filed Apr. 27, 2005. This application is also a continuation-in-part of U.S. Ser. Nos. 12/192,112, filed Aug. 20, 2008, 12/392,795, filed Feb. 25, 2009, 12/541,713, filed Aug. 14, 2009, and 12/714,598, filed Mar. 1, 2010. The contents of these preceding applications are hereby incorporated in their entireties by reference into this application.

FIELD OF THE INVENTION

This invention provides methods and compositions for reducing the adhesion protein in cell and blocks the migration, metastasis of cancer cells or inhibits the growth of cancers or anti-angiogenesis; wherein the cancers comprise cancer of breast, leukocyte, liver, ovarian, bladder, prostate, skin, bone, brain, leukemia, lung, colon, CNS, melanoma, renal, cervix, esophagus, testis, spleen, kidney, lymph, pancreas, stomach and thyroid, wherein the adhesion proteins or receptors comprise fibronectin, integrins family, myosin, vitronectin, collagen, laminin, glycosylation cell surface proteins, polyglycans, cadherin, heparin, tenascin, CD 54, CAM, elastin and FAK.

BACKGROUND OF THE INVENTION

The composition from *Maesa balansae* for anti-leishmanial is a United Nation funding project. This invention provides methods for inhibiting cancer metastasis or growth, wherein the cancers comprise breast cancer, leukocytic cancer, liver cancer, ovarian cancer, bladder cancer, prostatic cancer, skin cancer, bone cancer, brain cancer, leukemia cancer, lung cancer, colon cancer, CNS cancer, melanoma cancer, renal cancer, cervical cancer, esophageal cancer, testicular cancer, spleenic cancer, kidney cancer, lymphatic cancer, pancreatic cancer, stomach cancer and thyroid cancer., wherein the method is using the extract, composition and compounds from *Maesa balansae, Barringtonia acutangula, Xanthoceras Sorbifolia, Harpullia, Aesculus hippocastanum*.

SUMMARY OF THE INVENTION

This invention provides methods of using the extract, composition and compounds from *Maesa balansae* and *Barringtonia acutangula, Xanthoceras Sorbifolia, Harpullia, Aesculus hippocastanum* for reducing expression or secretion of adhesion proteins, for inhibiting cancer metastasis, wherein the cancers comprise cancers of breast, leukocyte, liver, ovarian, bladder, prostate, skin, bone, brain, leukemia, lung, colon, CNS, melanoma, renal, cervix, esophagus, testis, spleen, kidney, lymph, pancreas, stomach and thyroid.

This invention provides a method for modulating the adhesion of cancer cells and blocking their migration, metastasis or inhibiting the growth of cancers or anti-angiogenesis, wherein the adhesion proteins and their receptors comprise fibronectin, integrins family, myosin, vitronectin, collagen, laminin, glycosylation cell surface proteins, polyglycans, cadherin, heparin, tenascin, CD 54, CAM, elastin and FAK.

This invention provides a method of treating protozoal infections including leishmaniases, amoebiasis, trypanosomiasis, toxoplasmosis and malaria infection.

DETAILED DESCRIPTION OF THE FIGURES

FIG. 1: Analysis of genesis of blood vessels in xenografted tumor treated with compound Y. Figures A and B show the tumor sections taken from mice without Xanifolia Y treatment. Figures C and B show the tumor sections taken from mice with Xanifolia Y treatment. More blood vessels were observed in the control Group 1 than those in the drug-treated Group 2

Figure 2:
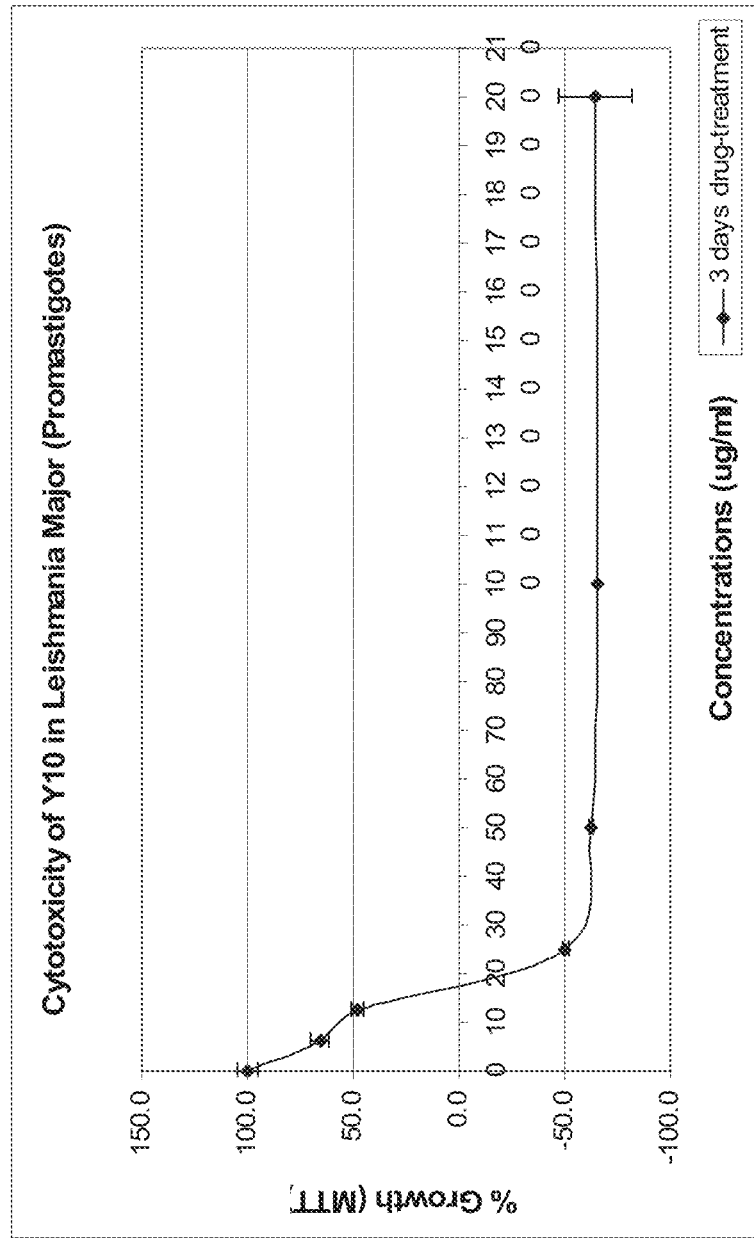

FIG. 2: Experiment shows that Y10 is cytotoxic to *Leishmania Major* (promastigotes) with IC50 approximately equal to 15 ug/ml.

Figure 3:
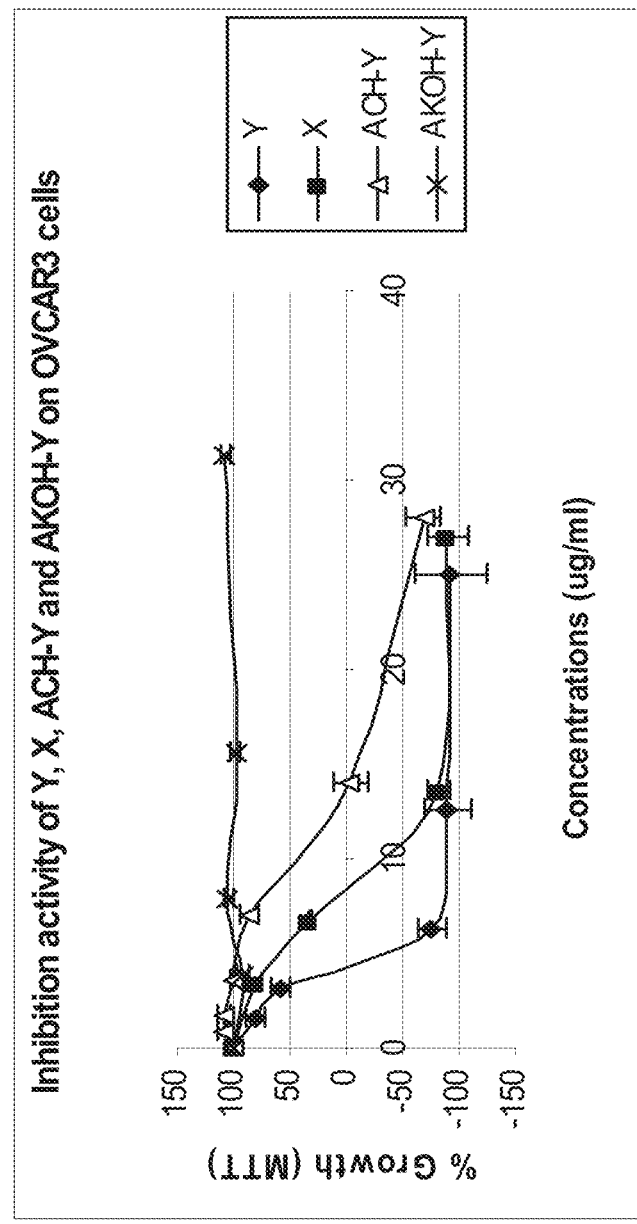

FIG. 3: Shows the inhibition activity of compound Y, X, ACH-Y and AKOH-Y.

DETAILED DESCRIPTION OF THE INVENTION

This invention provides methods and compositions for modulating gene expression to cure diseases or reduce the syndrome of diseases, wherein the modulating comprises positive and negative regulating. In an embodiment, the method comprises inhibiting gene expression. In an embodiment the method comprises stimulating gene expression.

This invention provides methods and compositions for inhibiting the migration, metastasis or growth of cancers or anti-angiogenesis, wherein the methods comprise affecting the gene expression, wherein the method comprises affecting adhesion proteins or their receptors, reducing adhesion proteins, or inhibiting the expression or secretion of adhesion proteins, wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK.

This invention provides methods and compositions for inhibiting the migration, metastasis or growth of cancers or anti-angiogenesis, wherein the methods comprise affecting the gene expression, wherein the method comprises stimulating gene expression.

This invention provides a method for altering the characteristics of cancer cell membranes resulting in blocking the migration, metastasis of cancer cells or inhibiting the growth of cancers or anti-angiogenesis, wherein the method comprises reducing adhesion proteins or their receptors, wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK.

This invention provides methods, processes, compounds and compositions of reducing expression or secretion of adhesion proteins of cells, wherein the adhesion proteins comprise fibronectin, integrins family, myosin, vitronectin, collagen, laminin, glycosylation cell surface proteins, polyglycans, cadherin, heparin, tenascin, CD54, CAM, elastin and FAK. In an embodiment, methods comprise inhibiting gene expression. In an embodiment, this invention provides a method of reducing the secretion of fibronectin. In an embodiment the method can block the migration, metastasis of cancer cells or inhibit the growth of cancers or anti-angiogenesis, wherein the cancers comprise breast, leukocyte, liver, ovarian, bladder, prostate, skin, bone, brain, leukemia, lung, colon, CNS, melanoma, renal, cervix, esophagus, testis, spleen, kidney, lymph, pancreas, stomach and thyroid cancer. In an embodiment, the method comprises contacting the cell with compound selected from Mb1, Mb2, Mb2.1, Mb3, Mb4, Mb5, Mb6, Mb7, Mb8, Mb9, Mb10, Mb11, Mb12 and Mb13, ACH-Z4, ACH-Y10, ACH-Y2, ACH-Y8, ACH-Y7, ACH-Y0, ACH-X, ACH-E, Ba1, Ba2, Ba3, Ba4, Ba5, Ba6, Ba7, Ba8, Ba9, Ba10, Ba11, Ba12, Ba13, Ba14, Ba15, Ba16, Ba17, Xanifolia Y0, Y1, Y2, Y, Y5, Y7, Y8, Y9, Y10, Xanifolia (x), Escin or Aescin or a salt, ester, metabolite thereof and Compound A to X and A1 to X1 in the application.

This invention provides a method of altering the characteristics of cancer cell membranes, wherein the method comprises altering the secretion of adhesion proteins, wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK. In an embodiment, the methods, processes, compounds and compositions comprise blocking, suppressing or inhibiting the expression or secretion of adhesion protein, wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK. In an embodiment, the methods, processes, compounds and compositions is interacting with adhesion proteins, wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK. In an embodiment the methods, processes, compounds or compositions can block the migration, metastasis of cancer cells or inhibit the growth of cancers or anti-angiogenesis, wherein the cancers comprise cancers of breast, leukocyte, liver, ovarian, bladder, prostate, skin, bone, brain, leukemia, lung, colon, CNS, melanoma, renal, cervix, esophagus, testis, spleen, kidney, lymph, pancreas, stomach and thyroid. In an embodiment, the method comprises contacting the cell with compound selected from Mb1, Mb2, Mb3, Mb4, Mb5, Mb6, Mb7, Mb8, Mb9, Mb10, Mb11, Mb12 and Mb13, ACH-Z4, ACH-Y10, ACH-Y2, ACH-Y8, ACH-Y7, ACH-Y0, ACH-X, ACH-E, Ba1, Ba2, Ba3, Ba4, Ba5, Ba6, Ba7, Ba8, Ba9, Ba10, Ba11, Ba12, Ba13, Ba14, Ba15, Ba16, Ba17, Xanifolia Y0, Y1, Y2, Y, Y7, Y8, Y9, Y10, Xanifolia (x), Escin or Aescin or a salt, ester, metabolite thereof and Compound A to X and A1 to X1 in the application.

The adhesion proteins help cancer cell adhesion, invasion or metastasis, wherein the cancers comprise ovarian cancer. Reducing the adhesion proteins will reduce the metastasis of cancers. Fibronectin is one of the key factors in the biology of epithelial ovarian cancers. Reduction of fibronectin will inhibit the metastasis of cancer cells.

This invention provides a method and composition for inhibiting the expression or secretion of adhesion proteins comprising fibronectin in order to cure diseases, wherein the diseases comprise inhibiting cancer growth, wherein the cancers comprise breast, leukocyte, liver, ovarian, bladder, prostate, skin, bone, brain, leukemia, lung, colon, CNS, melanoma, renal, cervix, esophagus, testis, spleen, kidney, lymph, pancreas, stomach and thyroid cancer. In an embodiment, the method comprises contacting the cell with compound selected from Mb1, Mb2, Mb3, Mb4, Mb5, Mb6, Mb7, Mb8, Mb9, Mb10, Mb11, Mb12 and Mb13, ACH-Z4, ACH-Y10, ACH-Y2, ACH-Y8, ACH-Y7, ACH—Y0, ACH-X, ACH-E, ACH-Mb5, ACH-Mb13, Ba1, Ba2, Ba3, Ba4, Ba5, Ba6, Ba7, Ba8, Ba9, Ba10, Ba11, Ba12, Ba13, Ba14, Ba15, Ba16, Ba17, Xanifolia Y0, Y1, Y2, Y, Y7, Y8, Y9, Y10, Xanifolia (x), Escin or Aescin or a salt, ester, metabolite thereof and Compound A to X and A1 to X1 in the application.

This invention provides a use of compound or a composition for manufacture of medicament for inhibiting the growth, migration, metastasis of cancer or altering the characteristics of membranes of cancer cell, wherein the characteristics comprise adhesion of proteins; wherein comprising the secretion of proteins or the adhesion of cells; wherein the characteristics comprise adhesion ability; wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK; wherein the cancers comprise cancers of breast, leukocyte, liver, ovarian, bladder, prostate, skin, bone, brain, leukemia, lung, colon, CNS, melanoma, renal, cervix, esophagus, testis, spleen, kidney, lymph, pancreas, stomach and thyroid; wherein the method comprises administering to the subject or contacting the cells with the extract, compositions, saponins or compounds from *Xanthoceras Sorbifolia, Harpullia, Aesculus hippocastanum, Maesa balansae* and *Barringtonia acutangula* for inhibiting cancer metastasis, wherein the cancers comprise cancers of breast, leukocyte, liver, ovarian, bladder, prostate, skin, bone, brain, leukemia, lung, colon, CNS, melanoma, renal, cervix, esophagus, testis, spleen, kidney, lymph, pancreas, stomach and thyroid cancers; wherein extracts, compositions, saponins or compounds are prepared from the husks, branches, stems, leaves, kernels, roots, barks, fruit, seeds or seed shells of the herb or plant.

The present invention provides vaccines for cancer immunotherapy. The vaccines comprise extract, compositions, compounds and saponins from Xanthoceras Sorbifolia, Harpullia, *Aesculus hippocastanum, Maesa balansae* and/or *Barringtonia acutangula*. In embodiment, the compounds can be obtained from synthesis, semi-synthesis or modification. The method comprises administering to the subject an effective amount of vaccine for enhancing the immune response. The vaccines comprise saponins isolated from *Xanthoceras Sorbifolia, Harpullia, Aesculus hippocastanum, Maesa balansae* and/or *Barringtonia acutangula*.

The present invention provides adjuvant compositions for cancer curing. The adjuvant compositions comprise extract, compositions, compounds and saponins from *Xanthoceras Sorbifolia, Harpullia, Aesculus hippocastanum, Maesa balansae* and/or *Barringtonia acutangula*. The method comprises administering to the subject an effective amount of the above adjuvant compositions for enhancing the immune response. The use of vaccine compositions comprise inhibiting cancer metastasis, wherein the cancers comprise breast, leukocyte, liver, ovarian, bladder, prostate, skin, bone, brain, leukemia, lung, colon, CNS, melanoma, renal, cervix, esophagus, testis, spleen, kidney, lymph, pancreas, stomach and thyroid cancers.

The present invention provides a use of compound for manufacture of medicament or methods for making a vaccine, wherein the vaccine comprises compounds or saponins from *Xanthoceras Sorbifolia, Harpullia, Aesculus hippocastanum, Maesa balansae* and/or *Barringtonia acutangula*, wherein the vaccine can be used for inhibiting cancer growth, wherein the vaccine is having immune adjuvant activity, wherein the saponins comprise Xanifolia Y0, Y1, Y2, Y, Y5, Y7, Y8, Y9, Y10, Xanifolia (x), Escin or Aescin or a salt, ester, metabolite thereof. In an embodiment the saponin may be selected from formulas (1A), (1B), (1C), (1D), (1E), (1F), (1G), (1H), (1J), (1K), (1L). In an embodiment the compound(s) are selected from Compound Z1 to Z13 in the application. In an embodiment the saponin(s) comprise Mb1, Mb2, Mb3, Mb4, Mb5, Mb6, Mb7, Mb8, Mb9, Mb10, Mb11, Mb12 and Mb13. In an embodiment, the compound comprises a triterpene backbone, two angeloyl groups and sugar moiety. In an embodiment the compound(s) are selected from Compound A to X and A1 to X1 in the application. In an embodiment the compound(s) are selected from ACH-Z4, ACH-Y10, ACH- Y2, ACH-Y8, ACH-Y7, ACH-Y0, ACH-X, ACH-E, ACH-Mb5, and ACH-Mb12. In an embodiment the saponins comprise Ba1, Ba2, Ba3, Ba4, Ba5, Ba6, Ba7, Ba8, Ba9, Ba10, Ba11, Ba12, Ba13, Ba14, Ba15, Ba16 and Ba17. In an embodiment the compound(s) are selected from Xanifolia Y0, Y1, Y2, Y, Y5, Y7, Y8, Y9, Y10, Xanifolia (x), Escin or Aescin or a salt, ester, metabolite thereof. This invention provides a method of treating protozoal infections. In an embodiment, this invention provides a method for treating parasites by using the above compounds, wherein the method comprises inhibiting leishmaniases, amoebiasis, trypanosomiasis, toxoplasmosis or malaria; wherein the method comprises contacting cells with an effective amount of an isolated, purified or synthesized compound, or its salt, or ester thereof, selected from the above compounds.

This invention provides a use of compound for manufacture of medicament or a method for pharmaceutical composition useful for inducing an immune response to an antigen in an individual comprising a saponin composition from *Xanthoceras Sorbifolia, Harpullia, Aesculus hippocastanum, Maesa balansae* or *Barringtonia acutangula* or synthesis. The present invention provide methods for enhancing an immune response to an antigen in an individual comprising administering an effective amount of saponins/compositions from *Xanthoceras Sorbifolia, Harpullia, Aesculus hippocastanum, Maesa balansae* and/or *Barringtonia acutangula*, This invention provides methods or a use of compound for manufacture of medicament for modulating adhesion or angiogenesis of cancer cells, antiparasitics, enhancing an immune response, providing adjuvant activities or providing vaccine activities, inhibiting cancer metastasis or growth, wherein the cancers comprise breast cancer, leukocytic cancer, liver cancer, ovarian cancer, bladder cancer, prostatic cancer, skin cancer, bone cancer, brain cancer, leukemia cancer, lung cancer, colon cancer, CNS cancer, melanoma cancer, renal cancer, cervical cancer, esophageal cancer, testicular cancer, spleenic cancer, kidney cancer, lymphatic cancer, pancreatic cancer, stomach cancer and thyroid cancer; In an embodiment the method comprises modulating the phosphatidylinositol signaling system and regulating the gene expression of RGS4, LEPR, ICFBP3, ANGPT2, GPNMB, NUPR1 or LOC-100126784. The compounds can be purified from natural resource comprising *Xanthoceras Sorbifolia, Harpullia, Aesculus hippocastanum, Maesa balansae* or *Barringtonia acutangula*, or synthesized. The compounds comprise the following:

(Our purification methods and biological assays including the MTT assay in International Application No. PCT/US05/31900, filed Sep. 7, 2004, U.S. Ser. No. 11/289,142, filed Nov. 28, 2005, and U.S. Ser. No. 11/131,551, filed May 17, 2005, and PCT/US2008/002086, 1188-ALA-PCT, filed Feb. 15, 2008, the contents of which are incorporated herein by reference)

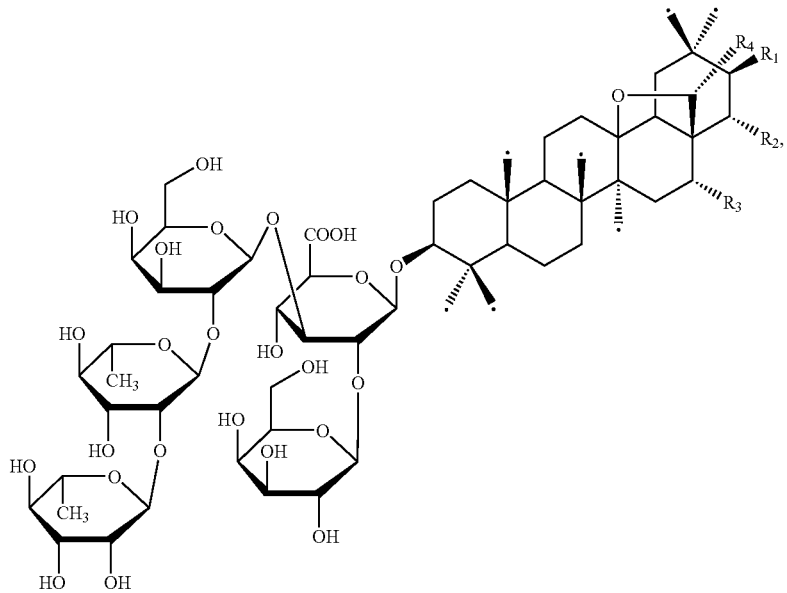

or *saponins* comprising Xanifolia Y0, Y1, Y2, Y, Y5, Y7, Y8, Y9, Y10, Xanifolia (x), Escin or Aescin or a salt, ester, metabolite thereof, or the saponin may be selected from formulas (1A), (1B), (1C), (1D), (1E), (1F), (1G), (1H), (1J), (1K), (1L). In an embodiment the compound(s) are selected from Compound Z1 to Z13 in the application. In an embodiment the saponin comprise Mb1, Mb2, Mb3, Mb4, Mb5, Mb6, Mb7, Mb8, Mb9, Mb10, Mb11, Mb12 and Mb13. In an embodiment the compound(s) are selected from Compound A to X and A1 to X1 in the application. In an embodiment the composition(s) are selected from ACH-Z4, ACH-Y10, ACH-Y2, ACH-Y8, ACH-Y7, ACH-Y0, ACH-X, ACH-E, ACH-Mb5, and ACH-Mb12. In an embodiment the saponins comprise Ba1, Ba2, Ba3, Ba4, Ba5, Ba6, Ba7, Ba8, Ba9, Ba10, Ba11, Ba12, Ba13, Ba14, Ba15, Ba16, Ba17.

wherein R1 is O(C=O)C(CH3)=CH(CH3), R2 is (E) O(C=O)CH=CH—C6H5, R3 is OH, R4 is OH, also named Mb1; or wherein R1 is O(C=O)C(CH3)=CH(CH3), R2 is (Z)—O(C=O)CH=CH—C6H5, R3 is OH, R4 is OH, also named Mb2; or wherein R1 is O(C=O)C(CH3)=CH(CH3), R2 is (Z)—O(C=O)C(CH3)=CH—C6H5, R3 is OH, R4 is OH, also named Mb2.1; or wherein R1 is O(C=O)C6H5, R2 is (E)-O(C=O)CH=CH—C6H5, R3 is OH, R4 is OH, also named Mb3; or wherein R1 is O(C=O)C6H5, R2 is (Z)—O (C=O)CH=CH—C6H5, R3 is OH, R4 is OH, also named Mb4; or wherein R1, R2, are O(C=O)C(CH3)=CH(CH3), R3 is OH, R4 is OH, also named Mb5; or wherein R1 is O(C=O)C6H5, R2 is O(C=O)C(CH3)=CH(CH3), R3 and R4 are OH, also named Mb6; or

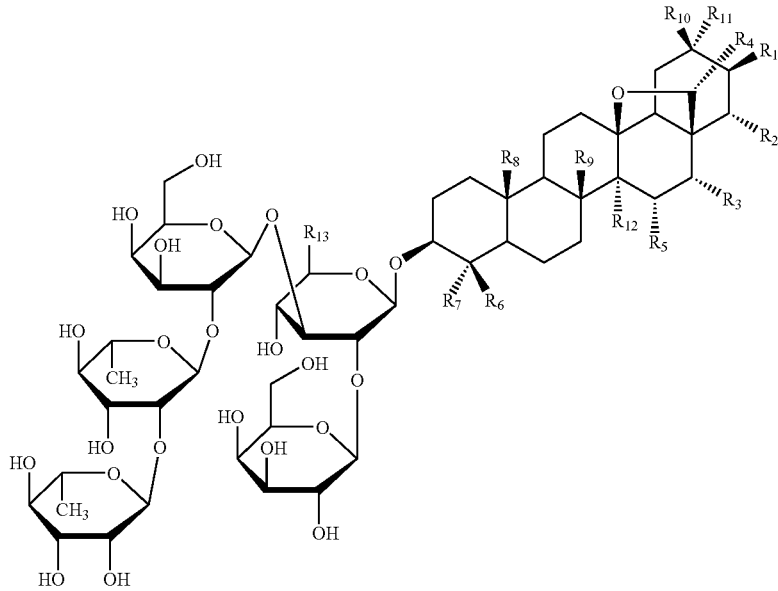

wherein R1 is O(C=O)C6H5, R2 is O(C=O)CH=CH—C6H5, R3, R4, R5 are OH, R6, R7, R8, R9, R10, R11, R12 are CH3, R13 is COOH also named Mb7; or wherein R1 is O(C=O)C6H5, R2 is O(C=O)CH=CH—C6H5, R3, R4, R5 are OH, R6 is CH2OH, R7, R8, R9, R10, R11, R12 are CH3, R13 is COOH also named Mb8; or wherein R1 is O(C=O)C(CH3)=CH(CH3), R2 is O(C=O)CH=CH—C6H5, R3, R4 are OH, R6, R7, R8, R9, R10, R11, R12 are CH3, R13 is COOH also named Mb9; or wherein R1 is O(C=O)C(CH3)=CH(CH3), R2 is O(C=O)CH=CH—C6H5, R3, R4 are OH, R6 is CH2OH, R7, R8, R9, R10, R11, R12 are CH3, R13 is COOH, also named Mb10; or wherein R1, R2, are O(C=O)C(CH3)=CH(CH3), R3 is OH, R4 is CH2OH, R5 is H, R6, R7, R8, R9, R10, R11, R12 are CH3, R13 is COOH, also named Mb11; or wherein R1 is O(C=O)C(CH3)=CH(CH3), R2 is O(C=O)CH=CH—C6H5, R3, R4 are OH, R6, R7, R8, R9, R10, R11, R12 are CH3, R13 is COOCH3, also named Mb12;

or wherein R1 is O(C=O)C(CH3)=CH(CH3), R2 is (Z)—O(C=O)C(CH3)=CH—C6H5, R3 is OH, R4 is OH, R5 is H, and R6, R7, R8, R9, R10, R11, R12 are CH3, R13 is COOH, also named Mb13; or

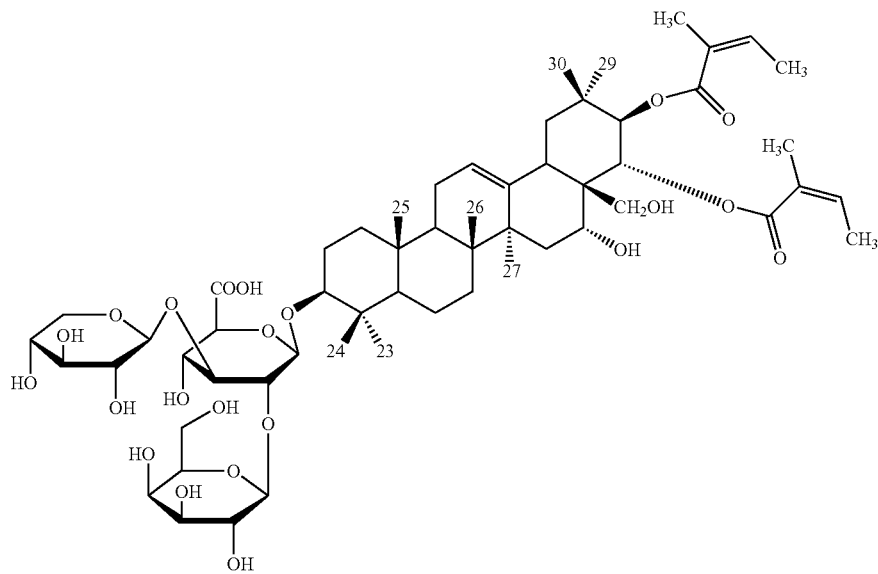

3-O-[β-D-galactopyranosyl(1→2)]-β-D-xylopyranosyl (1→3)-β-D-glucuronopyranosyl-21-O-angeloyl, 22-O-angeloyl-3β, 15α, 21β, 22α, 28-pentahydroxyolean-12-ene, named Ba 1

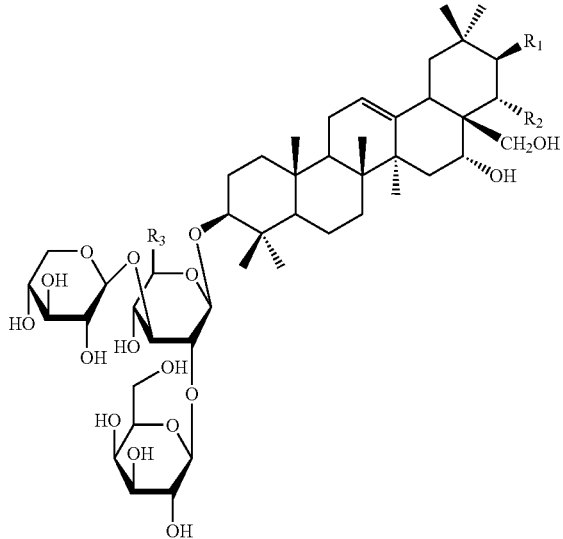

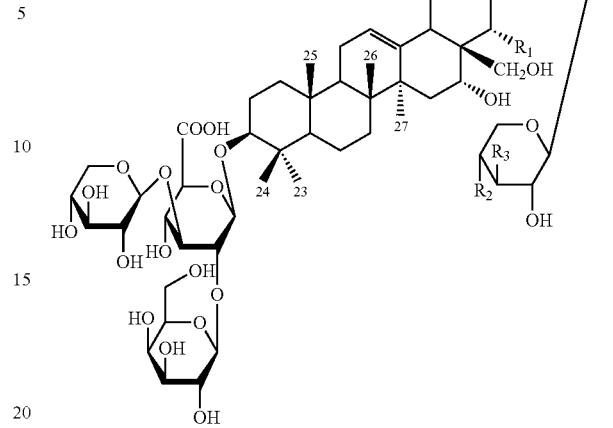

wherein R1 is O(C=O)C(CH3)=CH(CH3), R2 is O(C=O)C(CH3)=CH(CH3), R3 is COOCH3, formula is 3-O-[β-D-galactopyranosyl(1→2)]-β-D-xylopyranosyl(1→3)-β-D-methylglucuronopyranosyl-21-O-angeloyl, 22-O-angeloyl-3β, 15α, 21β, 22α, 28-pentahydroxyolean-12-ene, named Ba 2; or wherein R1 is O(C=O)C6H5, R2 is O(C=O)C(CH3)=CH(CH3), R3 is COOH, formula is: 3-O-[β-D-galactopyranosyl(1→2)]-β-D-xylopyranosyl(1→3)-β-D-glucuronopyranosyl-21-O-benzoyl, 22-O-angeloyl-3β, 15α, 21β, 22α, 28-pentahydroxyolean-12-ene, named Ba 3; or wherein R1 is O(C=O)C6H5, R2 is O(C=O)C(CH3)=CH(CH3), R3 is COOCH3, formula is: 3-O-[β-D-galactopyranosyl(1→2)]-β-D-xylopyranosyl(1→3)-β-D-methylglucuronopyranosyl-21-O-benzoyl, 22-O-angeloyl-3β, 15α, 21β, 22α, 28-pentahydroxyolean-12-ene, named Ba 4; or wherein R1 is O(C=O)C6H5, R2 is O(C=O)C6H5, R3 is COOH, formula is: 3-O-[β-D-galactopyranosyl(1→2)]-β-D-xylopyranosyl(1→3)-β-D-glucuronopyranosyl-21-O-benzoyl, 22-O-benzoyl-3β, 15α, 21β, 22α, 28-pentahydroxyolean-12-ene, named Ba 5; or wherein R1 is O(C=O)C6H5, R2 is O(C=O)C6H5, R3 is COOCH3, formula is: 3-O-[β-D-galactopyranosyl(1→2)]-β-D-xylopyranosyl(1→3)-β-D-methylglucuronopyranosyl-21-O-benzoyl, 22-O-benzoyl-3β, 15α, 21β, 22α, 28-pentahydroxyolean-12-ene, named Ba 6; or wherein R1 is O(C=O)C6H5, R2 is O(C=O)CH3CH3, R3 is COOH, formula is: 3-O-[β-D-galactopyranosyl(1→2)]-β-D-xylopyranosyl(1→3)-β-D-glucuronopyranosyl-21-O-benzoyl, 22-O-isobutyryl-3β, 15α, 21β, 22α, 28-pentahydroxyolean-12-ene, named Ba 7; or wherein R1 is O(C=O)C6H5, R2 is OH, R3 is COOH, formula is: 3-O-[β-D-galactopyranosyl(1→2)]-β-D-xylopyranosyl(1→3)-β-D-glucuronopyranosyl-21-O-benzoyl-3β, 15α, 21β, 22α, 28-pentahydroxyolean-12-ene, named Ba 8 wherein R1 is OH, R2 is O-benzoyl, R3 is O-benzoyl, 3-O-[β-D-galactopyranosyl(1→2)]-β-D-xylopyranosyl(1→3)-β-D-glucuronopyranosyl-21-O-[3,4-dibenzoyl-β-D-xylopyranosyl]-3β, 15α, 21β, 22α, 28-pentahydroxyolean-12-ene, named Ba9

R1 is O-acetyl, R2 is O-benzoyl, R3 is O-benzoyl 3-O-[β-D-galactopyranosyl(1→2)]-β-D-xylopyranosyl(1→3)-β-D-glucuronopyranosyl-21-O-[3,4-dibenzoyl-β-D-xylopyranosyl]-22-O-acetyl-3β, 15α, 21β, 22α, 28-pentahydroxyolean-12-ene, named Ba10

3-O-[β-D-galactopyranosyl(1→2)]-β-D-xylopyranosyl(1→3)-β-D-glucuronopyranosyl-21-O-[3-angeloyl, 4-benzoyl-β-D-xylopyranosyl]-3β, 15α, 21β, 22α, 28-pentahydroxyolean-12-ene, named Ba11

3-O-[β-D-galactopyranosyl(1→2)]-β-D-xylopyranosyl(1→3)-β-D-glucuronopyranosyl-21-O-[3,4-diangeloyl-β-D-xylopyranosyl]-3β, 15α, 21β, 22α, 28-pentahydroxyolean-12-ene, named Ba12

3-O-[β-D-galactopyranosyl(1→2)]-β-D-xylopyranosyl(1→3)-β-D-glucuronopyranosyl-21-O-[3-angeloyl, 4-tigloyl-β-D-xylopyranosyl]-3β, 15α, 21β, 22α, 28-pentahydroxyolean-12-ene, named Ba13

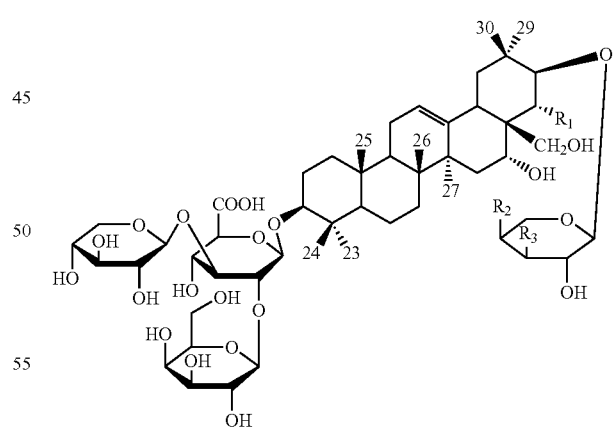

Wherein R1 is OH, R2 is O-benzoyl, R3 is O-benzoyl
3-O-[β-D-galactopyranosyl(1→2)]-β-D-xylopyranosyl(1→3)-β-D-glucuronopyranosyl-21-O-[3,4-dibenzoyl-α-L-arabinopyranosyl]-3β, 15α, 21β, 22α, 28-pentahydroxyolean-12-ene, named Ba14

Wherein R1 is O-acetyl, R2 is O-benzoyl, R3 is O-benzoyl
3-O-[β-D-galactopyranosyl(1→2)]-β-D-xylopyranosyl(1→3)-β-D-glucuronopyranosyl-21-O-[3,4-dibenzoyl-α-L-arabinopyranosyl]-22-O-acetyl-3β, 15α, 21β, 22α, 28-pentahydroxyolean-12-ene, named Ba15

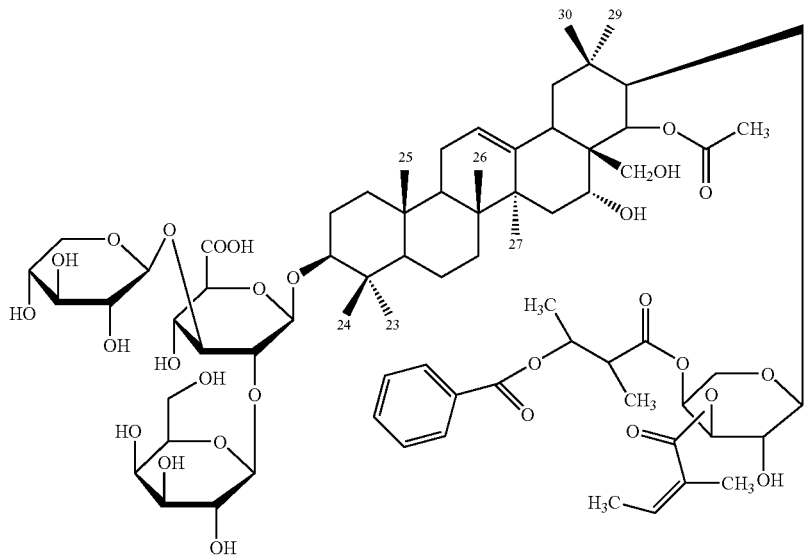

3-O-[β-D-galactopyranosyl(1→2)]-β-D-xylopyranosyl (1→3)-β-D-glucuronopyranosyl-21-O-[3-angeloyl-4-(3-benzoyl-2-methylbutyryl)-α-L-arabinopyranosyl]-22-O-acetyl-3β, 15α, 21β, 22α, 28-pentahydroxyolean-12-ene, named Ba16

The anti-cancer activity of ACH's compounds with ES2 cell: the IC50 of ACH-Z4 is 40 ug/ml, ACH-Y3 is 20 ug/ml, ACH-Y10 is 20 ug/ml, ACH-Y2 is 35 ug/ml, ACH-Y8 is 35 ug/ml, ACH-Y7 is 65 ug/ml, ACH-Y0 is 20 ug/ml, ACH-X is 40 ug/ml, ACH-E is 60 ug/ml

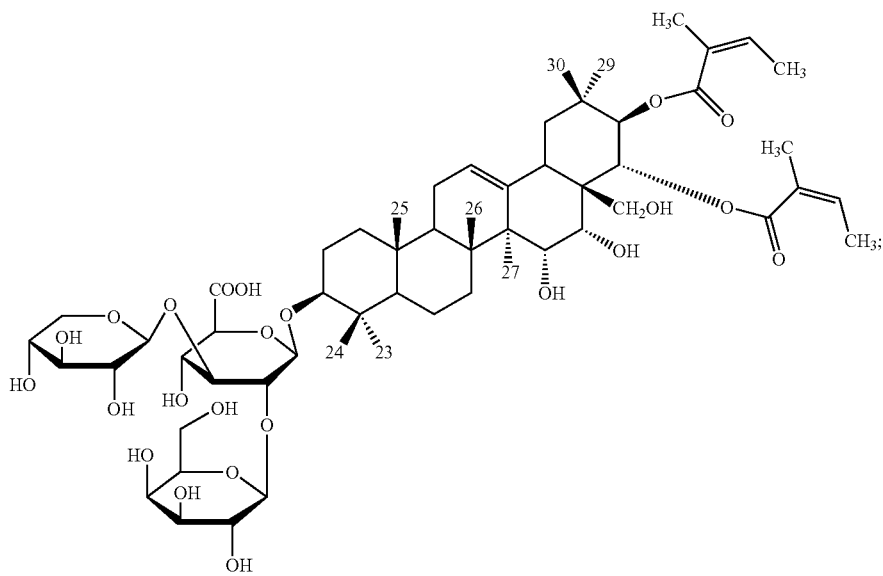

3-O-[β-D-galactopyranosyl(1→2)]-β-D-xylopyranosyl (1→3)-β-D-glucuronopyranosyl-21-O-angeloyl, 22-O-angeloyl-3β, 15α, 16α, 21β, 22α, 28-hexahydroxyolean-12-ene, also named Ba 17

Anti-Cancer Activities:

The anti-cancer activity of Mb's compounds with ES2 cell: the IC50 of Mb1 is 8 ug/ml, Mb2 is /ml, Mb3 is 8 ug/ml, Mb4 is 15 ug/ml, Mb5 is 6.5 ug/ml, and Mb6 is 10 ug/ml, Mb7 is 12 ug/ml, Mb8 is 20 ug/ml, Mb9 is 18 ug/ml, Mb12 is 10 ug/ml.

The anti-cancer activity of Ba compounds with ES2 cell: Ba1 is 5 ug/ml, Ba2 is 5 ug/ml, Ba3 is 8 ug/ml, Ba 5 is 16 ug/ml, Ba7 is 11 ug/ml, Ba8 is 20 ug/ml, Ba9 is 12 ug/ml, Ba17 is 5 ug/ml.

The anti-cancer activity of Xanifolia Y with cells: the IC50 of Y on (bladder) TB9 cells is 5 ug/ml; IC50 of Y on (lung) H460 cells is 7.5 ug/ml; 1050 of Y on HeLa cells is 20 ug/ml; IC50 of Y on skin cells is 12 ug/ml; IC50 of Y on ES2 (ovarian) cells is 5 ug/ml; IC50 of pure Y on (Mouth) KB cells is 6 ug/ml;

IC50 of Z12 on ES2 (ovarian) cells is 16 ug/ml; Z4 is 20 ug/ml

IC50 of Mb5: (bladder) TB9 is 6.5 ug/ml, (Prostate) DU145 is 7.6 ug/ml, (Lung) H460 is 12 ug/ml (Liver) HepG2 is 6.5 ug/ml, (brain) T98G is 12 ug/ml, (Skin) SK-MELS is 25 ug/ml, (Ovary) ES2 is 6.5 ug/ml, (Breast) MCF7 is 11 ug/ml.

IC50 of ACH-Mb5: (bladder) TB9 is 5.7 ug/ml, (Prostate) DU145 is 6.4 ug/ml, (Lung) H460 is 6.5 ug/ml (Liver) HepG2 is 4 ug/ml, (brain) T98G is 6 ug/ml, (Skin) SK-MELS is 22 ug/ml, (Ovary) ES2 is 8 ug/ml, (Breast) MCF7 is 13 ug/ml.

This invention provides a method or composition for reducing the expression and secretion of adhesion proteins to cure diseases, wherein the diseases comprise cancer growth, leg swelling, symptoms of chronic venous insufficiency, peripheral edema, lipemic, chronic venous disease, varicose vein disease, varicose syndrome, venous stasis, expectorant, peripheral vascular disorders, cerebro-organic convulsion, cerebral circulation disorder, cerebral edema, psychoses, dysmenorrheal, hemorrhoids, episiotomies, peripheral edema formation or postoperative swelling; leg pain; for pruritis, lower leg volume, symptoms of pain; thrombosis, thromophlebitis or for preventing gastric ulcers, spasms, comprising administering to a subject, in need thereof, an effective amount of the composition of this invention.

In an embodiment, the method comprises interacting with adhesion proteins, wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK. In an embodiment, this invention provides a method of reducing the secretion of fibronectin.

In an embodiment, the method comprises reducing the adhesion ability of adhesion proteins; wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK.

In an embodiment, the method comprises modulating the expression or secretion of adhesion proteins, wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK. In an embodiment, the method comprises blocking the secretion of adhesion proteins, wherein the adhesion proteins comprise fibronectin. In an embodiment the method comprises administering to a subject or contacting the cell with an effective amount of the compound selected from formulas in this application.

In an embodiment, this invention provides a method and composition for modulating adhesion or angiogenesis of cancer cells, antiparasitics or manufacturing an adjuvant composition. In an embodiment, this invention provides a method of treating protozoal infections including leishmaniases, amoebiasis, trypanosomiasis, toxoplasmosis and malaria infections.

This invention provides a use of compound for manufacture of medicament, a method and a composition for altering the characteristics of adhesion proteins to cure diseases, wherein the characteristics comprising adhesion ability, wherein the method comprises reducing the secretion of fibronectin, wherein the diseases comprise cancer growth, leg swelling, symptoms of chronic venous insufficiency, peripheral edema, lipemic, chronic venous disease, varicose vein disease, varicose syndrome, venous stasis, expectorant, peripheral vascular disorders, cerebro-organic convulsion, cerebral circulation disorder, cerebral edema, psychoses, dysmenorrheal, hemorrhoids, episiotomies, peripheral edema formation or postoperative swelling; symptoms of leg pain; pruritis, lower leg volume, symptoms of pain; thrombosis, thromophlebitis; for preventing gastric ulcers antispasmotic, comprising administering to a subject, in need thereof, an effective amount of the composition of this invention; wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK. In an embodiment the method is administering contacting an effective amount in a subject with the compound selected from formulas in this application.

This invention provides a process and method for administration of the composition, wherein administration is by intravenous injection, intravenous drip, intraperitoneal injection or oral administration; wherein administration is by intravenous drip: 0.05-0.2 mg/kg compound dissolved in 250 ml of 10% glucose solution or in 250 ml of 0.9% NaCl solution, or by intravenous injection: 0.05-0.2 mg/kg/day compound dissolved in 10-20 ml of 10% glucose solution or of 0.9% NaCl solution, or by intravenous drip: 0.1-0.2 mg/kg/day compound dissolved in 250 ml of 10% glucose solution or in 250 ml of 0.9% NaCl solution, or by intravenous injection: 0.1-0.2 mg/kg/day compound dissolved in 10-20 ml of 10% glucose solution or of 0.9% NaCl solution, or by intraperitoneal injection (I.P.): 2.5 mg/kg/day compound dissolved in 10% glucose solution or of 0.9% NaCl solution, or by oral administration wherein the dosage in mammal is 1-10 mg/Kg, 10-30 mg/Kg, 30-60 mg/Kg, or 60-90 mg/Kg compound, or by intravenous injection or intravenous drip wherein the dosage in mammal is 0.01-0.1 mg/Kg, 0.1-0.2 mg/Kg, 0.2-0.4 mg/Kg, or 0.4-0.6 mg/Kg compound, or by intraperitoneal injection (I.P.) wherein the dosage in mammal is 1-3 mg/Kg, 3-5 mg/Kg, 4-6 mg/Kg, or 6-10 mg/Kg compound.

The methods and uses of an isolated, purified or synthesized compound or its salt, ester, metabolite or derivative thereof, having the formula of:

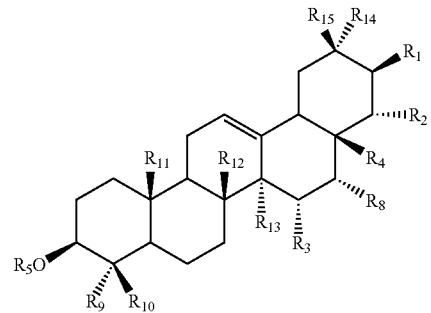

also named (1A), wherein R1 is selected from hydrogen, hydroxyl, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, and derivatives thereof;

R2 is selected from hydrogen, hydroxyl, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, and derivatives thereof;

R4 represents $CH_2R6$ or $COR6$, wherein R6 is selected from a group consisting of hydroxyl, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, and derivatives thereof; R3 is H or OH; R8 is H or OH;

R5 is a hydrogen, heterocyclic or sugar moiety(ies), wherein the sugar moiety(ies) is/are selected from a group consisting of glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, and derivatives or combination thereof; wherein R9, R10, R11, R12, R13, R14, R15 are independently attached a group selecting from $CH_3$, $CH_2OH$, CHO, COOH, COO-alkyl, COO-aryl, COO-heterocyclic, COO-heteroaryl, $CH_2O$aryl, $CH_2O$-heterocyclic, $CH_2O$-heteroaryl, alkyls group, hydroxyl, acetyl group, particularly $CH_3$; wherein at least two of R1, R2 and R6 are comprising a group selected from O-angeloyl, O-tigloyl, O-senecioyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, and derivatives thereof; or at least one of R1, R2, and R4 is a sugar moiety substituted with at least two groups selected from a group consisting of angeloyl, acetyl, tigloyl, senecioyl, benzoyl, dibenzoyl, alkanoyl, alkenoyl, benzoyl alkyl substituted alkanoyl, O-alkanoyl substituted phenyl, O-alkenoyl substituted phenyl, aryl, acyl, heterocylic, heteroraryl, and a derivative thereof; or wherein R4 is $CH_2R6$; wherein R1 and R2 independently consists an O-angeloyl group, or at least two of R1, R2 and R6 are O-angeloyl or at least one of R1, R2 or R6 is a sugar moiety with two O-angeloyls; or wherein R5 is/are the sugar moiety(ies) selected from the following sugars and alduronic acids: glucose, galactose, rhamnose, arabinose, xylose, fucose, allose, altrose, gulose, idose, lyxose, mannose, psicose, ribose, sorbose, tagatose, talose, fructose, glucuronic acid, galacturonic acid; or their derivatives thereof, or the combination thereof; wherein the sugar preferably comprises glucuronic acid, arabinose and galactose. In an embodiment, wherein R5 is/are sugar moiety(ies) selected from a group consisting of glucose, galactose, arabinose, alduronic acid, glucuronic acid, galacturonic acid, and a derivative or combination thereof; in embodiment, the acyl has 2 to 10 carbons.

In an embodiment the method is administering contacting the compounds, wherein the compound is selected from the following:
a) An isolated, purified or synthesized compound having structure Xanifolia(Y), or chemical name: 3-O-[β-D-galactopyranosyl(1→2)]-α-L-arabinofuranosy (1→3)-β-D-glucuronopyranosyl-21,22-O-diangeloyl-3β, 15α, 16α, 21β, 22α, 28-hexahydroxyolean-12-ene;

b) An isolated, purified or synthesized compound having structure Xanifolia (Y1),

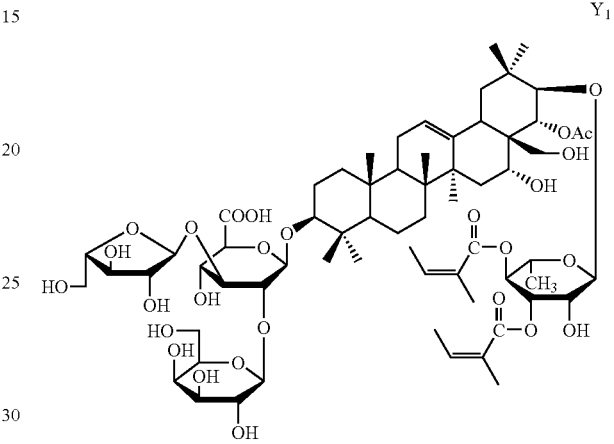

or chemical name: 3-O-[β-D-galactopyranosyl (1→2)]-α-L-arabinofuranosyl(1→3)-β-D-glucuronopyranosyl-21-O-(3, 4-diangeloyl)-α-L-rhamnophyranosyl-22-O-acetyl-3β,16α, 21β, 22α, 28-pentahydroxyolean-12-ene;

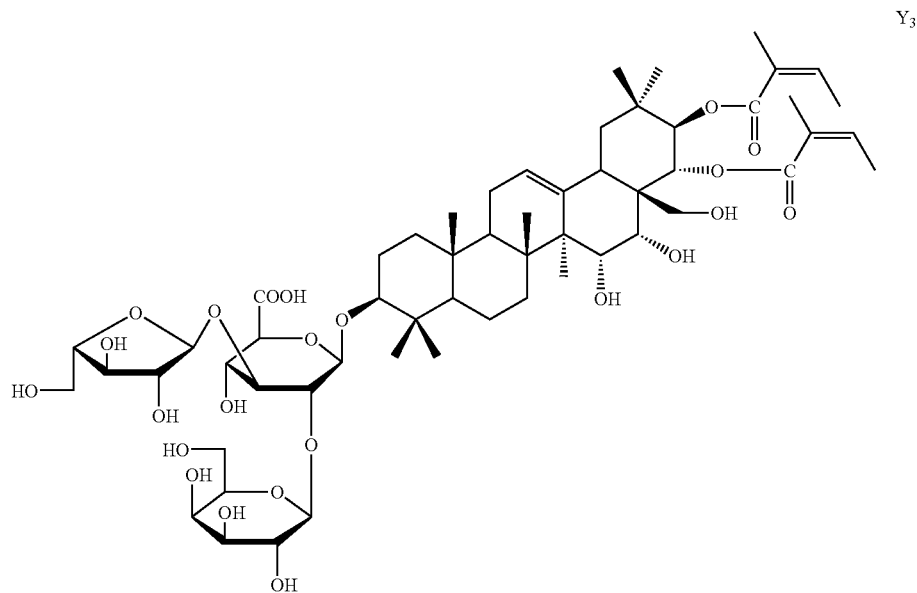

c) An isolated, purified or synthesized compound having structure Xanifolia (Y2),

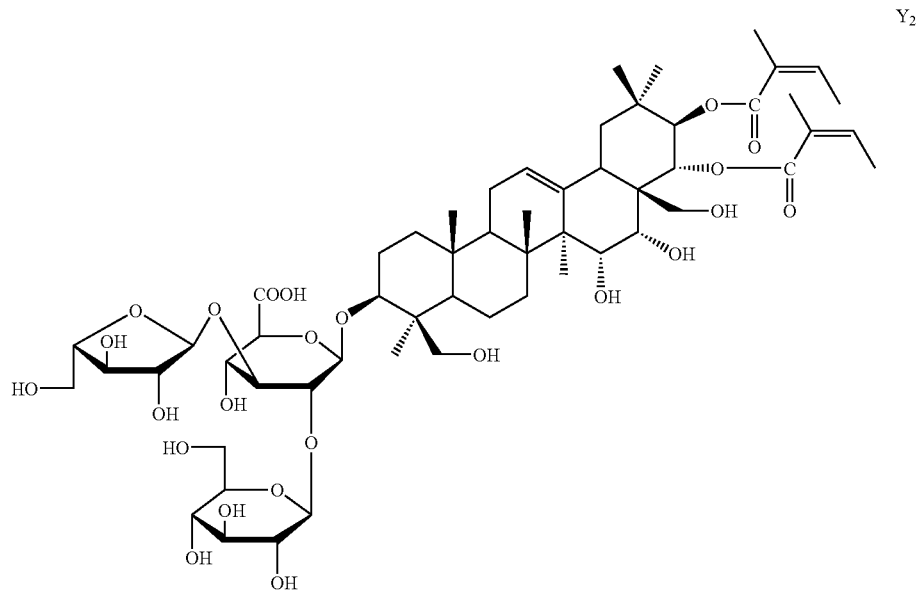

or chemical name: 3-O-[β-D-glucopyranosyl-(1→2)]-α-L-arabinofuranosy (1→3)-β-D-glucuronopyranosyl-21,22-O-diangeloyl-3β, 15α, 16α, 21β, 22α, 24β, 28-heptahydroxy-olean-12-ene;

d) An isolated, purified or synthesized compound having structure Xanifolia (Y8),

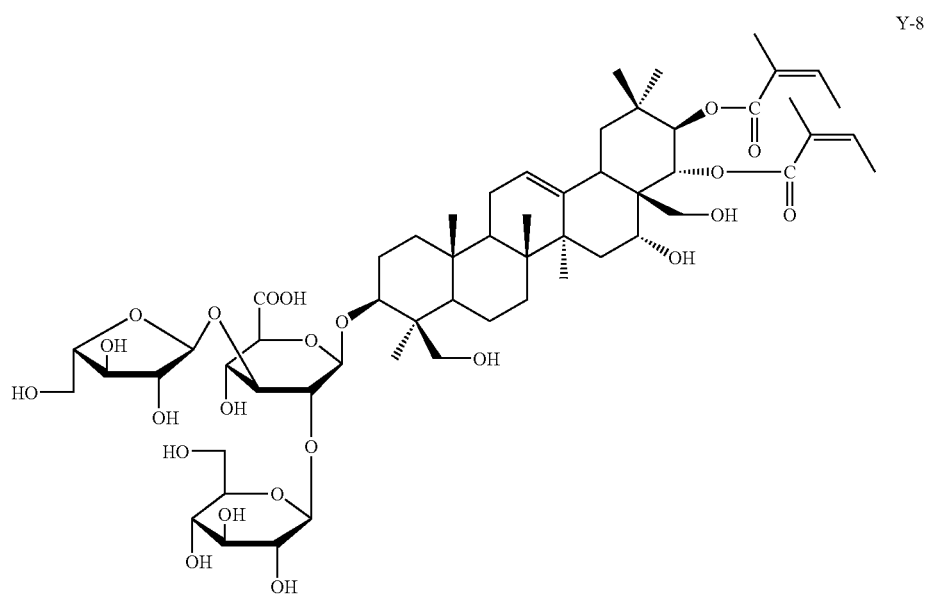

or chemical name: 3-O-[β-glucopyranosyl (1→2)]-α-arabinofuranosyl(1→3)-β-glucuronopyranosyl-21,22-O-diangeloyl-3β, 16α, 21β, 22α, 24β, 28-hexahydroxyolean-12-ene;

e) An isolated, purified or synthesized compound having structure Xanifolia (Y9),

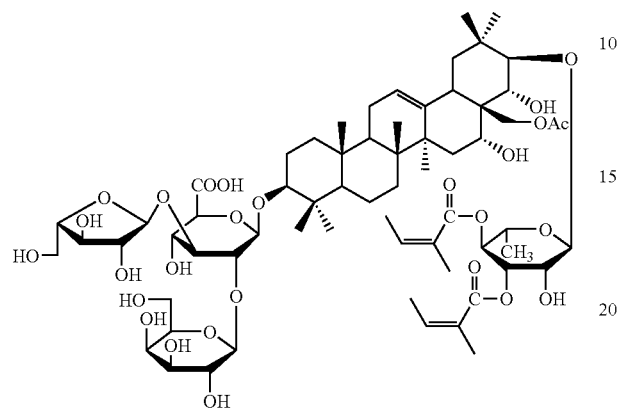

or chemical name: 3-O-[β-galactopyranosyl(1→2)]-α-arabinofuranosyl(1→3)-β-glucuronopyranosyl-21-O-(3,4-diangeloyl)-α-rhamnopyranosyl-28-O-acetyl-3β, 16α, 21β, 22α, 28-pentahydroxyolean-12-ene; and f) An isolated, purified or synthesized compound having structure Xanifolia (Y10),

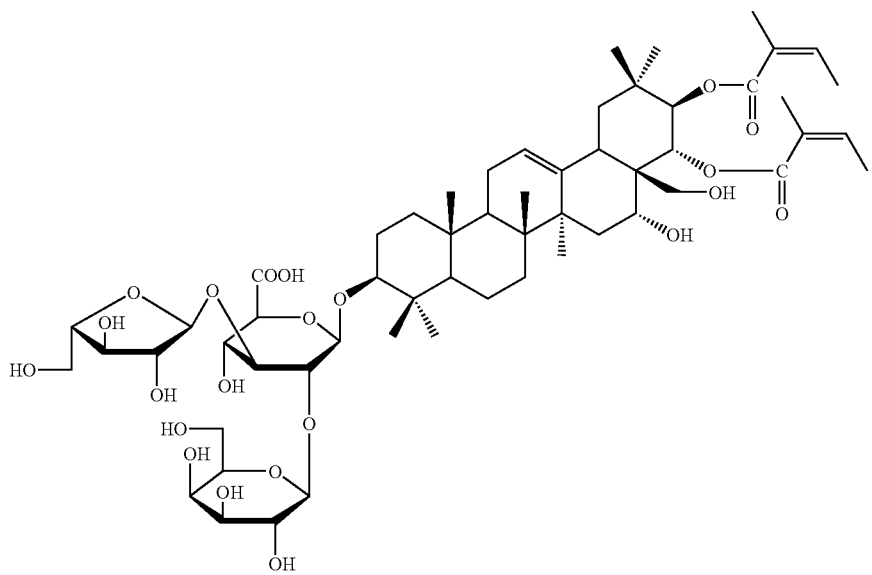

or chemical name: 3-O-[β-galactopyranosyl(1→2)]-α-arabinofuranosyl(1→3)-β-glucuronopyranosyl-21,22-O-diangeloyl-3β, 16α, 21β, 22α, 28-pentahydroxyolean-12-ene.

g) An isolated, purified or synthesized compound having structure Xanifolia (Y0),

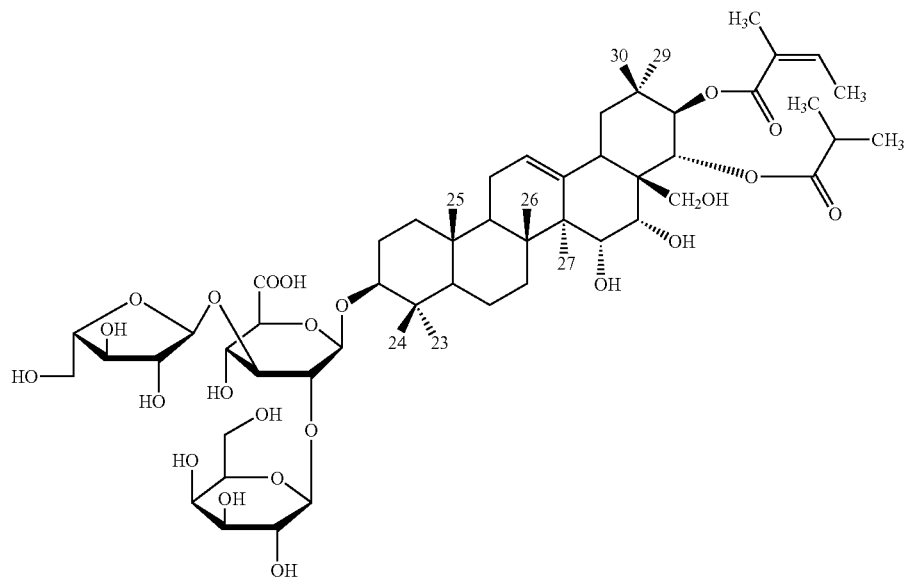

or chemical name: 3-O-[β-D-galactopyranosyl(1→2)]-α-L-arabinofuranosyl(1→3)-β-D-glucuronopyranosyl-21-O-angeloyl, 22-O-(2-methylpropanoyl)-3β, 15α, 16α, 21β, 22α, 28-hexahydroxyolean-12-ene, h) An isolated, purified or synthesized compound having structure Xanifolia (X),

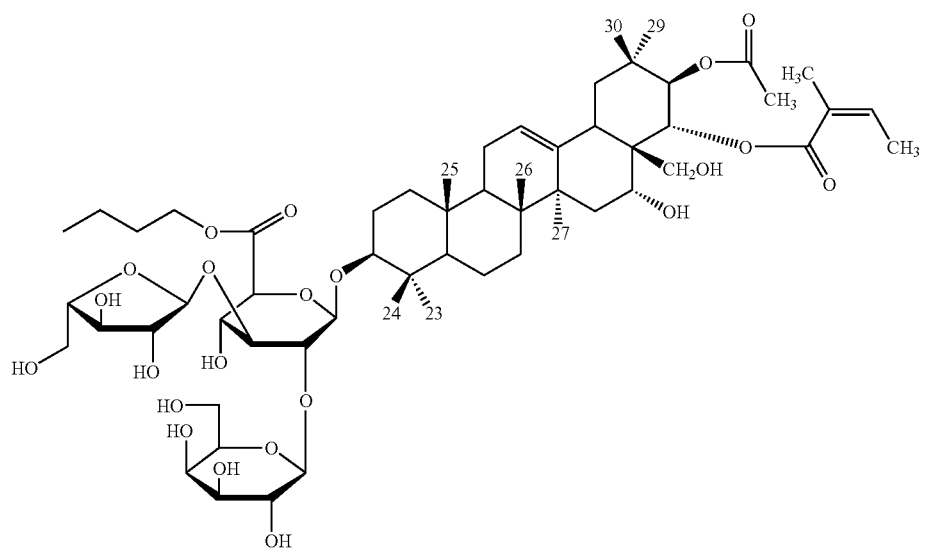

or chemical name: 3-O-{[β-D-galactopyranosyl(1→2)]-[α-L-arabinofuranosyl(1→3)]-β-D-glucuronopyranoside butyl ester}-21-O-acetyl-22-O-angeloyl-3β,16α, 21β,22α, 28-pentahydroxyolean-12-ene.

i) An isolated, purified or synthesized compound having structure (Y7),
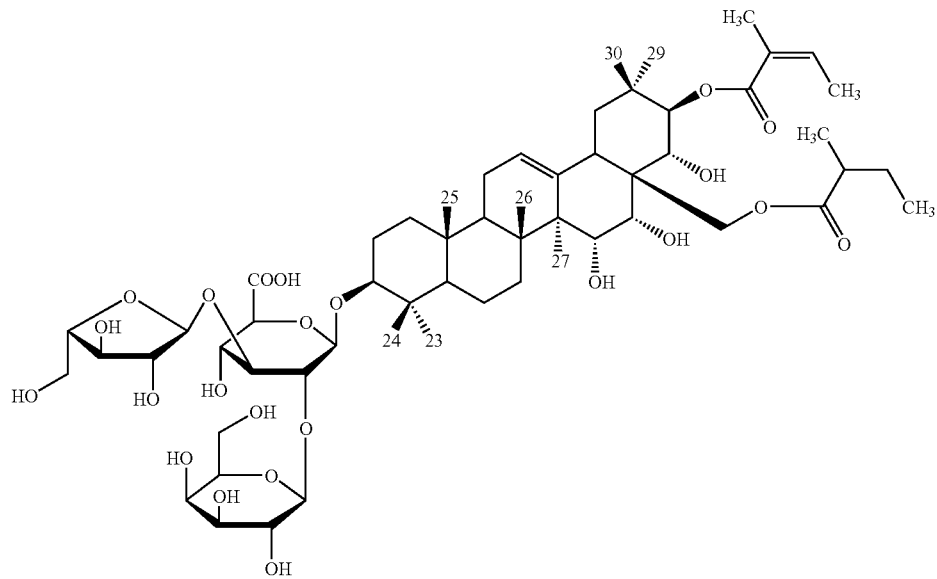
or chemical name: 3-O-[β-D-galactopyranosyl-(1→2)]-α-L-arabinofuranosyl-(1→3)-β-D-glucuronopyranosyl-21-O-angeloyl-28-O-2-methylbutanoyl-3β, 15α, 16α, 21β, 22α, 28-hexahydroxyolean-12-ene
j) An isolated purified or synthesized compound having structure (ACH):
(ACH-Y)
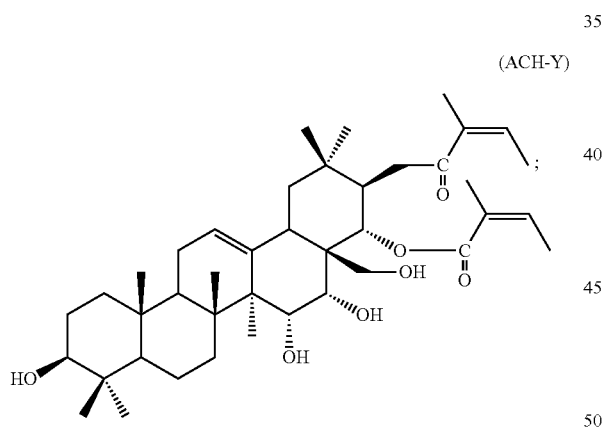
-continued
ACH-Y10
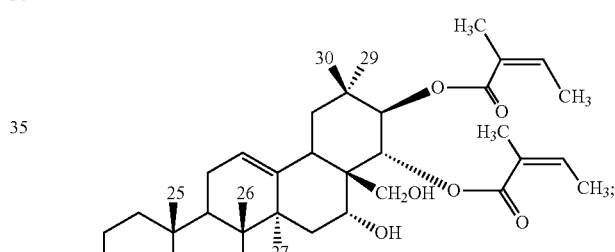
ACH-Z4
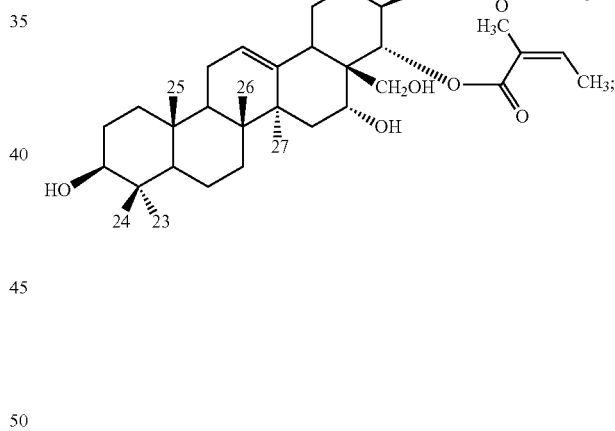
ACH-Y2
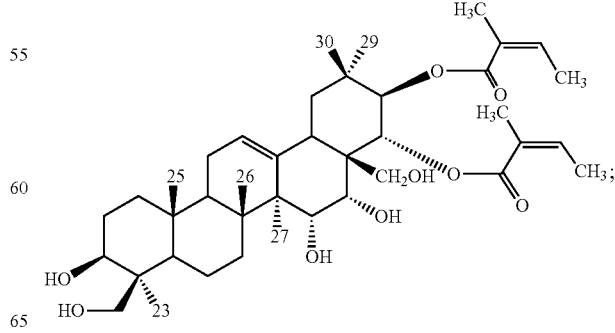

ACH-Y8
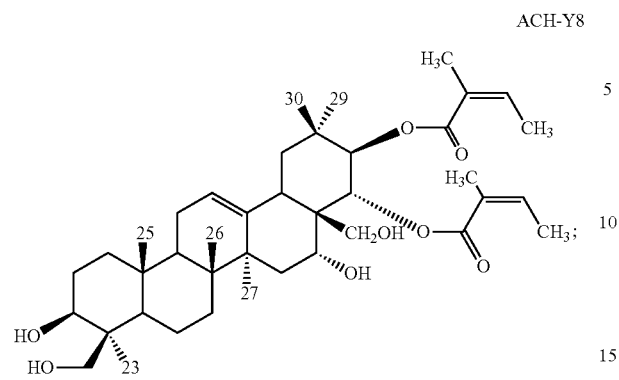
ACH-X
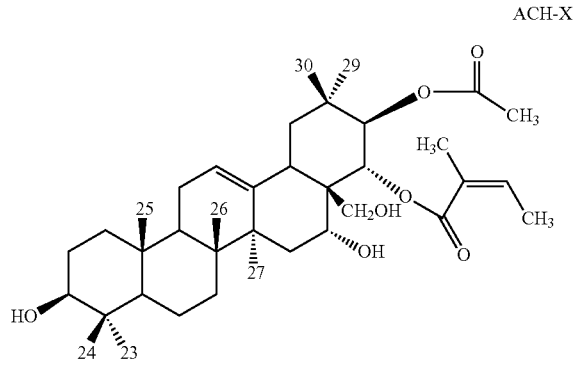
ACH-Y7
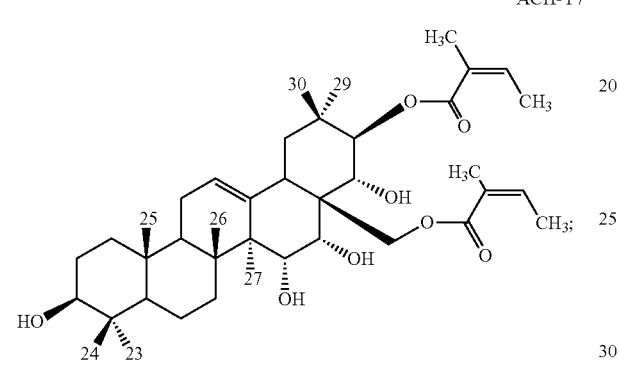
ACH-Mb5
ACH-Y0
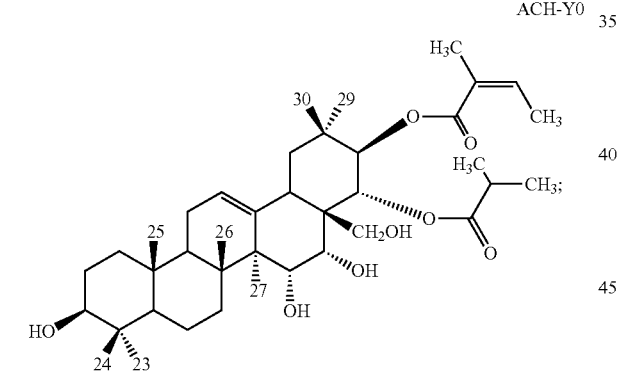
ACH-Mb12
ACH-E
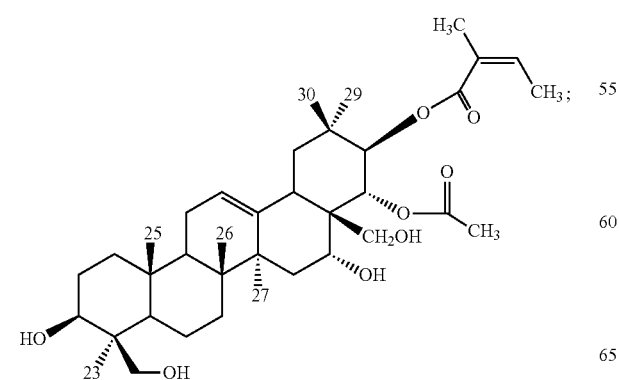
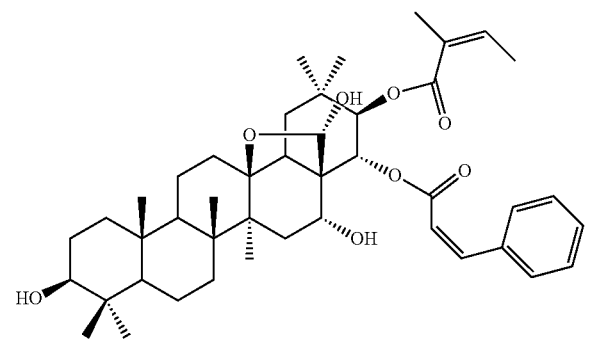
In an embodiment the method is administering contacting the compound, wherein the compound is selected from the following:

k) An isolated, purified or synthesized compound having a structure:

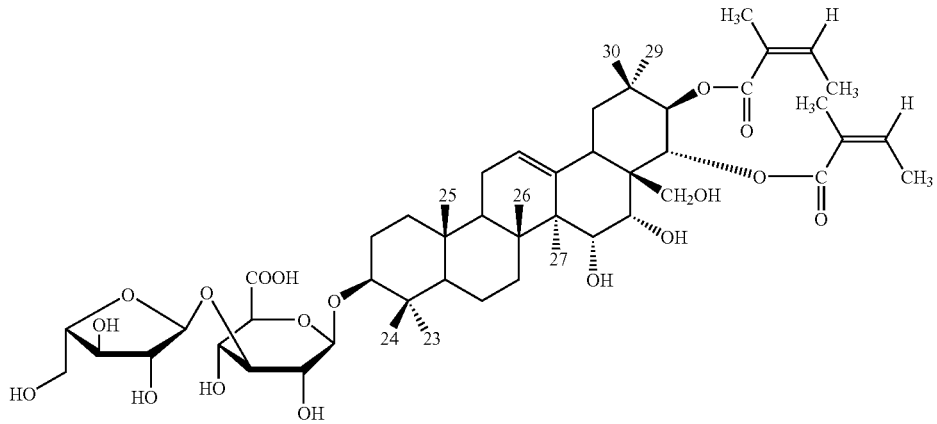

l) An isolated, purified or synthesized compound having a structure(Y5):

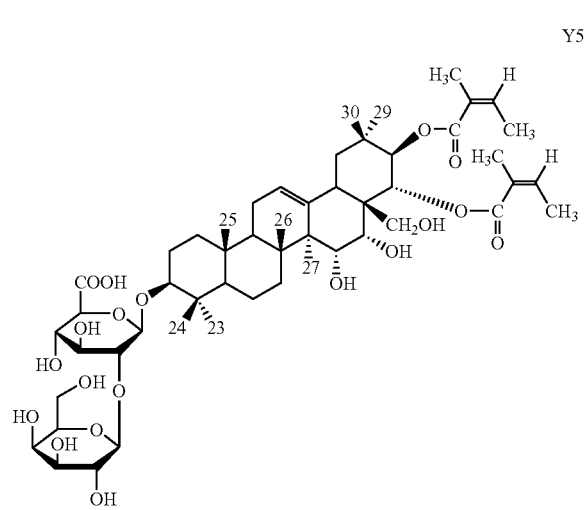

In an embodiment the method comprises administering to a subject or contacting the cell with the compound, wherein the compound is isolated, purified or synthesized having a structure selected from following formulae:

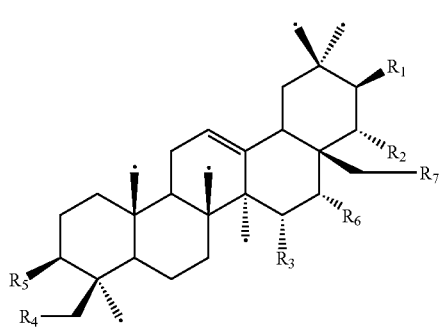

(1C)

wherein R1, R2 are individually selected of an O-acetyl or O-angeloyl; wherein the R3, R4, R5, R6, R7 is hydrogen or hydroxyl In an embodiment the method comprises administering to a subject or contacting the cell with compound in this application comprising Xanifolia Y0, Y1, Y2, Y, Y5, Y7, Y8, Y9, Y10, Xanifolia (x), Escin or Aescin or a salt, ester, metabolite thereof. In an embodiment the compounds may be selected from formulas (1A), (1 B), (1 C), (1 D), (1E), (1F), (1G), (1H), (1J), (1K), (1L). In an embodiment, the compound comprises a triterpene backbone, two angeloyl groups and sugar moiety. In an embodiment the compound(s) are selected from Compound A to X and A1 to X1 in the application. In an embodiment the compound(s) are selected from Compound Z1 to Z13 in the application. In an embodiment the method comprises administering to a subject or contacting the cell with compound comprising of a triterpene wherein the carbon position 21, 21 has an unsaturated group and sugar moieties at carbon 3.

In an embodiment, methods and compounds of this application reduce the ability of bacteria, in colonization and tropism of cells.

In an embodiment, methods and compounds of this application reduce the adhesive ability of cells or viruses in order to inhibit viruses binding to host cells, wherein the viruses comprise HIV.

This invention provides a use of compound for manufacture of medicament, a method and a composition for modulating adhesion or anti-angiogenesis of cancer tumor, antiparasitics or manufacturing an adjuvant composition, wherein the modulating adhesion of cancer cell comprising modulating the secretion or expression of adhesion protein, wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK; wherein the modulating comprises reducing, inhibiting and stimulating, wherein modulating adhesion protein comprises reducing the fibronectin for inhibiting the metastasis or growth of cancer cells, wherein the cancer is selected from breast cancer, leukocytic cancer, liver cancer, ovarian cancer, bladder cancer, prostatic cancer, skin cancer, bone cancer, brain cancer, leukemia cancer, lung cancer, colon cancer, CNS cancer, melanoma cancer, renal cancer, cervical cancer, esophageal cancer, testicular cancer, spleenic cancer, kidney cancer, lymphatic cancer, pancreatic cancer, stomach cancer and thyroid cancer; wherein modulating adhesion of cancer cells comprises modulating the secretion or expression of adhesion protein, wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK; wherein modulating comprises reducing, inhibiting and stimulating; wherein modulating angiogenesis comprises inhibiting and stimulating angiopoietin, wherein comprising angiopoietin 1, angiopoietin 2, angiopoietin 3, angiopoietin 4, angiopoietin 5, angiopoietin 6 and angiopoietin 7; wherein the angiopoietin comprising angiopoietin-like 1, angiopoietin-like 2, angiopoietin-like 3, angiopoietin-like 4, angiopoietin-like 5, angiopoietin-like 6 and angiopoietin-like 7; wherein the modulating comprises positive and negative regulating; wherein modulating angiopoietin comprises stimulating angiopoietin 2 in order to inhibit angiogenesis; wherein modulating angiopoietin comprises inhibiting angiopoietin 1 in order to inhibit angiogenesis; wherein modulating angiopoietin comprises inhibiting angiopoietin-like 1; wherein modulating angiopoietin comprises inhibiting angiopoietin-like 4; wherein the antiparasitics comprise inhibiting leishmaniases, amoebiasis, trypanosomiasis, toxoplasmosis or malaria, wherein the method comprises administering to a subject or contacting the cell with the compound in this application comprising Xanifolia Y0, Y1, Y2, Y, Y5, Y7, Y8, Y9, Y10, Xanifolia (x), Escin or Aescin or a salt, ester, metabolite thereof. In an embodiment the compound may be selected from formulas (1A), (1B), (1C), (1D), (1E), (1F), (1G), (1H), (1J), (1K), (1L). In an embodiment, the compound comprises a triterpene backbone, two angeloyl groups and sugar moiety. In an embodiment the compound(s) are selected from Compound A to X and A1 to X1 in the application. In an embodiment the compound(s) are selected from Compound Z1 to Z13 in the application. In an embodiment the compound(s) are selected from ACH-Z4, ACH-Y10, ACH-Y2, ACH-Y8, ACH-Y7, ACH—Y0, ACH-X, ACH-E, ACH-Mb5 and ACHMb12. In an embodiment the saponins comprise Ba1, Ba2, Ba3, Ba4, Ba5, Ba6, Ba7, Ba8, Ba9, Ba10, Ba11, Ba12, Ba13, Ba14, Ba15, Ba16, and Ba17. In an embodiment the saponins comprise Mb1, Mb2, Mb3, Mb4, Mb5, Mb6, Mb7, Mb8, Mb9, Mb10, Mb11, Mb12, and Mb13.

In an embodiment, the methods and compositions of this application can be used for manufacturing an adjuvant vaccine, wherein the methods and compositions are used for manufacturing an adjuvant vaccine in a subject, wherein the method comprises administering to a subject or contacting the cell with the compound in this application comprising Xanifolia Y0, Y1, Y2, Y, Y5, Y7, Y8, Y9, Y10, Xanifolia (x), Escin or Aescin or a salt, ester, metabolite thereof. In an embodiment the compound may be selected from formulas (1A), (1B), (1C), (1D), (1E), (1F), (1G), (1H), (1J), (1K), (1L). In an embodiment, the compound comprises a triterpene backbone, two angeloyl groups and sugar moiety. In an embodiment the compound(s) are selected from Compound A to X and A1 to X1 in the application. In an embodiment the compound(s) are selected from Compound Z1 to Z13 in the application. In an embodiment the compound(s) are selected from ACH-Z4, ACH-Y10, ACH-Y2, ACH-Y8, ACH-Y7, ACH-Y0, ACH-X, ACH-E, ACH-Mb5 and ACH-Mb12. In an embodiment the saponins comprise Ba1, Ba2, Ba3, Ba4, Ba5, Ba6, Ba7, Ba8, Ba9, Ba10, Ba11, Ba12, Ba13, Ba14, Ba15, Ba16, and Ba17. In an embodiment the saponins comprise Mb1, Mb2, Mb3, Mb4, Mb5, Mb6, Mb7, Mb8, Mb9, Mb10, Mb11, Mb12 and Mb13. In an embodiment, this application provides an adjuvant composition comprising a saponin or compound selecting from above; wherein the composition is comprised of an immunostimulatory oligonucleotide.

In an embodiment, the methods and compositions of this application can be used for manufacture of medicament for vaccine or antiviral agent for Enterovirus comprising EV71, wherein the method comprises administering to a subject or contacting the cell with compounds selected in this application comprising Mb1, Mb2, Mb3, Mb4, Mb5, Mb6, Mb7, Mb8, Mb9, Mb10, Mb11, Mb12 and Mb13.

The composition comprises bioactive compounds from natural plants or synthesis. The majority of the plants are from the Sapindaceae family, which has 140-150 genera with 1400-2000 species. The program is based on our purification methods and biological assays including the MTT assay See International Application No. PCT/US05/31900, filed Sep. 7, 2005, U.S. Ser. No. 11/289,142, filed Nov. 28, 2005, and U.S. Ser. No. 11/131,551, filed May 17, 2005, and PCT/US2008/002086, 1188-ALA-PCT, filed Feb. 15, 2008, the contents of which are incorporated herein by reference. The details of Analysis of gene expression of ES2 cells after Y-treatment by Microarray, Data Analysis Methods and Western blot in PCT/US2008/002086, 1188-ALA-PCT, filed Feb. 15, 2008, the contents of which are incorporated herein by reference This invention provides a composition comprising an effective amount of triterpenoidal saponins named as Xanifolia Y1, Y2, Y, Y5, Y7, Y8, Y9, Y10, and Y0 or their salt or their derivatives. In an embodiment the saponins comprise Ba1, Ba2, Ba3, Ba4, Ba5, Ba6, Ba7, Ba8, Ba9, Ba10, Ba11, Ba12, Ba13, Ba14, Ba15, Ba16, and Ba17 or their salt or their derivatives. In an embodiment the saponins comprise Mb1, Mb2, Mb3, Mb4, Mb5, Mb6, Mb7, Mb8, Mb9, Mb10, Mb11, Mb12 and Mb13, or their salt or their derivatives for modulating expression or secretion of adhesion proteins, reducing expression or secretion of adhesion proteins or reducing the expression or secretion of fibronectin, for treating chronic venous insufficiency, peripheral edema, antilipemic, chronic venous disease, varicose vein disease, varicose syndrome, venous stasis, expectorant, peripheral vascular disorders, cerebro-organic convulsion, cerebral circulation disorder, cerebral edema, psychoses, dysmenorrheal, hemorrhoids, episiotomies, peripheral edema formation or postoperative swelling; for reducing symptoms of pain; for reducing symptoms of stomach pain; for reducing symptoms of leg pain; for treating pruritis, lower leg volume, thrombosis, thromophlebitis; for treating rheumatism; for preventing gastric ulcers antispasmotic; blocking the migration, metastasis of cancer cells or inhibiting tumor growth. In an embodiment the method comprises administering to a subject or contacting the cell with compounds in this application comprising Xanifolia Y0, Y1, Y2, Y, Y5, Y7, Y8, Y9, Y10, Xanifolia (x), Escin or Aescin or a salt, ester, metabolite thereof. In an embodiment the compound may be selected from formulas (1A), (1B), (1C), (1D), (1E), (1F), (1G), (1H), (1J), (1K), (1L). In an embodiment, the compound comprises a triterpene backbone, two angeloyl groups and sugar moiety. In an embodiment the compound(s) are selected from Compound A to X and A1 to X1 in the application. In an embodiment the compound(s) are selected from Compound Z1 to Z13 in the application. In an embodiment the compound(s) are selected from ACH-Z4, ACH-Y10, ACH-Y2, ACH-Y8, ACH-Y7, ACH-Y0, ACH-X, ACH-E, ACH-Mb5 and ACH-Mb12. The compounds of this invention can be isolated from natural sources or synthesized.

See experiments results in this application and see PCT/US05/31900, filed Sep. 7, 2006; U.S. Ser. No. 10/906,303, filed Feb. 14, 2005; International Application No. PCT/US04/43465, filed Dec. 23, 2004; International Application No. PCT/US04/33359, filed Oct. 8, 2004 and U.S. Ser. No. 11/131,551, filed May 17, 2005, PCT/US2007/077273, filed Aug. 30, 2007, PCT/US2008/002086, 1188-ALA-PCT, filed Feb. 15, 2008, US61/038,277 filed Mar. 20, 2008, US61/054,308, filed May 19, 2008, the contents of which are incorporated herein by reference.

Acid Hydrolysis of Saponin 15 mg Xanifolia-Y was dissolved in 1 ml of Methanol. 1 ml of 2N HCl was then added. The mixture was refluxed in 80° C. water bath for 5 hours. The solution was then neutralized by adding 2 ml of 1N NaOH (to final pH 4-6). The aglycone was then extracted with ethylacetate 3 ml×2. The extracts were collected and pooled. Further isolation of aglycone (ACH-Y) was achieved by HPLC with isocratic elution of 80-100% acetonitrile. Repeat the experiment with compound Z4, Y10, Y2, Y8, Y7, Y0, X, and ESCIN were obtained compounds ACH-Z4, ACH-Y10, ACH-Y2, ACH-Y8, ACH-Y7, ACH-Y0, ACH-X, ACH-E, ACH-Mb12, ACH-Mb5.

In mild conditions, the saponin will be partially hydrolyzed to a mixture of products. The products can be separated by HPLC. Also, specific partial hydrolysis can be achieved with enzymes. The β-glucosidase is a good enzyme for cleaving the β-glucose from saponins.

Removal of the Acyl Group by Alkaline Hydrolysis 20 mg of Xanifolia-Y was dissolved in 0.5 ml of 1M NaOH. The solution was incubated in 80° C. water bath for 4 hours. It was cooled to room temperature before neutralized with 0.5 ml 1 N HCl (adjust pH to about 3). The mixture was extracted with 2 ml 1-butanol 3 times. The butanol fractions were collected and lyophilized. The hydrolyzed saponin with further purified with HPLC in a C-18 column eluted with 25% acetonitrile.

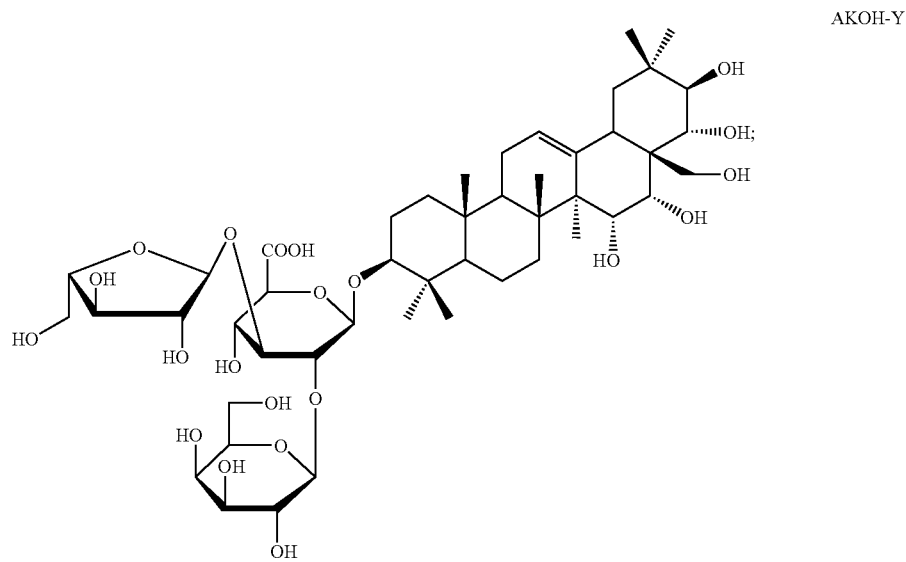

AKOH-Y

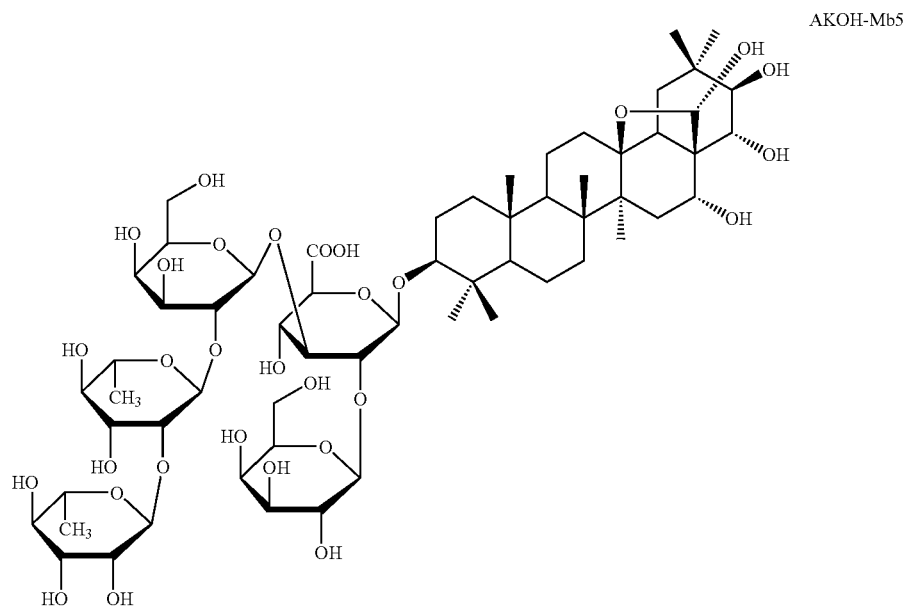

AKOH-Mb5

Compounds AKOH-Y and AKOH-Mb5 have lost anticancer activity.

This invention provides a use of compound for manufacture of medicament or a method of modulating adhesion proteins or their receptors, reducing the adhesive ability of the cancer cells, wherein the modulating comprises positive or negative regulating. In an embodiment, the adhesion proteins comprise fibronectin, integrins family, myosin, vitronectin, collagen, laminin, glycosylation cell surface proteins, polyglycans, cadherin, heparin, tenascin, CD 54, CAM, elastin and FAK. In an embodiment, the method comprises reducing the secretion of fibronectin. This invention provides a method of blocking the migration, metastasis of cancer cells or inhibiting cancer cell growth or inhibiting leishmaniases modulating adhesion or inhibiting angiogenesis of cancer tumor, antiparasitics or manufacturing an adjuvant composition comprising administering an effective amount of a pharmaceutical composition comprising a composition comprises the molecular formula or compound in this invention. The cancers comprise comprise breast cancer, leukocytic cancer, liver cancer, ovarian cancer, bladder cancer, prostatic cancer, skin cancer, bone cancer, brain cancer, leukemia cancer, lung cancer, colon cancer, CNS cancer, melanoma cancer, renal cancer, cervical cancer, esophageal cancer, testicular cancer, spleenic cancer, kidney cancer, lymphhatic cancer, pancreatic cancer, stomach cancer and thyroid cancer. The compounds of this invention can be isolated from natural sources or synthesized. In an embodiment the method comprises administering to a subject or contacting a cell with the compounds, wherein the compound is selected from the following:

(Z1) 3-O-[β-D-galactopyranosyl(1→2)]-α-L-arabinofuranosyl(1→3)-β-D-glucuronopyranosyl-21-O-angeloyl, 22-O-(2-methylpropanoyl)-3β, 15α, 16α, 21β, 22α, 28-hexahydroxyolean-12-ene;

(Z2) 3-O-[β-D-galactopyranosyl-(1→2)]-α-L-arabinofuranosyl-(1→3)β-D-glucuronopyranosyl-21-O-angeloyl-22-O-(angeloyl-2-methylbutanoyl)-3β, 15α, 16α, 21β, 22α, 28-hexahydroxyolean-12-ene;

(Z3) 3-O-[β-D-galactopyranosyl(1→2)]-α-L-arabinofuranosyl(1→3)-β-D-glucuronopyranosyl-21-O-(2-methylpropanoyl), 22-O-(2-methylpropanoyl)-3β, 15α, 16α, 21β, 22α, 28-hexahydroxyolean-12-ene;

(Z4) 3-O-[β-D-galactopyranosyl(1→2)]-α-L-arabinofuranosyl(1→3)-β-D-glucuronopyranosyl-21-O-angeloyl, 22-O-benzoyl-3β, 15α, 16α, 21β, 22α, 28-hexahydroxyolean-12-ene;

(Z5) 3-O-[β-D-galactopyranosyl(1→2)]-α-L-arabinofuranosyl(1→3)-β-D-glucuronopyranosyl-21-O-angeloyl, 22-O-angeloyl-3β, 15α, 16α, 21β, 22α, 28-hexahydroxyolean-12-ene;

(Z6) 3-O-[β-D-galactopyranosyl(1→2)]-α-L-arabinofuranosyl(1→3)-β-D-glucuronopyranosyl-21-O-(2-methylpropanoyl)-O-benzoyl, 22-O-(2-methylpropanoyl)-3β, 15α, 16α, 21β, 22α, 28-hexahydroxyolean-12-ene;

(Z7) 3-O-[β-D-galactopyranosyl(1→2)]-α-L-arabinofuranosyl(1→3)-β-D-glucuronopyranosyl-21-O-(2-methylpropanoyl)-O-angeloyl, 22-O-(2-methylbutanoyl)-3β, 15α, 16α, 21β, 22α, 28-hexahydroxyolean-12-ene;

(Z8) 3-O-[β-D-galactopyranosyl(1→2)]-α-L-arabinofuranosyl(1→3)-β-D-glucuronopyranosyl-21-O-benzoyl, 22-O-benzoyl-3β, 15α, 16α, 21β, 22α, 28-hexahydroxyolean-12-ene;

(Z9) 3-O-[β-D-galactopyranosyl(1→2)]-β-D-xylopyranosyl(1→3)-β-D-glucuronopyranosyl-21-O-angeloyl, 22-O-benzoyl-3β, 15α, 16α, 21β, 22α, 28-hexahydroxyolean-12-ene;

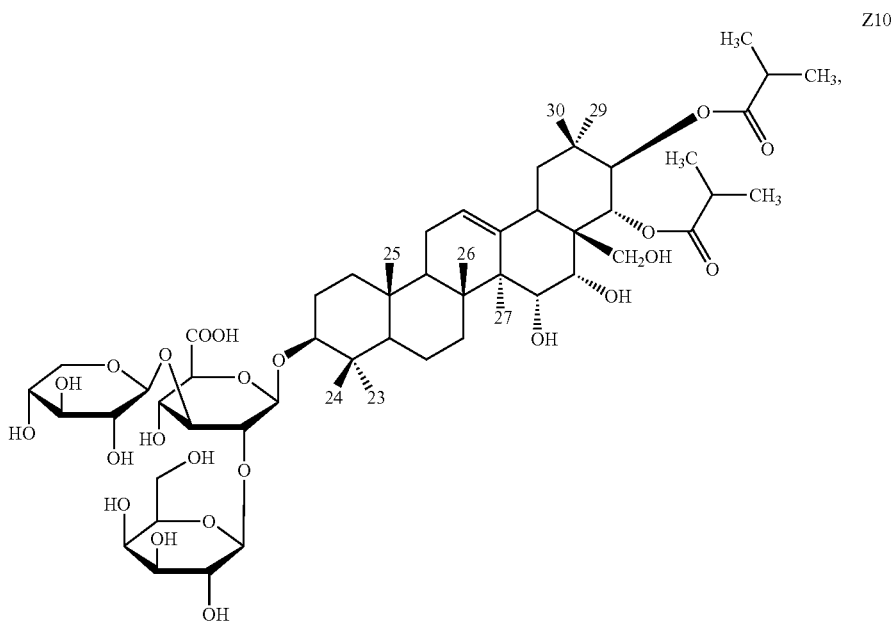

3-O-[β-D-galactopyranosyl(1→2)]-β-D-xylopyranosyl-(1→3)-β-D-glucuronopyranosyl-21-O-(2-methylpropanoyl), 22-O-(2-methylpropanoyl)-3β, 15α, 16α, 21β, 22α, 28-hexahydroxyolean-12-ene;

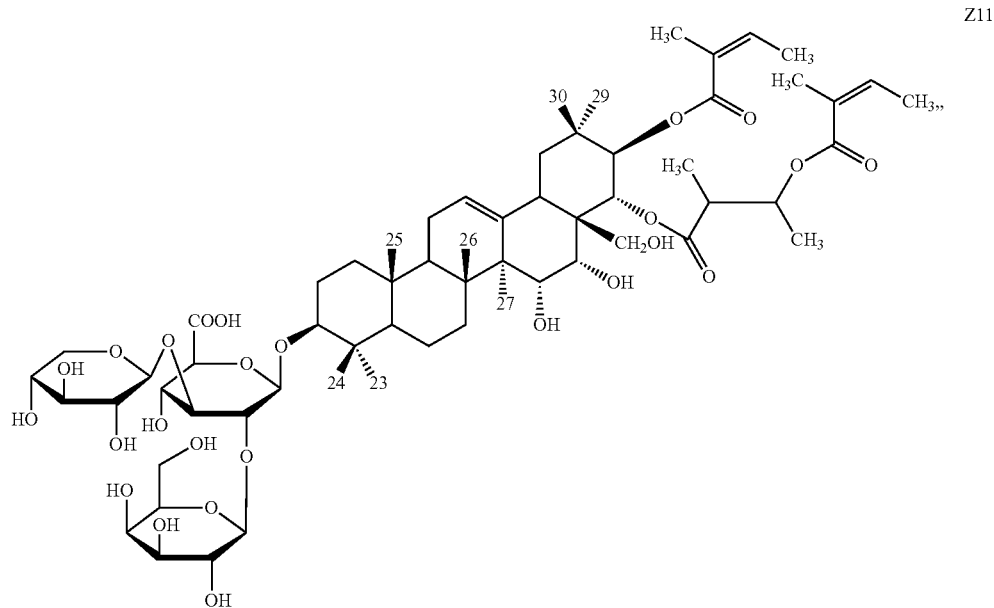

3-O-[β-D-galactopyranosyl-(1→2)]-β-D-xylopyranosyl-(1→3)β-D-1-glucuronopyranosyl-21-O-angeloyl-22-O-(angeloyl-2-methylbutanoyl)-3β, 15α, 16α, 21β, 22α, 28-hexahydroxyolean-12-ene;

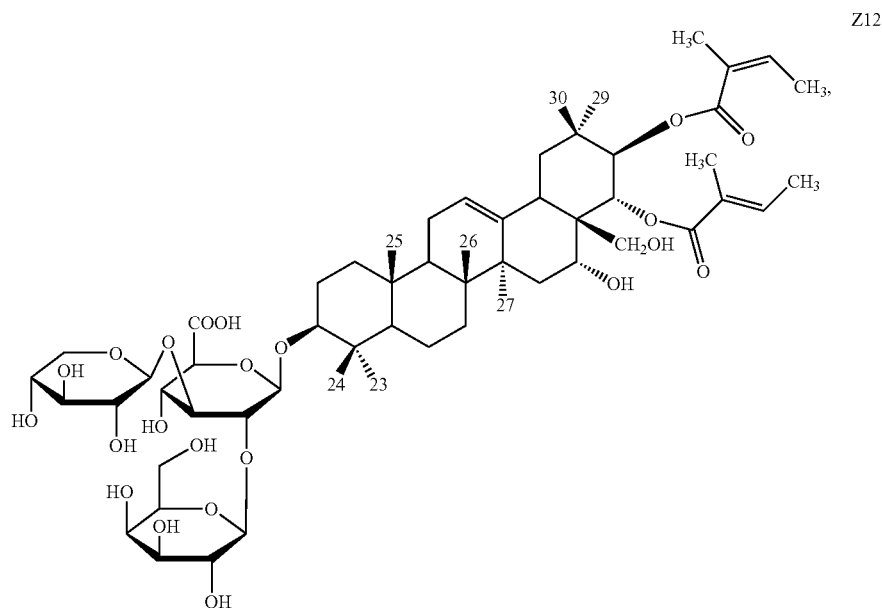

3-O-[β-D-galactopyranosyl(1→2)]-β-D-xylopyranosyl(1→3)-β-D-glucuronopyranosyl-21-O-angeloyl, 22-O-tigloyl-3β, 16α, 21β, 22α, 28-pentahydroxyolean-12-ene;

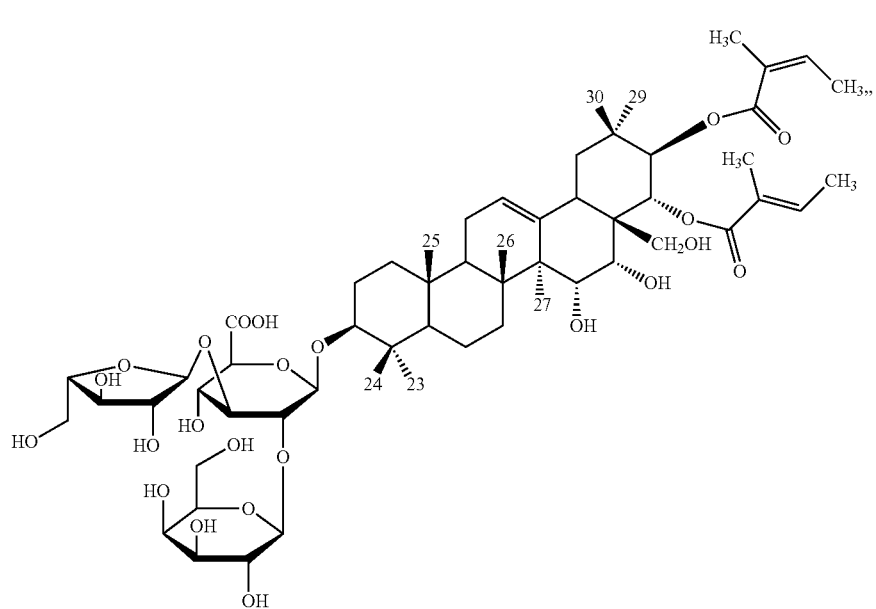

3-O-[β-D-galactopyranosyl(1→2)]-α-L-arabinofuranosyl (1→3) -β-D-glucuronopyranosyl-21-O-angeloyl, 22-O-tigloyl-3β, 15α, 16α, 21β, 22α, 28-hexahydroxyolean-12-ene;

This invention provides uses of a compound for manufacture of medicament selected from formula (1B), for modulating, regulating or interacting with the adhesion protein, wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK. In an embodiment, this invention provides a method of reducing the expression or secretion of fibronectin, modulating adhesion or angiogenesis of cancer cells, antiparasitics, enhancing an immune response, providing adjuvant activities or providing vaccine activities, inhibiting cancer metastasis or growth, using the compounds selected for the following:

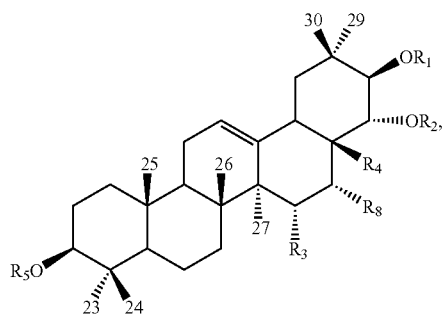

also named as (1B),
or a salt, ester, metabolite or derivative thereof, wherein R1 comprises a group selected from hydrogen, angeloyl, acetyl, tigloyl, senecioyl, alkyl, dibenzoyl, benzoyl, alkanoyl, alkenoyl, benzoyl alkyl substituted alkanoyl, acyl, aryl, heterocylic, heteroraryl, alkenylcarbonyl and derivatives thereof; R2 comprises a group selected from hydrogen, angeloyl, acetyl, tigloyl, senecioyl, alkyl, benzoyl, dibenzoyl, alkanoyl, alkenoyl, benzoyl alkyl substituted alkanoyl, aryl, acyl, heterocylic, heteroraryl, alkenylcarbonyl and derivative thereof; R4 represents $CH_2OR6$ or COOR6, wherein R6 is selected from hydrogen, angeloyl, acetyl, tigloyl, senecioyl, alkyl, benzoyl, dibenzoyl, alkanoyl, alkenoyl, benzoyl alkyl substituted alkanoyl, aryl, acyl, heterocylic, heteroraryl and derivative thereof; R3 is H or OH; wherein at least one of R1, R2, and R6 comprises a group selected from angeloyl, acetyl, tigloyl, senecioyl, benzoyl, dibenzoyl, alkanoyl, alkenoyl, benzoyl alkyl substituted alkanoyl, aryl, acyl, heterocylic, heteroraryl and derivative thereof; R5 comprises a hydrogen or sugar moiety, wherein the sugar moiety comprises at least one sugar of, but is not limited to, D-glucose, D-galactose, L-rhamnose, L-arabinose, D-xylose, alduronic acid: D-glucuronic acid, D-galacturonic acid or a derivative thereof, or the combination thereof.

In an embodiment, R1 comprises a sugar moiety wherein substituted with two groups selecting from angeloyl, acetyl, tigloyl, senecioyl, benzoyl, dibenzoyl, alkanoyl, alkenoyl, benzoyl alkyl substituted alkanoyl, aryl, acyl, heterocylic heteroraryl and a derivative thereof. In an embodiment, R1 comprises a sugar moiety wherein substituted with at least one group selecting from angeloyl, acetyl, tigloyl, senecioyl, benzoyl, dibenzoyl, alkanoyl, alkenoyl, benzoyl alkyl substituted alkanoyl, aryl, acyl, heterocylic, heteroraryl and a derivative thereof. In an embodiment, R2 comprises a sugar moiety wherein at least one group is selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic, heteroraryl and a derivative thereof. In an embodiment, R2 comprises a sugar moiety or a side chain wherein at least two groups are selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic, heteroraryl and a derivative thereof. In an embodiment, R4 comprises CH$_2$OR6 or COOR6 wherein R6 is a sugar moiety which comprises at least one group selected from angeloyl, acetyl, tigloyl, senecioyl, benzoyl, dibenzoyl, alkanoyl, alkenoyl, benzoyl alkyl substituted alkanoyl, aryl, acyl, heterocylic, heteroraryl and a derivative thereof. In an embodiment, R4 comprises CH$_2$OR6 or COOR6, wherein R6 is a sugar moiety which comprises at least two groups selected from angeloyl, acetyl, tigloyl, senecioyl, benzoyl, dibenzoyl, alkanoyl, alkenoyl, benzoyl alkyl substitutedalkanoyl, aryl, acyl, heterocylic, heteroraryl and a derivative thereof. In an embodiment, R4 comprises CH$_2$OR6 or COOR6, wherein R6 is a sugar moiety which comprises at least two groups selected from angeloyl, acetyl, tigloyl and senecioyl. In an embodiment, R4 comprises CH$_2$OR6 or COOR6 of formula (1B), at least two of R1, R2 and R6 comprise the group selected from angeloyl, acetyl, tigloyl, senecioyl, benzoyl, dibenzoyl, alkanoyl, alkenoyl, benzoyl alkyl substituted alkanoyl, aryl, acyl, heterocylic, heteroraryl and a derivative thereof. In an embodiment, R4 comprises CH$_2$OR6 or COOR6 of formula (1B), wherein at least two of R1, R2 and R6 comprise angeloyl, benzoyl, alkenoyl, or a derivative thereof. In an embodiment, R4 is a side chain comprising CH$_2$OCOCH$_3$, CH$_2$COO-alkyl, CH$_2$OH, COOH, angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl, alkanoyl substituted phenyl, alkenoyl substituted phenyl, or a derivative thereof. In a further embodiment, R5 comprises a sugar moiety, wherein the sugar moiety comprises one or more sugar of, but is not limited to glucose, galactose, rhamnose, arabinose, xylose, fucose, allose, altrose, gulose, idose, lyxose, mannose, psicose, ribose, sorbose, tagatose, talose, fructose, or alduronic acid: glucuronic acid, galacturonic acid, or derivatives thereof, or the combination thereof. In an embodiment, R5 comprises a sugar moiety or a group capable of performing the function of the sugar moiety. In an embodiment, the R5 represents H. In an embodiment, R4 represents H, OH or CH3. In an embodiment, positions C23, C24, C25, C26, C29 and C30 of the compound independently comprise CH$_3$, CH$_2$OH, CHO, COOH, COOa-lkyl, COO-aryl, COO-heterocyclic, COO-heteroaryl, CH$_2$Oaryl, CH$_2$O-heterocyclic, CH$_2$O-heteroaryl, alkyls group, acetyl group or derivatives thereof, particular CH3. In an embodiment, R1 and R2 independently comprise an angeloyl group. In an embodiment, R1 is a sugar moiety or a side chain which comprises two angeloyl groups. In an embodiment, R1 and R2 independently comprise a benzoyl group. In an embodiment, R1 is a sugar moiety which is substituted with two benzoyl groups. In an embodiment, $R_3$ represents H or OH. In an embodiment, R8 may be OH. In an embodiment, the O at C21, 22 may be replaced by NH. In an embodiment, this invention provides a method of reducing the secretion of fibronectin; wherein the medicament is for inhibiting tumor or cancer cell growth and for treating cancer, wherein the cancers comprise breast cancer, leukocytic cancer, liver cancer, ovarian cancer, bladder cancer, prostatic cancer, skin cancer, bone cancer, brain cancer, leukemia cancer, lung cancer, colon cancer, CNS cancer, melanoma cancer, renal cancer, cervical cancer, esophageal cancer, testicular cancer, spleenic cancer, kidney cancer, lymphatic cancer, pancreatic cancer, stomach cancer and thyroid cancer. Substitution, deletion and/or addition of any group in the above-described compounds by other group(s) will be apparent to one of ordinary skill in the art based on the teachings of this application. In a further embodiment, the substitution, deletion and/or addition of the group(s) in the compound of the invention does not substantially affect the biological function of the compound.

This invention provides uses, methods, processes, compounds and compositions for modulating adhesion or angiogenesis of cancer cells, antiparasitics, enhancing an immune response, providing adjuvant activities or providing vaccine activities, inhibiting cancer metastasis or growth, reducing adhesion protein of cells, wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK. In an embodiment, methods comprise inhibiting the gene expression. In an embodiment, this invention provides a method of reducing the expression or secretion of fibronectin. In an embodiment the method can block the migration, metastasis of cancer cells or inhibit the growth of cancers or anti-angiogenesis, wherein the cancers comprise breast cancer, leukocytic cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer, cervical cancer, esophageal cancer, testicular cancer, spleenic cancer, kidney cancer, lymphatic cancer, pancreatic cancer, stomach cancer and thyroid cancer, In an embodiment the compounds are anti-angiogenic, inhibit cancer cell metastasis and inhibit cancer growth. In an embodiment the compounds promote angiopoietin 2. In an embodiment the compound is selected from the following formulas (1E). In an embodiment the method comprises administering to a subject or contacting the cells with the compounds, wherein the compound is selected from the formula (1E):

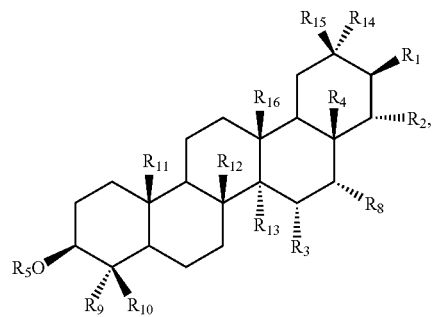

also named (1E), wherein

R1 is selected from hydrogen, hydroxyl, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof;

R2 is selected from hydrogen, hydroxyl, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof;

R4 represents CH3, CHO, CH₂R6 or CORE, wherein R6 is selected from hydroxyl, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof; R3 is H or OH; R8 is H or OH, particularly OH;

R16 is H, or R4 and R16 may together form —CH2—X—, CH(OH)—X— or C(=O)—X—, wherein the —X— may be O or NH; wherein when the C12-13 of ring 3 of the triterpene has a double bond then R16 is absent.

R5 is a hydrogen, heterocyclic or sugar moiety(ies), wherein the sugar moiety(ies) is/are selected from a group consisting of glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, and derivatives or combination thereof; wherein R9, R10, R11, R12, R13, R14, R15 are independently attached a group selecting from CH₃, CH₂OH, CHO, COOH, COO-alkyl, COO-aryl, COO-heterocyclic, COO-heteroaryl, CH₂Oaryl, CH₂O-heterocyclic, CH₂O-heteroaryl, alkyls group, hydroxyl, acetyl group, particularly CH3; or wherein R9, R10, R11, R12, R13, R14, R15 are independently attached a CH3; wherein R4 and R16 form a divalent radical of formula CH2O, CH(OR7)O, or COOR7, wherein R7 is hydrogen, alkyl, angeloyl, tigloyl, senecioyl, dibenzoyl, benzoyl, alkanoyl, alkenoyl, benzoyl alkyl substituted alkanoyl, aryl, acyl, heterocylic, heteroraryl, and derivatives thereof; wherein at least two of R1, R2 and R6 individually comprises a group selected from O-angeloyl, O-tigloyl, O-senecioyl, O-dibenzoyl, O-benzoyl, O-alkanoyl, O-alkenoyl, O-benzoyl alkyl substituted O-alkanoyl, O-aryl, O-acyl, O-heterocylic, O-heteroraryl, and derivatives thereof; or at least one of R1, R2, and R4 is a sugar moiety substituted with at least two groups selected from a group consisting of angeloyl, acetyl, tigloyl, senecioyl, benzoyl, dibenzoyl, alkanoyl, alkenoyl, benzoyl alkyl substituted alkanoyl, aryl, acyl, heterocylic, heteroraryl, and a derivative thereof; or wherein R4 is CH₂R6; wherein R1 and R2 independently consists an O-angeloyl group, or at least two of R1, R2 and R6 are O-angeloyl or at least one of R1, R2 or R6 is a sugar moiety with two O-angeloyls; wherein R5 is/are the sugar moiety(ies) selected from the following sugars and alduronic acids: glucose, galactose, rhamnose, arabinose, xylose, fucose, allose, altrose, gulose, idose, lyxose, mannose, psicose, ribose, sorbose, tagatose, talose, fructose, glucuronic acid, galacturonic acid; or their derivatives thereof, or the combination thereof; wherein the sugar preferably comprises glucuronic acid, arabinose and galactose. In an embodiment, wherein R5 is/are sugar moiety(ies) selected from a group consisting of glucose, galactose, arabinose, alduronic acid, glucuronic acid, galacturonic acid, and a derivative or combination thereof. In an embodiment, wherein R5 is 3-β-O-{[(α-L-rhamnopyranosyl-(1→2)]-α-L-rhamnopyranosyl-(1→2)-β-D-galactopyranosyl-(1→3)]-[β-D-galactopyranosyl-(1→2)]-β-D-glucuronopyranosyl)}. In an embodiment, wherein the carbon ring 3 comprises a double bond when R16 is H; wherein the double bond in carbon ring 3 is reduced when R4 and R16 form a divalent radical. In an embodiment, the compound has no sugar moiety. In an embodiment, the compound has at least 1 sugar moiety(ies). In an embodiment, the compound has at least 2 sugar moiety(ies). In an embodiment, the compound has at least 3 sugar moieties. In an embodiment, the compound has at least 4 sugar moieties. In an embodiment, the compound has at least 5 sugar moieties. In an embodiment, the number of sugar moiety(ies) at R5 is (are) 1, 2, 3, 4, or 5. In an embodiment, the sugar moieties attach at R5 or other side bonds. In an embodiment, the sugar moiety may be in the form of alduronic acid. In an embodiment, the compound is attached an acid.

In an embodiment the method comprises administering to a subject or contacting the cells with the compounds, wherein the compound is selected from the formula (1F):

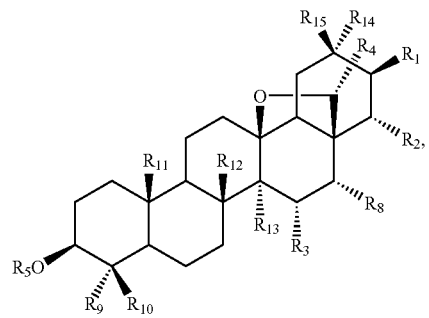

also named (1 F), wherein

R1 is selected from hydrogen, hydroxyl, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof;

R2 is selected from hydrogen, hydroxyl, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof;

R4 is selected from hydrogen, hydroxyl, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof;

R3 is H or OH; R8 is H or OH, particularly OH;

R5 is a hydrogen or sugar moiety(ies), wherein the sugar moiety(ies) is/are selected from a group consisting of glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, and derivatives or combination thereof; wherein R9, R10, R11, R12, R13, R14, R15 are independently attached a group selecting from CH₃, CH₂OH, CHO, COOH, COO-alkyl, COO-aryl, COO-heterocyclic, COO-heteroaryl, CH₂Oaryl, CH₂O-heterocyclic, CH₂O-heteroaryl, alkyls group, hydroxyl, acetyl group; or wherein R9, R10, R11, R12, R13, R14, R15 are independently attached a CH₃; wherein at least two of R1, R2 and R4 are compriseing a group selected from O-angeloyl, O-tigloyl, O-senecioyl, O-dibenzoyl, O-benzoyl, O-alkanoyl, O-alkenoyl, O-benzoyl alkyl substituted O-alkanoyl, O-aryl, O-acyl, O-heterocylic, O-heteroraryl, and derivatives thereof; or at least one of R1, R2, and R4 is a sugar moiety substituted with at least two groups selected from a group consisting of angeloyl, acetyl, tigloyl, senecioyl, benzoyl, dibenzoyl, alkanoyl, alkenoyl, benzoyl alkyl substituted alkanoyl, aryl, acyl, heterocylic, heteroraryl, and a derivative thereof; or wherein R4, R1 and R2 independently consists an O-angeloyl group, or at least two of R1, R2 and R4 are O-angeloyl or at least one of R1, R2 or R4 is a sugar moiety with two O-angeloyls; wherein R5 is/are the sugar moiety(ies) selected from the following sugars and alduronic acids: glucose, galactose, rhamnose, arabinose, xylose, fucose, allose, altrose, gulose, idose, lyxose, mannose, psicose, ribose, sorbose, tagatose, talose, fructose, glucuronic acid, galacturonic acid; or their derivatives thereof, or the combination thereof; wherein the sugar preferably comprises glucuronic acid, arabinose and galactose. In an embodiment, wherein R5 is/are sugar moiety(ies) selected from a group consisting of glucose, galactose, arabinose, alduronic acid, glucuronic acid, galacturonic acid, and a derivative or combination thereof; In an embodiment, wherein R5 is 3-β-O-{[(α-L-rhamnopyranosyl-(1→2)]-α-L-rhamnopyranosyl-(1→2)-β-D-galactopyranosyl-(1→3)]-[β-D-galactopyranosyl-(1→2)]-β-D-glucuronopyranosyl}

In an embodiment the method comprises administering to a subject or contacting the cells with the compounds of following:

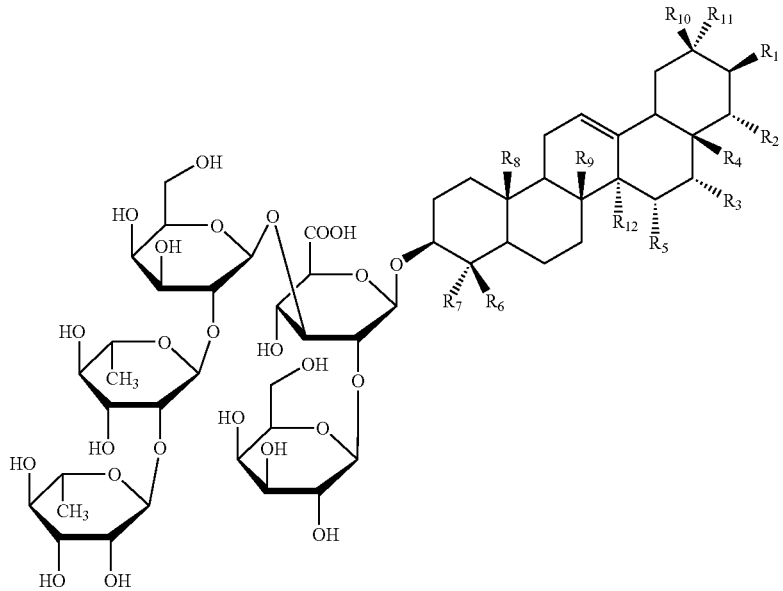

also named (1G), wherein

R1 is selected from hydrogen, hydroxyl, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof;

R2 is selected from hydrogen, hydroxyl, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof;

R4 represents CH3, CHO, CH₂R6 or CORE, wherein R6 is selected from hydroxyl, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof; R3 is H or OH; R5 is H or OH;

wherein R6, R7, R8, R9, R10, R11, R12 are independently attached a group selecting from CH₃, CH₂OH, CHO, COOH, COO-alkyl, COO-aryl, COO-heterocyclic, COO-heteroaryl, CH₂Oaryl, CH₂O-heterocyclic, CH₂O-heteroaryl, alkyls group, hydroxyl, acetyl group, particularly CH₃;

In an embodiment the method comprises administering to a subject or contacting the cells with the compounds of following:

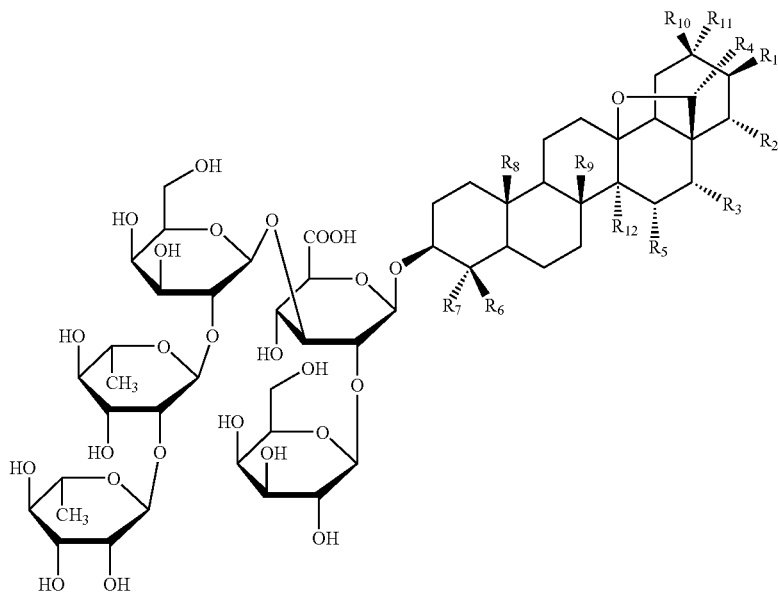

also named (1H), wherein

R1 is selected from hydrogen, hydroxyl, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof;

R2 is selected from hydrogen, hydroxyl, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof;

R4 is selected from hydroxyl, CH2OH, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof;

R3 is H or OH; R5 is H or OH; wherein R6, R7, R8, R9, R10, R11, R12 are independently attached a group selecting from $CH_3$, $CH_2OH$, CHO, COOH, COO-alkyl, COO-aryl, COO-heterocyclic, COO-heteroaryl, $CH_2O$aryl, $CH_2O$-heterocyclic, $CH_2O$-heteroaryl, alkyls group, hydroxyl, acetyl group, particularly $CH_3$;

In an embodiment the method comprises administering to a subject or contacting the cells with the compounds of following:

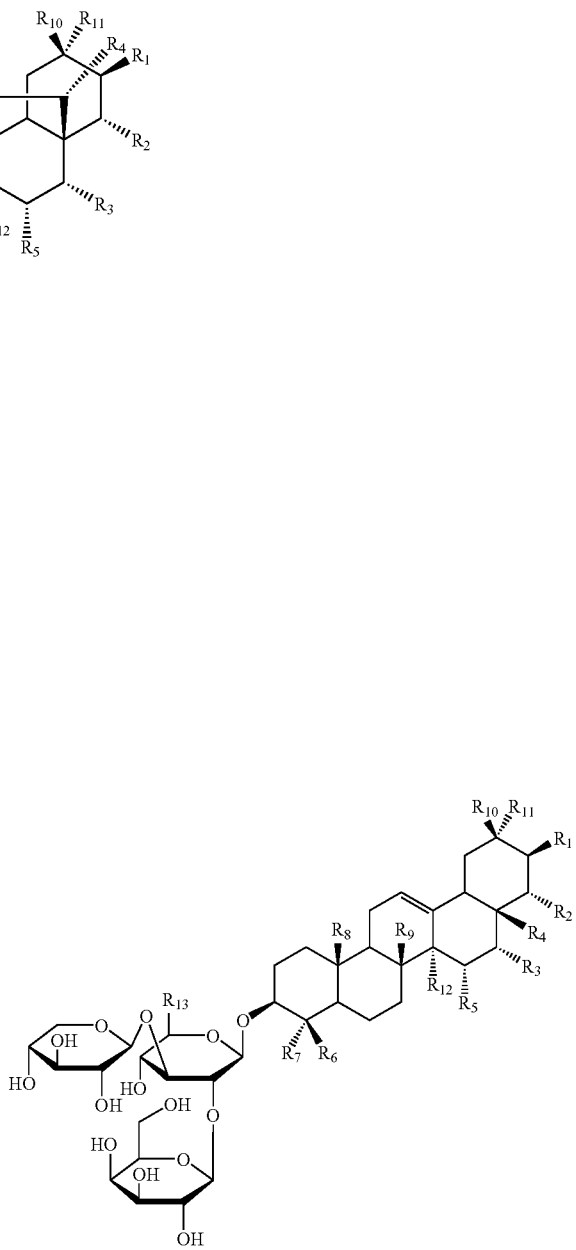

also named (1J), wherein

R1 is selected from hydrogen, hydroxyl, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof;

R2 is selected from hydrogen, hydroxyl, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof;

R4 represents CH3, CHO, $CH_2R6$ or CORE, wherein R6 is selected from hydroxyl, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenyl-carbonyl and derivatives thereof;

R3 is H or OH; R5 is H or OH, particularly OH; wherein R6, R7, R8, R9, R10, R11, R12 are independently attached a group selecting from $CH_3$, $CH_2OH$, CHO, COOH, COO-alkyl, COO-aryl, COO-heterocyclic, COO-heteroaryl, $CH_2O$aryl, $CH_2O$-heterocyclic, $CH_2O$-heteroaryl, alkyls group, hydroxyl, acetyl group, particularly $CH_3$; R13 is COOH or COO-alkyl,

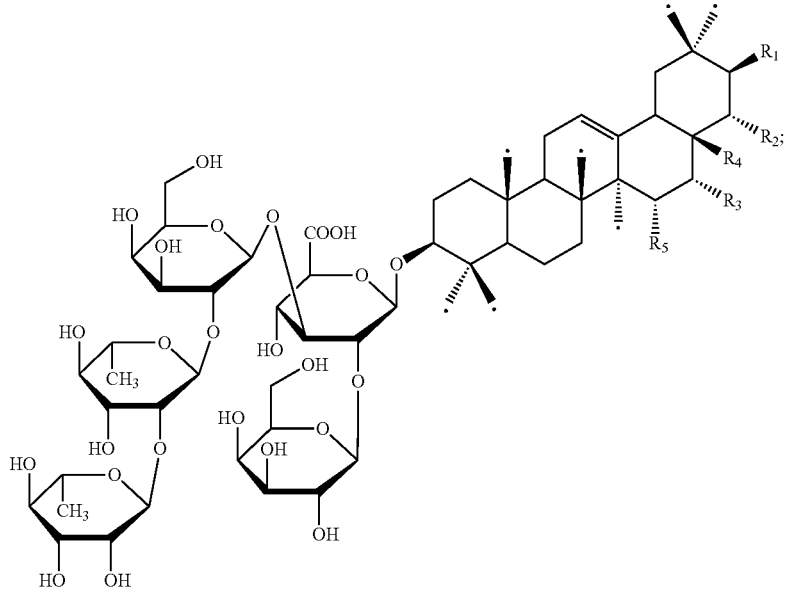

also named (1 L),
wherein R1, R2 are angeloyl, R3 is OH, R4 is CH2OH, R5 is H or OH In an embodiment the method comprises administering to a subject or contacting the cells with the compounds of following:

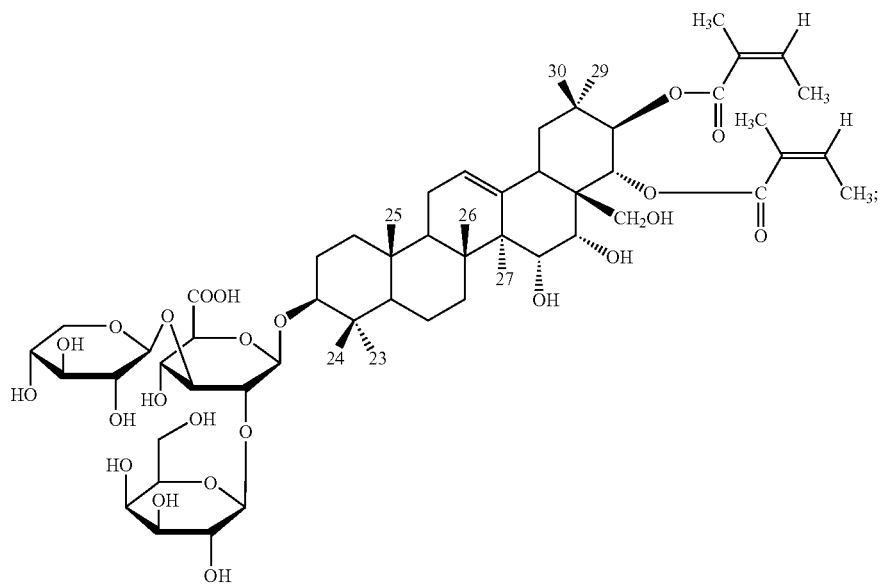

or
3-O-[β-D-galactopyranosyl(1→2)]-β-D-xyopyranosyl (1→3)-β-D-glucuronopyranosyl-21-O-angeloyl, 22-O-angeloyl-3β, 15α, 16α, 21β, 22α, 28-hexahydroxyolean-12-ene, or
3-O-[β-D-galactopyranosyl(1→2)]-β-D-xyopyranosyl (1→3)-β-D-glucuronopyranosyl-21-O-(2-methylpropanoyl)-O-angeloyl, 22-O-(2-methylbutanoyl)-3β, 15α, 16α, 21β, 22α, 28-hexahydroxyolean-12-ene,

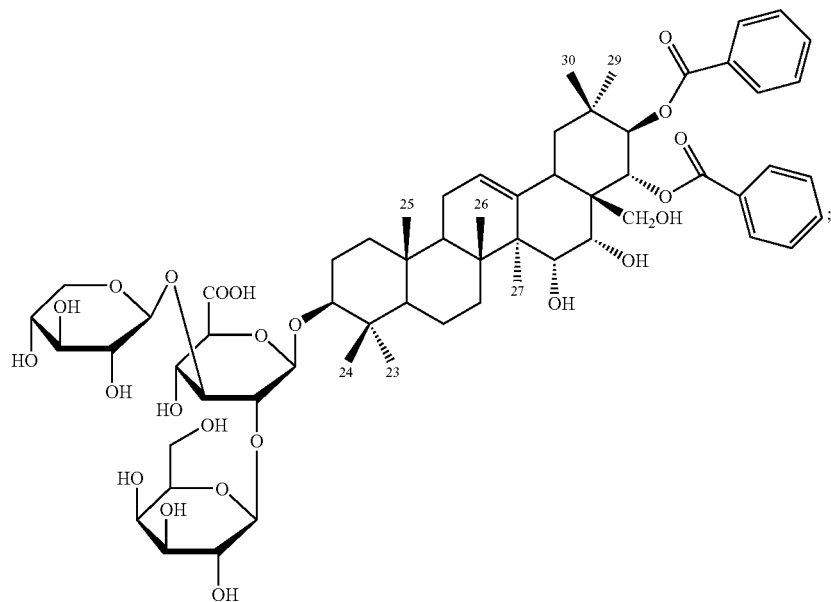

or
3-O-[β-D-galactopyranosyl(1→2)]-β-D-xyopyranosyl (1→3)-β-D-glucuronopyranosyl-21-O-benzoyl, 22-O-benzoyl-3β, 15α, 16α, 21β, 22α, 28-hexahydroxyolean-12-ene A sugar moiety is a segment of a molecule comprising one or more sugar groups. Substitution, deletion and/or addition of any group in the above-described compounds will be apparent to one of ordinary skill in the art based on the teaching of this application. In a further embodiment, the

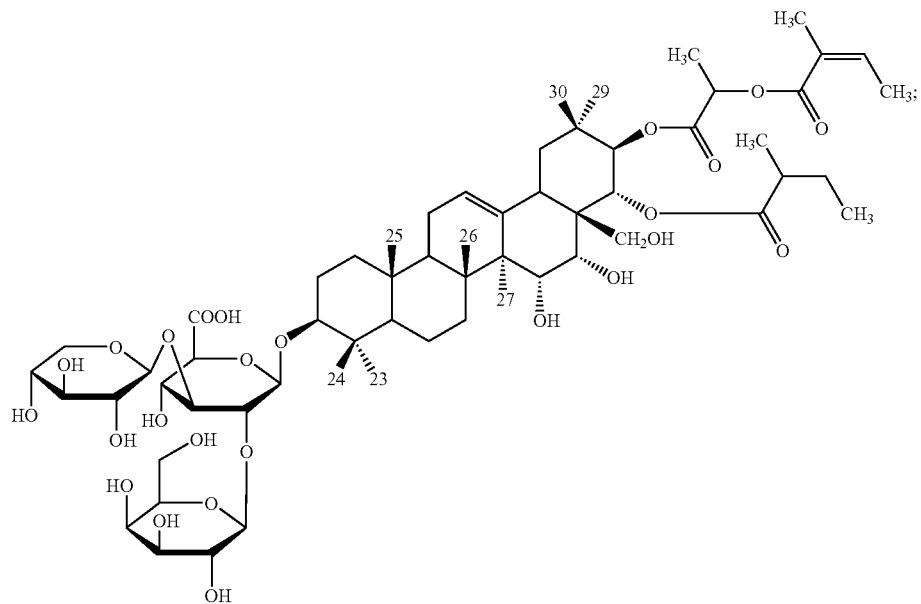

substitution, deletion and/or addition of the group(s) in the compound of the invention does not substantially affect the biological function of the compound.

This invention provides a method or a use of compound for manufacture of medicament for inhibiting venous insufficiency, particularly hemorrhoids or inhibiting leg swelling, or peripheral edema; antilipemic; for treating chronic venous disease, varicose vein disease, varicose syndrome, venous stasis, expectorant, peripheral vascular disorders, cerebro-organic convulsion, cerebral circulation disorder, cerebral edema, psychoses, dysmenorrheal, hemorrhoids, episiotomies, hamonhoids, peripheral edema formation or postoperative swelling; for reducing symptoms of pain; for reducing symptoms of stomach pain; for reducing symptoms of leg pain; for treating pruritis, lower leg volume, thrombosis, thromophlebitis; for preventing gastric ulcers antispasmotic comprising administering to a subject, in need thereof, an effective amount of the composition of any one of the above compounds or a compound comprises a triterpene which comprises any two of angeloyl, tigloyl, senecioyl, preferably two angeloyl groups, and a sugar moiety, glucose, galactose, rhamnose, arabinose, xylose, fucose, allose, altrose, gulose, idose, lyxose, mannose, psicose, ribose, sorbose, tagatose, talose, fructose, alduronic acid, glucuronic acid or galacturonic acid, or a derivative thereof, or combinations thereof, preferably selected from glucuronic acid, galacturonic acid, glucose, galactose and arabinose. The method regulates or interacts with adhesion protein, wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK. In an embodiment, the method comprises regulating the secretion of fibronectin. In an embodiment, the method comprises inhibiting leishmaniases, modulating adhesion or angiogenesis of cancer cells, antiparasitics or manufacturing an adjuvant composition. In an embodiment, antiparasitics comprise inhibiting leishmaniases, amoebiasis, trypanosomiasis, toxoplasmosis or malaria.

This invention provides a method for inhibiting the growth, migration, metastasis of cancer by altering the characteristics of membranes of cancer cell, wherein the method comprises reducing adhesion protein; wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK; wherein the method comprises inhibiting the secretion of fibronectin, wherein the methods comprises administering to a subject, in need thereof, an appropriate amount of triterpenoidal saponins comprising two or more angeloyl groups, or a compound comprising a triterpene which comprises of any two of angeloyl, tigloyl, senecioyl, perferably two angeloyl groups, and a sugar moiety, glucose, galactose, rhamnose, arabinose, xylose, fucose, allose, altrose, gulose, idose, lyxose, mannose, psicose, ribose, sorbose, tagatose, talose, fructose, alduronic acid, glucuronic acid or galacturonic acid, or a derivative thereof, or combinations thereof, preferably selected from glucuronic acid, galacturonic acid, glucose, galactose and arabinose. This invention provides a composition comprising an effective amount of the compound of any one of compound selected from the above formula or a salt, ester, metabolite or derivative thereof as a medicament for reducing expression and secretion of adhesion proteins; wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK, for inhibiting the growth, migration, metastasis of cancer, wherein the cancers comprise breast cancer, leukocytic cancer, liver cancer, ovarian cancer, bladder cancer, prostatic cancer, skin cancer, bone cancer, brain cancer, leukemia cancer, lung cancer, colon cancer, CNS cancer, melanoma cancer, renal cancer, cervical cancer, esophageal cancer, testicular cancer, spleenic cancer, kidney cancer, lymphatic cancer, pancreatic cancer, stomach cancer and thyroid cancer.

This invention also provides a composition comprising the above described compounds or their derivatives for reducing adhesion protein, wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK; wherein comprising inhibiting the secretion of fibronectin, wherein the composition is used for treating venous insufficiency, particularly hemorrhoids or inhibiting leg swelling, or peripheral edema, lipemic, chronic venous disease, varicose vein disease, varicose syndrome, venous stasis, Expectorant, peripheral vascular disorders, cerebro-organic convulsion, cerebral circulation disorder, cerebral edema, psychoses, dysmenorrheal, episiotomies, hemonhoids, peripheral edema formation or postoperative swelling; for reducing symptoms of pain; for reducing symptoms of stomach pain; for reducing symptoms of leg pain; for treating pruritis, lower leg volume, thrombosis, thromophlebitis; for preventing gastric ulcers antispasmotic, inhibiting leishmaniases; for modulating adhesion or angiogenesis of cancer cells; antiparasitics or manufacturing an adjuvant composition. In an embodiment of the above, the uses of compositions comprising any one of triterpenoid saponins with the following formula:

3-O-{[β-D-galactopyranosyl(1→2)]-[α-L-arabinofuranosyl(1→3)]-β-D-glucuronopyranoside butyl ester}-21-O-acetyl-22-O-angeloyl-3β,16α,21β,22α, 28-pentahydroxyolean-12-ene, 3-O-[β-D-galactopyranosyl(1→2)]-α-L-arabinofuranosyl(1→3) -β-D-glucuronopyranosyl-21,22-O-diangeloyl-3β, 15α, 16α, 21β, 22α, 28-hexahydroxyolean-12-ene, 3-O-[β-D-galactopyranosyl(1→2)]-α-L-arabinofuranosyl(1→3) -β-D-glucuronopyranosyl-21-O-(3,4-diangeloyl)-α-L-rhamnophyranosyl-22-O-acetyl-3β, 16α, 21β, 22α, 28-pentahydroxyolean-12-ene, 3-O-[β-D-glucopyranosyl-(1→2)]-α-L-arabinofuranosyl(1→3) -β-D-glucuronopyranosyl-21,22-O-diangeloyl-3β, 15α, 16α, 21β, 22α, 24β, 28-heptahydroxyolean-12-ene, 3-O-[β-glucopyranosyl(1→2)]-α-arabinofuranosyl(1→3)-β-glucuronopyranosyl-21,22-O-diangeloyl-3β,16α,21β, 22α,24β, 28-hexahydroxyolean-12-ene, 3-O-[β-galactopyranosyl(1→2)]-α-arabinofuranosyl(1→3)-β-glucuronopyranosyl-21-O-(3,4-diangeloyl)-α-rhamnopyranosyl-28-O-acetyl-3β, 16α, 21β, 22α, 28-pentahydroxyolean-12-ene, 3-O-[β-galactopyranosyl(1→2)]-α-arabinofuranosyl(1→3)-β-glucuronopyranosyl-21,22-O-diangeloyl-3β,16α, 21β, 22α, 28-pentahydroxyolean-12-ene, 3-O-[β-D-galactopyranosyl(1→2)]-α-L-arabinofuranosyl(1→3) -β-D-glucuronopyranosyl-21-O-angeloyl, 22-O-(2-methylpropanoyl)-3β, 15α, 16α, 21β, 22α, 28-hexahydroxyolean-12-ene, 3-O-[β-D-galactopyranosyl-(1→2)]-α-L-arabinofuranosyl-(1→3)β-D-glucuronopyranosyl-21-O-angeloyl-28-O-2-methylbutanoyl-3β, 15α, 16α, 21β, 22α, 28-hexahydroxyolean-12-ene This invention also provides a composition for regulating or reducing adhesion proteins, wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK; inhibiting venous insufficiency, particularly hemorrhoids or inhibition of leg swelling, or inhibiting cancer growth, inhibiting leishmaniases, modulating adhesion of cancer cells, modulating angiogenesis of cancer cells, antiparasitics or manufacturing an adjuvant composition, comprising any of compounds selected from the following compounds (A) to (X) and (A1) to (X1) incorporated here from PCT/US2008/002086, 1188-ALA-PCT,:

In an embodiment, a triterpene comprising the following structure has activities of reducing adhesion proteins to block the migration, inhibiting metastasis of cancer cells, inhibiting growth of cancers, inhibiting leishmaniases, modulating adhesion or angiogenesis of cancer cells, antiparasitics, or manufacturing an adjuvant composition.

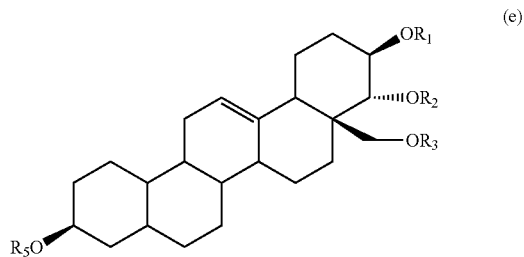

(e)

wherein at least two of R1, R2 and R3 comprise compounds selected from angeloyl, acetyl, tigloyl, senecioyl, benzoyl, dibenzoyl, alkanoyl, alkenoyl, benzoyl alkyl substituted alkanoyl, aryl, heterocylic, heteroraryl, alkanoyl substituted phenyl, alkenoyl substituted phenyl, alkenylcarbonyl or substituted with an C2-9 acid or derivative thereof. In an embodiment, at least one of R1, R2 and R3 comprise a sugar moiety comprising two compounds selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic, heteroraryl, alkanoyl substituted phenyl, alkenoyl substituted phenyl, alkenylcarbonyl or substituted with an C2-9 acid or derivative thereof. In embodiment, R1, R2 or R3 comprise angeloyl groups, tigloyl groups, senecioyl groups or acetyl group or their combinations, preferable wherein at least two of the R1, R2 and R3 comprise angeloyl groups. In an embodiment, R5 comprises sugar moiety. In an embodiment, the sugar moiety comprises at least one sugar, or glucose, or galactose, or rhamnose, or arabinose, or xylose, or alduronic acid, or glucuronic acid, or galacturonic acid, or their derivative thereof, or the combination thereof. In an embodiment, the sugar moiety comprises one or more sugar selected from, but is not limited to glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, or derivatives thereof, or the combination thereof. In an embodiment, the sugar moiety comprise glucose, galactose or arabinose, or combination thereof, or derivatives thereof. In an embodiment, the sugar moietiy comprise alduronic acids, galactose and arabinose, wherein the alduronic comprise glucuronic acid or galacturonic acid. In an embodiment, the sugar moiety comprise alduronic acids, glucose and arabinose, wherein the alduronic comprise glucuronic acid or galacturonic acid. In an embodiment, R5 is Hydrogen. In an embodiment, the R1, R2 and R3 may be attached in other position of the structure.

In an embodiment, the compound is a triterpenoid saponin comprising at least two angeloyl groups, tigloyl groups, senecioyl groups or acetyl group or their combinations, preferably with at least two angeloyl groups.

In an embodiment, at least two groups are selected from angeloyl, acetyl, tigloyl, senecioyl, benzoyl, dibenzoyl, alkanoyl, alkenoyl, benzoyl alkyl substituted alkanoyl, aryl, acyl, heterocylic, heteroraryl, alkanoyl substituted phenyl, alkenoyl substituted phenyl, alkenylcarbonyl or substituted with an C2-9 acid or derivative thereof.

In an embodiment, at least one of the side bonds of the compound comprises a sugar moiety comprising two compounds selected from angeloyl, acetyl, tigloyl, senecioyl, benzoyl, dibenzoyl, alkanoyl, alkenoyl, benzoyl alkyl substituted alkanoyl, aryl, acyl, heterocylic, heteroraryl, alkanoyl substituted phenyl, alkenoyl substituted phenyl, alkenylcarbonyl or substituted with an C2-9 acid or derivative thereof.

In an embodiment, the compound comprises a sugar moiety. In a further embodiment, the sugar moiety comprises glucose, galactose or arabinose or combination thereof.

In a further embodiment, the sugar moiety comprises at least one sugar, or glucose, or galactose, or rhamnose, or arabinose, or xylose, or alduronic acid, or glucuronic acid, or galacturonic acid, or their derivative thereof, or the combinations thereof.

In a further embodiment, the sugar moiety comprises one or more sugars selected from, but is not limited to glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, or derivatives thereof, or combinations thereof.

A composition comprises an effective amount of compound selected from the above formula or a salt, ester, metabolite or derivative thereof as a medicament for regulating or reducing adhesion protein, blocking the migration, metastasis of cancer cells, inhibiting tumor or cancer cell growth and for treating cancer, wherein the cancers comprise breast cancer, leukocytic cancer, liver cancer, ovarian cancer, bladder cancer, prostatic cancer, skin cancer, bone cancer, brain cancer, leukemia cancer, lung cancer, colon cancer, CNS cancer, melanoma cancer, renal cancer, cervical cancer, esophageal cancer, testicular cancer, spleenic cancer, kidney cancer, lymphatic cancer, pancreatic cancer, stomach cancer and thyroid cancer.

In a further embodiment, a compound or sapongenin comprising the structure (d) or (e) has anti-cancer or virus inhibiting activities.

A composition for regulating or reducing adhesion proteins, blocking the migration or metastasis of cancer cells, treating cancers or inhibiting viruses, comprises a compound, wherein the compound is a triterpene, which comprises at least two side chains which comprise angeloyl groups, wherein the side chains are at adjacent carbon in trans position. In an embodiment, the side chains are at alternate carbon in cis position. In an embodiment, the side chains are at alternate carbon in trans position. In an embodiment, the side chains are attached to an acyl. In an embodiment, the side chains are attached to an unsaturated group.

In an embodiment, the side chains are in non-adjacent carbon cis or trans position. In an embodiment, the side chains comprise a functional group capable of performing the function of angeloyl group.

The above compounds can be used for regulating or reducing adhesion proteins, blocking the migration or metastasis of cancer cells, inhibiting tumor cell growth, or reducing leg swelling, symptoms of chronic venous insufficiency, peripheral edema, antilipemic, chronic venous disease, varicose vein disease, varicose syndrome, venous stasis, expectorant, peripheral vascular disorders, by administering to a subject in need thereof, an effective amount of the above described compounds.

This invention provides a method for inhibiting tumor cell growth, regulating cell growth, reducing inflammation, inhibiting leishmaniases, modulating adhesion or angiogenesis of cancer cells, antiparasitics or manufacturing an adjuvant composition, comprising administering to a subject, in need thereof, an effective amount of the compound which comprises any of the above structures to said subject. The cancers are included but not limited to breast cancer, leukocytic cancer, liver cancer, ovarian cancer, bladder cancer, prostatic cancer, skin cancer, bone cancer, brain cancer, leukemia cancer, lung cancer, colon cancer, CNS cancer, melanoma cancer, renal cancer, cervical cancer, esophageal cancer, testicular cancer, spleenic cancer, kidney cancer, lymphatic cancer, pancreatic cancer, stomach cancer and thyroid cancer.

This invention also provides a method for reducing swelling, reducing symptoms of chronic venous insufficiency, peripheral edema, chronic venous disease, varicose vein disease, varicose syndrome, venous stasis, Expectorant, peripheral vascular disorders, cerebro-organic convulsion, cerebral circulation disorder, cerebral edema, psychoses, dysmenorrheal, hemorrhoids, episiotomies, peripheral edema formation or postoperative swelling; for reducing symptoms of leg pain; for treating pruritis, lower leg volume, for reducing symptoms of pain; thrombosis, thromophlebitis; for preventing gastric ulcers antispasmotic, antilipemic, comprising administering to a subject, in need thereof, an effective amount of the composition of this invention.

This invention provides a composition comprising the compounds provided in the invention for treating cancers; for inhibiting virus; for preventing cerebral aging; for improving memory; improving cerebral functions, for curing enuresis, frequent micturition, urinary incontinence, dementia, Alzheimer's disease, autism, brain trauma, Parkinson's disease or other diseases caused by cerebral dysfunctions; for treating arthritis, rheumatism, poor circulation, arteriosclerosis, Raynaud's syndrome, angina pectoris, cardiac disorder, coronary heart disease, headache, dizziness, kidney disorder; cerebrovascular disease; inhibiting NF-Kappa B activation; for treating brain edema, sever acute respiratory syndrome, respiratory viral diseases, chronic venous insufficiency, hypertension, chronic venous disease, hemonhoids, peripheral edema formation, varicose vein disease, flu, post traumatic edema and postoperative swelling; for inhibiting blood clot, for inhibiting ethanol absorption; for lowering blood sugar; for regulating the adrenocorticotropin and corticosterone level. This invention provides a composition for AntiMS, antianeurysm, antiasthmatic, antibradykinic, anticapillarihemorrhagic, anticephalagic, anticervicobrachialgic, antieclamptic, antiedemic, antiencaphalitic, antiepiglottitic, antiexudative, antiflu, antifracture, antigingivitic, antihematomic, antiherpetic, antihistaminic, antihydrathritic, antimeningitic, antioxidant, antiperiodontic, antiphlebitic, antipleuritic, antiraucedo, antirhinitic, antitonsilitic, antiulcer, antivaricose, antivertiginous, anti-oedematous, anti inflammatory, cancerostatic, corticosterogenic, diuretic, fungicide, hemolytic, hyaluronidase inhibitor, lymphagogue, natriuretic, pesticide, pituitary stimulant, thymolytic, vasoprotective, inhibiting leishmaniases, modulating adhesion or angiogenesis of cancer cells, antiparasitics, or manufacturing an adjuvant composition and venotonic treatment.

This invention provides a use of compounds or methods for inhibiting the expression or secretion of adhesion proteins of cancers, cancer cell migration, metastasis or growth of cancers, wherein this invention comprises a process and method for administration of the an effective amount of composition, wherein administration is by intravenous injection, intravenous drip, intraperitoneal injection or oral administration; wherein administration is by intravenous drip: 0.003-0.03 mg/kg body weight of compound dissolved in 250 ml of 10% glucose solution or in 250 ml of 0.9% NaCl solution, or by intravenous injection: 0.003-0.03 mg/kg body weight per day of compound dissolved in 10-20 ml of 10% glucose solution or of 0.9% NaCl solution, or 0.01-0.03 mg/kg body weight of compound dissolved in 250 ml of 10% glucose solution or in 250 ml of 0.9% NaCl solution, or by intravenous injection: 0.01-0.03 mg/kg body weight per day of compound dissolved in 10-20 ml of 10% glucose solution or of 0.9% NaCl solution, or 0.01-0.05 mg/kg body weight of compound dissolved in 250 ml of 10% glucose solution or in 250 ml of 0.9% NaCl solution, or by intravenous injection: 0.01-0.05 mg/kg body weight per day of compound dissolved in 10-20 ml of 10% glucose solution or of 0.9% NaCl solution, or 0.05-0.2 mg/kg body weight of compound dissolved in 250 ml of 10% glucose solution or in 250 ml of 0.9% NaCl solution, or by intravenous injection: 0.05-0.2 mg/kg body weight per day of compound dissolved in 10-20 ml of 10% glucose solution or of 0.9% NaCl solution, or by intravenous drip: 0.1-0.2 mg/kg body weight per day of compound dissolved in 250 ml of 10% glucose solution or in 250 ml of 0.9% NaCl solution, or by intravenous injection: 0.1-0.2 mg/kg body weight per day compound dissolved in 10-20 ml of 10% glucose solution or of 0.9% NaCl solution, or by intraperitoneal injection (I.P.): 2.5 mg/kg body weight per day compound dissolved in 10% glucose solution or of 0.9% NaCl solution, or by oral administration wherein the dosage of mammal is 0.01-3 mg/kg, 0.1-5 mg/kg, 1-10 mg/kg, 10-30 mg/kg, 30-60 mg/kg, or 60-90 mg/kg body weight of compound, or by intravenous injection or intravenous drip wherein the dosage of mammal is 0.01-0.1 mg/kg, 0.1-0.2 mg/kg, 0.2-0.4 mg/kg, or 0.4-0.6 mg/kg body weight of compound, or by intraperitoneal injection (I.P.) wherein the dosage of mammal is 1-3 mg/kg, 3-5 mg/kg, 4-6 mg/kg, or 6-10 mg/kg body weight of compound.

This invention provides a use of compounds or methods for inhibiting the expression or secretion of adhesion proteins of cancers, cancer cell migration, metastasis or growth of cancers, wherein the invention comprises a pharmaceutical composition comprising the compound of this invention or a pharmaceutically acceptable salt thereof, and a pharmaceutically acceptable carrier or diluent, wherein said compound is present in a concentration of 0.01 ug/ml to 65 ug/ml, or wherein said compound is present in a concentration of 0.01 ug/ml to 40 ug/ml, or wherein said compound is present in a concentration of 0.01 ug/ml to 30 ug/ml, or wherein said compound is present in a concentration of 0.01 ug/ml to 10 ug/ml, or wherein said compound is present in a concentration of 0.01 ug/ml to 5 ug/ml, or wherein said compound is present in a concentration of 5 ug/ml to 10 ug/ml, or wherein said compound is present in a concentration of 0.1 ug/ml to 5 ug/ml, or wherein said compound is present in a concentration of 0.1 ug/ml to 7.5 ug/ml, or wherein said compound is present in a concentration of 0.1 ug/ml to 10 ug/ml, or wherein said compound is present in a concentration of 0.1 ug/ml to 15 ug/ml, or wherein said compound is present in a concentration of 0.1 ug/ml to 20 ug/ml, or wherein said compound is present in a concentration of 0.1 ug/ml to 30 ug/ml, or wherein said compound is present in a concentration of 1 ug/ml to 5 ug/ml, or wherein said compound is present in a concentration of 1 ug/ml to 7.5 ug/ml, or wherein said compound is present in a concentration of 1 ug/ml to 10 ug/ml, or wherein said compound is present in a concentration of 1 ug/ml to 15 ug/ml, or wherein said compound is present in a concentration of 1 ug/ml to 20 ug/ml, or wherein said compound is present in a concentration of 1 ug/ml to 30 ug/ml, or wherein said compound is present in a concentration of 3 ug/ml to 5 ug/ml, or wherein said compound is present in a concentration of 3 ug/ml to 7.5 ug/ml, or wherein said compound is present in a concentration of 3 ug/ml to 10 ug/ml, or wherein said compound is present in a concentration of 3 ug/ml to 15 ug/ml, or wherein said compound is present in a concentration of 3 ug/ml to 20 ug/ml, or wherein said compound is present in a concentration of 3 ug/ml to 30 ug/ml, or wherein said compound is present in a concentration of 4 ug/ml to 5 ug/ml, or wherein said compound is present in a concentration of 4 ug/ml to 7.5 ug/ml, or wherein said compound is present in a concentration of 4 ug/ml to 10 ug/ml, or wherein said compound is present in a concentration of 4 ug/ml to 15 ug/ml, or wherein said compound is present in a concentration of 4 ug/ml to 20 ug/ml, or wherein said compound is present in a concentration of 4 ug/ml to 30 ug/ml, or wherein said compound is present in a concentration of 5 ug/ml to 8 ug/ml, or wherein said compound is present in a concentration of 5 ug/ml to 9 ug/ml, or wherein said compound is present in a concentration of 5 ug/ml to 10 ug/ml, or wherein said compound is present in a concentration of 5 ug/ml to 15 ug/ml, or wherein said compound is present in a concentration of 5 ug/ml to 20 ug/ml, or wherein said compound is present in a concentration of 5 ug/ml to 30 ug/ml, or wherein said compound is present in a concentration of 7 ug/ml to 8 ug/ml, or wherein said compound is present in a concentration of 7 ug/ml to 9 ug/ml, or wherein said compound is present in a concentration of 7 ug/ml to 10 ug/ml, or wherein said compound is present in a concentration of 7 ug/ml to 15 ug/ml, or wherein said compound is present in a concentration of 7 ug/ml to 20 ug/ml, or wherein said compound is present in a concentration of 7 ug/ml to 30 ug/ml.

This invention provides a use of compounds or methods for inhibiting the expression or secretion of adhesion proteins of cancers, cancer cell migration, metastasis or growth of cancers, wherein the invention comprises a pharmaceutical composition comprising the compound of this invention or a pharmaceutically acceptable salt thereof, and a pharmaceutically acceptable carrier or diluent, wherein said compound is present in a concentration of 0.008 uM to 80 uM, or wherein said compound is present in a concentration of 0.01 uM to 60 uM, or wherein said compound is present in a concentration of 0.01 uM to 50 uM, or wherein said compound is present in a concentration of 0.01 uM to 40 uM, or wherein said compound is present in a concentration of 0.01 uM to 30 uM, or wherein said compound is present in a concentration of 0.01 uM to 20 uM, or wherein said compound is present in a concentration of 0.01 uM to 10 uM, or wherein said compound is present in a concentration of 5 uM to 10 uM, or wherein said compound is present in a concentration of 0.1 uM to 5 uM, or wherein said compound is present in a concentration of 0.1 uM to 7.5 uM, or wherein said compound is present in a concentration of 0.1 uM to 10 uM, or wherein said compound is present in a concentration of 0.1 uM to 15 uM, or wherein said compound is present in a concentration of 0.1 uM to 20 uM, or wherein said compound is present in a concentration of 0.1 uM to 30 uM or wherein said compound is present in a concentration of 0.1 uM to 40 uM, or wherein said compound is present in a concentration of 0.1 uM to 50 uM or wherein said compound is present in a concentration of 0.1 uM to 60 uM, or wherein said compound is present in a concentration of 0.1 uM to 80 uM, or wherein said compound is present in a concentration of 1 uM to 5 uM, or wherein said compound is present in a concentration of 1 uM to 7.5 uM, or wherein said compound is present in a concentration of 1 uM to 10 uM, or wherein said compound is present in a concentration of 1 uM to 15 uM, or wherein said compound is present in a concentration of 1 uM to 20 uM, or wherein said compound is present in a concentration of 1 uM to 30 uM or wherein said compound is present in a concentration of 1 uM to 40 uM, or wherein said compound is present in a concentration of 1 uM to 50 uM or wherein said compound is present in a concentration of 1 uM to 60 uM, or wherein said compound is present in a concentration of 1 uM to 80 uM, or wherein said compound is present in a concentration of 3 uM to 5 uM, or wherein said compound is present in a concentration of 3 uM to 7.5 uM, or wherein said compound is present in a concentration of 3 uM to 10 uM, or wherein said compound is present in a concentration of 3 uM to 15 uM, or wherein said compound is present in a concentration of 3 uM to 20 uM, or wherein said compound is present in a concentration of 3 uM to 30 uM or wherein said compound is present in a concentration of 3 uM to 40 uM, or wherein said compound is present in a concentration of 3 uM to 50 uM or wherein said compound is present in a concentration of 3 uM to 60 uM, or wherein said compound is present in a concentration of 3 uM to 80 uM, or wherein said compound is present in a concentration of 5 uM to 8 uM, or wherein said compound is present in a concentration of 5 uM to 10 uM, or wherein said compound is present in a concentration of 5 uM to 15 uM, or wherein said compound is present in a concentration of 5 uM to 20 uM, or wherein said compound is present in a concentration of 5 uM to 30 uM or wherein said compound is present in a concentration of 5 uM to 40 uM, or wherein said compound is present in a concentration of 5 uM to 50 uM or wherein said compound is present in a concentration of 5 uM to 60 uM, or wherein said compound is present in a concentration of 5 uM to 80 uM or wherein said compound is present in a concentration of 7 uM to 8 uM, or wherein said compound is present in a concentration of 7 uM to 10 uM, or wherein said compound is present in a concentration of 7 uM to 15 uM, or wherein said compound is present in a concentration of 7 uM to 20 uM, or wherein said compound is present in a concentration of 7 uM to 30 uM or wherein said compound is present in a concentration of 7 uM to 40 uM, or wherein said compound is present in a concentration of 7 uM to 50 uM or wherein said compound is present in a concentration of 7 uM to 60 uM, or wherein said compound is present in a concentration of 7 uM to 80 uM.

Alkenyl means unsaturated linear or branched structures and combinations thereof, having 1-7 carbon atoms, one or more double bonds therein. Non-limiting examples of alkenyl groups include vinyl, propenyl, isopropenyl, butenyl, s- and t-butenyl, pentenyl, hexenyl, butadienyl, pentadienyl, and hexadienyl.

An aryl is a functional group of organic molecule derived from an aromatic compound such as benzene, a 6-14 membered carbocyclic aromatic ring system cpmprising 1-3 benzene rings. If two or more aromatic rings are present, then the rings are fused together, so that adjacent rings share a common bond. Examples include phenyl and naphthyl. The aryl group may be substituted with one or more sunstitutes independnetly selected from halogen, alkyl or alkoxy.

Acyl is a functional group obtained from an organic acid by the removal of the carboxyl. Acyl groups can be written as having the general formula —COR, where there is a double bond between the carbon and oxygen. The names of acyl groups typically end in -yl, such as formyl, acetyl, propionyl, butyryl and benzoyl.

Benzoyl is one of acyls, $C_6H_5COR$, obtained from benzoic acid by the removal of the carboxyl.

Heterocyclic compound—a compound containing a heterocyclic ring which refers to a non-aromatic ring having 1-4 heteroatoms said ring being isolated or fused to a second ring selected from 3- to 7-membered alicyclic ring containing 0-4 heteroatoms, aryl and heteroaryl, wherein said heterocyclic comprises pyrrolidinyl, pipyrazinyl, morpholinyl, trahydrofuranyl, imidazolinyl, thiomorpholinyl, and the like.

Heterocyclyl groups derived from heteroarenes by removal of a hydrogen atom from any ring atom.

Alkanoyl is the general name for an organic functional group RCO—, where R represents hydrogen or an alkyl group. Preferably alkanoyl is selected from acetyl, propionoyl, butyryl, isobutyryl, pentanoyl and hexanoyl.

Alkenoyl is alkenylcarbonyl in which alkenyl is defined above. Examples are pentenoyl(tigloyl) and hexenoyl(angeloyl).

Alkyl is a radical containing only carbon and hydrogen atoms arranged in a chain, branched, cyclic or bicyclic structure or their combinations, having 1-18 carbon atoms. Examples include but are not limited to methyl, ethyl, propyl isopropyl, butyl, s- and t-butyl, pentyl, hexyl, heptyl, octyl, nonyl, undecyl, dodecyl, tridecyl, tetradecyl, pentadecyl, cyclopropyl, cyclobutyl, cyclopentyl and cyclohexyl.

Benzoyl alkyl substituted alkanoyl is refer to straight or branched C1-C6 alkanoyl substituted with at least one benzoyl and at least one alkyl, wherein the benzoyl is attached to a straight or branched C1-C6 alkyl. Preferably a benzoyl alkyl substituted alkanoyl is benzoyl methyl isobutanoyl.

A sugar moiety is a segment of molecule comprising one or more sugars or derivatives thereof or alduronic acid thereof.

Isobutyryl is Synonym of 2-Methylpropanoyl (Y)Y3, Y and Y3 represent the same compound.

YM and (ACH-Y) represent the same compound.

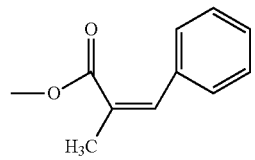

(Z)-O (C═O) C(CH3)═CH—C6H5 is an example of [O—C4 alkenoyl substituted with phenyl]

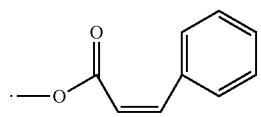

(Z)-O (C═O) C(CH3)═CH—C6H5 is an example of [O—C4 alkenoyl substituted with phenyl]

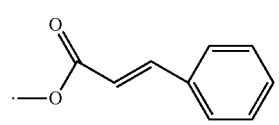

(E)-O (C═O) CH═CH—C6H5 is an example of [O—C3 alkenoyl substituted with phenyl]

-continued

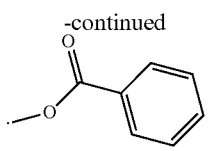

O(C═O)C6H5, Benzoyl is an example of [O—C1 alkanoyl substituted with phenyl]

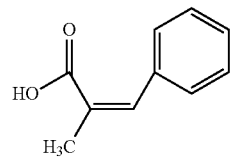

(2Z)-2-methyl-3-phenylacrylic acid

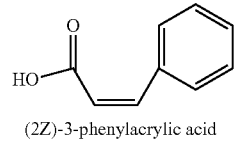

(2Z)-3-phenylacrylic acid

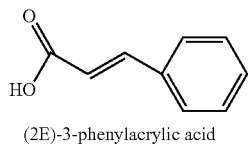

(2E)-3-phenylacrylic acid

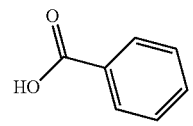

Benzoic acid

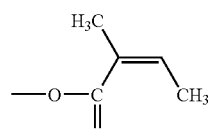

O—Angeloyl:
O(C═O)C(CH3)═CH(CH3)

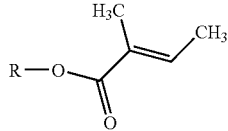

R—O—Tigloyl: O(C═O)C(CH3)═CH(CH3)

This invention provides a method of altering the characteristic of cancer cell membrane to block the migration, metastasis of cancer cells or inhibit the growth of cancers or anti-angiogenesis.

This invention provides a composition and method for inhibiting the growth, migration, metastasis of cancer by altering the adhesion characteristic of membrane of cancer cell, wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer or cervix cancer, wherein the method comprises administering to a subject or contacting the cells with Xanifolia Y0, Y1, Y2, Y, Y5, Y7, Y8, Y9, Y10, or a salt, ester, metabolite thereof. In an embodiment the method comprises administering to a subject or contacting the cells with the compound selected from formula in this application.

This application shows Xanifolia-Y is an alternate or supplemental agent to DNA-inhibition or microtubule-targeting drugs. It could be beneficial if it is used singly or in combination with other drugs of different mechanisms (block M-phase progression or DNA synthesis). Our inventions show combined effect of Xanifolia-Y and paclitaxel on inhibition of ES2 cells' growth (Detail in Experiment 14 U.S. Ser. Nos. 11/683,198, filed on Mar. 7, 2007).

Identify the binding target of Xanifolia-Y of adhesion proteins and signaling proteins in ovarian cancer cells.

In our animal studies, it was shown that Xanifolia-Y extended the life span of tumor bearing mice. (Reference Experiments 7, 8, 9 in U.S. Ser. Nos. 11/683,198, filed on Mar. 7, 2007,). The animals died sooner if the treatment of Xanifolia-Y was delayed (comparing results of treatments started from 1, 4 or 10 days after tumor inoculation). The results show that Xanifolia-Y inhibits migration or metastasis of the inoculated cancer cells. Ovarian carcinoma cells express high levels of adhesion molecules. Adhesion proteins are present in both cancer cells and mesothelial cells. While the lost of adhesion blocks of the protein accessibility due to a result of modulating by Xanifolia-Y, In an embodiment, the interaction of Xanifolia-Y with membrane alter the adhesion protein's binding site(s).

Fibronectin is a kind of glycoprotein that binds to membrane spanning receptor proteins comprising the integrins, collagen, fibrin and heparin sulfate. Fibronectin has been implicated in tumor development and metastasis. This application provides methods and compositions for modulating the gene expression of fibronectin, inhibiting the secretion of fibronectin, reducing the receptors of fibronectin, reducing the adhesion ability fibronectin, inhibiting the metastasis, or inhibiting cancer growth, wherein the method and composition comprises administering to the said subject as effective amount of compounds selected in this application.

Angiogenesis is a process involving the growth of new blood vessels. It is a normal process in growth and development. However, this is also a fundamental step in the transition of tumors from a dormant state to a malignant state. The angiopoietins are protein growth factors that modulate angiogenesis. The identified angiopoietins comprise angiopoietin 1, angiopoietin 2, angiopoietin 3, angiopoietin 4, angiopoietin 5, angiopoietin 6, angiopoietin 7, angiopoietin-like 1, angiopoietin-like 2, angiopoietin-like 3, angiopoietin-like 4, angiopoietin-like 5, angiopoietin-like 6, and angiopoietin-like 7. In an embodiment, the angiopoietin 1 is a positive foctor to promote the new blood vessels. In embodiment, the angiopoietin 2 is antagonist of angiopoietin 1, which is a negative factor for the growth of new blood vessels. This application provides methods and compositions for modulating angiopoietin and inhibiting cancer growth; wherein the cancers comprise breast, leukocyte, liver, ovarian, bladder, prostate, skin, bone, brain, leukemia, lung, colon, CNS, melanoma, renal and cervix cancer, wherein the methods and compositions comprise administering to the said subject as effective amount of compounds selected in this appliaction. The compounds in this application are positive regulating angiopoietin 2. The compounds in this application are negative regulating the angiopoietin 1. The results of the micro array experiment showed that compound Y and YM (ACH-Y) modulate the gene expression of angiopoietin family in ES2 cells. They promote angiopoietin 2 and inhibit angiopoietin 1 and angiopoietin-like 1 and angiopoietin-like 4.

The compounds in this application are used antiparasitics, enhancing an immune response, providing adjuvant activities or providing vaccine activities, anti-angiogenesis, inhibiting cancer cell metastasis and inhibiting cancer growth, wherein the compounds comprise Xanifolia Y0, Y1, Y2, Y, Y7, Y8, Y9, Y10, ACH-Y or a salt, ester, metabolite thereof and compounds selected from formula (1A), (1B), (1C), (1D), (1E), (1F), (1G), (1H), (1J), (1K), (1L). In an embodiment the method is administering contacting the compound in this application comprising Xanifolia Y0, Y1, Y2, Y, Y7, Y8, Y9, Y10, Xanifolia (x), Escin or Aescin or a salt, ester, metabolite thereof. In an embodiment the compound may be selected from formulas (1A), (1B), (1C), (1D) (1E), (1F), (1G), (1H), (1J), (1K), (1L). In an embodiment, the compound comprises a triterpene backbone, two angeloyl groups and sugar moiety. In an embodiment the compound(s) are selected from Compound A to X and A1 to X1 in the application. In an embodiment the compound(s) are selected from Compound Z1 to Z7 in the application. In an embodiment the compound(s) are selected from ACH-Z4, ACH-Y10, ACH-Y2, ACH-Y8, ACH-Y7, ACH-Y0, ACH-X, ACH-E. In an embodiment the saponins comprise Ba1, Ba2, Ba3, Ba4, Ba5, Ba6, Ba7, Ba8, Ba9, Ba10, Ba11, Ba12, Ba13, Ba14, Ba15, Ba16, Ba 17.

The triterpene compounds of this invention can be administered to a subject in need thereof treating the subject, wherein including preventing cancer or has adjuvant effect to the subject, or inhibiting the initiation or promotion of cancer, or killing the cancer/tumor cells. In an embodiment the compounds inhibit the activation of nuclear factor-kB, wherein inhibiting the localization or wherein binding the DNA. In an embodiment the compounds induce apoptosis in cancer cells.

The triterpene compounds of this invention can reduce blood vessel in the tumor in a subject. (FIG. 1)

Table 1 to 12, Effect of Y and YM on gene expression (Table of 1 to 12 PCT/US2008/002086, 1188-ALA-PCT, filed Feb. 15, 2008 are incorporated herein by reference)

TABLE 13

Effects of Y and YM on Glypican expression in ES2 cells

| Probe Set ID | Y/D | Ym/D | Gene.Symbol | Gene.Title |
| --- | --- | --- | --- | --- |
| 243865_x_at | −2.7 | −2.0 | GPC6 | Glypican 6 |
| 227059_at | −2.2 | −1.8 | GPC6 | Glypican 6 |

The results of the micro array experiment showed that compound Y and Ym inhibit gene expression of Glypican in ES2 cells.

TABLE 14

Effects of Y and YM on regulator of G-protein expression in ES2 cells

| Probe Set ID | Y/D | Ym/D | Gene.Symbol | Gene.Title |
| --- | --- | --- | --- | --- |
| 204339_s_at | −3.5 | −1.2 | RGS4 | regulator of G-protein signalling 4 |
| 204337_at | −3.4 | −1.1 | RGS4 | regulator of G-protein signalling 4 |

TABLE 14-continued

Effects of Y and YM on regulator of G-protein expression in ES2 cells

| Probe Set ID | Y/D | Ym/D | Gene.Symbol | Gene.Title |
|---|---|---|---|---|
| 204338_s_at | −2.5 | −1.1 | RGS4 | regulator of G-protein signalling 4 |

The results of the micro array experiment showed that compound Y and YM inhibit gene expression of G-protein in ES2 cells

TABLE 15

Effects of Y and YM on thrombospondin in ES2 cells

| Probe Set ID | Y/D | Ym/D | Gene.Symbol | Gene.Title |
|---|---|---|---|---|
| 201109_s_at | −2.0 | −6.2 | THBS1 | thrombospondin 1 |
| 201110_s_at | −1.8 | −4.5 | THBS1 | thrombospondin 1 |
| 201108_s_at | −1.7 | −2.2 | THBS1 | thrombospondin 1 |

The results of the micro array experiment showed that compound Y and YM inhibit gene expression of thrombospondin in ES2 cells

TABLE 16

Effects of Y and YM on insulin-like growth factor binding protein expression in ES2 cells

| Probe Set ID | Y/D | YM/D | Gene.Symbol | Gene.Title |
|---|---|---|---|---|
| 210095_s_at | −4.0 | −3.5 | IGFBP3 | insulin-like growth factor binding protein 3 |
| 212143_s_at | −3.7 | −5.3 | IGFBP3 | insulin-like growth factor binding protein 3 |
| 201508_at | −1.7 | −2.4 | IGFBP4 | insulin-like growth factor binding protein 4 |
| 205302_at | −1.7 | −1.8 | IGFBP1 | insulin-like growth factor binding protein 1 |
| 201163_s_at | −1.4 | −2.7 | IGFBP7 | insulin-like growth factor binding protein 7 |
| 203851_at | −1.3 | −1.8 | IGFBP6 | insulin-like growth factor binding protein 6 |

The results of the micro array experiment showed that compound Y and YM inhibit gene expression of insulin-like growth factor binding protein in ES2 cells.

TABLE 17

Effects of Y and YM on RAB$_3$B, member RAS oncogene family protein expression in ES2 cells

| ID | Y/D | YM/D | Gene.Symbol | Gene.Title |
|---|---|---|---|---|
| 242629_at | −3.5 | −1.8 | RAB3B | RAB3B, member RAS oncogene family |
| 205924_at | −1.7 | −1.8 | RAB3B | RAB3B, member RAS oncogene family |
| 227123_at | −1.6 | −1.2 | RAB3B | RAB3B, member RAS oncogene family |
| 205925_s_at | −1.2 | −1.2 | RAB3B | RAB3B, member RAS oncogene family |

The results of the micro array experiment showed that compound Y and Ym inhibit gene expression of RAB3B, member RAS oncogene family protein in ES2 cells.

TABLE 18

Effects of Y and YM on potassium channel, subfamily U, protein expression in ES2 cells

| ID | Y/D | YM/D | Gene.Symbol | Gene.Title |
|---|---|---|---|---|
| 237273_at | −4.0 | −1.9 | KCNU1 | potassium channel, subfamily U, member 1 |

The results of the micro array experiment showed that compound Y and Ym inhibit gene expression of family protein relate to potassium channel in ES2 cells.

TABLE 19

Effects of Y and YM on phosphatase, protein expression in ES2 cells

| 37028_at | 2.4 | 5.6 | PPP1R15A | protein phosphatase 1, regulatory (inhibitor) subunit 15A |
|---|---|---|---|---|
| 202014_at | 2.6 | 6.2 | PPP1R15A | protein phosphatase 1, regulatory (inhibitor) subunit 15A |
| 215501_s_at | 3.2 | 7.1 | DUSP10 | dual specificity phosphatase 10 |
| 221563_at | 3.8 | 5.7 | DUSP10 | dual specificity phosphatase 10 |

The results of the micro array experiment showed that compound Y and Ym stimulate gene expression of family protein relate to phosphatase.

Fibronectin Secretion Studies Summary:

Reduction of Fibronectin secretion from ES2 cells after xanifolia-Y treatment.

(Results of F1, F3, F4, F5, F7, F8, F11, F12A, F15, F16, F17) Data in PCT/US2008/002086, 1188-ALA-PCT, filed Feb. 15, 2008 are incorporated herein by reference (F11) For lung carcinoma cells (H460), at concentration of 20 ug/ml, there are inhibitions of Fibronectin secretion ranged from 20-60%.

(F12A) For bladder carcinoma cells (HTB-9), Xanifolia-Y (10 ug/ml) inhibits 50% of Fibronectin secretion.

(F15) In liver HepG2 cells. 10 ug/ml of xanifolia-Y inhibits 42% secretion of Fibronectin.

(F16) Incubation of brain glioblastoma T98G cells with 10 ug/ml of xanifolia-Y inhibits 27% Fibronectin secretion and with 20 ug/ml Y inhibits 74% Fibronectin secretion.

(F17) For skin SK-MeI-5 cells, the inhibition is 40-57% with 20 ug/ml of Xanifolia-Y.

Studies of xanifolia-Y analogs and other saponin on Fibronectin secretion from ES2 cells. Results of (F 23, F21, F13, F14, F24, F25, 26, 31B, F27,29, F28, 30, F 31, 32, F 33, F20) in PCT/US2008/002086, 1188-ALA-PCT, filed Feb. 15, 2008)

| ES2 cells | β-ES-10 | X-10 | Y0-10 | Y1-10 | Y3-10 | Y7-10 | ACH-Y-20 | AKOH-80 |
|---|---|---|---|---|---|---|---|---|
| % inhibition | 19 | 39 | 34 | 41 | 47 | 34 | 48 | No effect |

Studies of Other Saponins on Fibronectin Secretion from ES2 and Other Cells

| ES2 cells | | | | | | |
|---|---|---|---|---|---|---|
| | Mb12-10 | Mb5-10 | ACH-Mb5-10 | Ba1-10 | Ba4-10 | AKOH-Mb-40 |
| % inhibition | 30 | 35 | 30 | 30 | 28 | No effect |

| Liver | | | | | |
|---|---|---|---|---|---|
| HepG2 | Mb12-10 | Mb5-10 | ACH-Mb5-10 | Ba1-10 | Ba4-10 |
| % inhibition | 30 | 35 | 25 | 33 | 28 |

| Lung | | | | | |
|---|---|---|---|---|---|
| H460 | Mb12-10 | Mb5-10 | ACH-Mb5-10 | Ba1-10 | Ba4-10 |
| % inhibition | 20 | 25 | 22 | 19 | 18 |

| Bladder | | | | | |
|---|---|---|---|---|---|
| HTB-9 | Mb12-10 | Mb5-10 | ACH-Mb5-10 | Ba1-10 | Ba4-10 |
| % inhibition | 32 | 28 | 30 | 25 | 30 |

| Brain | | | | | |
|---|---|---|---|---|---|
| T98G | Mb12-10 | Mb5-10 | ACH-Mb5-10 | Ba1-10 | Ba4-10 |
| % inhibition | 40 | 33 | 35 | 26 | 24 |

| Skin | | | | | |
|---|---|---|---|---|---|
| SK-MEL-5 | Mb12-10 | Mb5-10 | ACH-Mb5-10 | Ba1-10 | Ba4-10 |
| % inhibition | 17 | 15 | 20 | 10 | 10 |

Up regulation of Angiopoietin 2 (Ang2) in ES2 cells with Xanifolia-Y treatment.

The results of study in PCT/US2008/002086, 1188-ALA-PCT, filed Feb. 15, 2008 are incorporated herein by reference.

Data obtained from our Microarray experiments disclose that Xanifolia Y modulates gene expression of the following genes (represented by gene symbol):

Gene Symbol: ABL2, ADAMTS1, AKR1C3, AMIGO2, ANGPT2, ANKRD11, AP2B1, APEH, APLP2, ARL10C, ARMC4, ARMCX1, ARMCX6, ARNTL2, ARNTL2, ATF3, ATP6V0E, ATP6V1B2, ATP6V1C1, ATP6V1C1, BCL2A1, BCL6, BRI3, BTD, C14orf109, C14orf78, C17orf32, C6orf65, C9orf10, C9orf103, CAD, CAV1, CAV2, CBLL1, CCL20, CD33L3, CEBPB, CEP4, CFH, CFHL1, CHRDL1, CITED2, CITED2, CLDN14, CLN8, CLTA, CNAP1, COG6, COL18A1, COL4A2, COL5A1, COL5A2, COL6A3, COPG, CPM, CPNE3, CPSF1, CSRP2BP, CSTB, CTNS, CXCL2, DDB1, DDIT3, DDX20, DKFZP56411171, DKFZP586J0619, DUSP10, DUSP10, DYRK3, EEF2K, EFEMP1, EMP1, EVC, EVI2A, EXT2, FAM62A, FER1L3, FLJ14466, FLNA, FN1, FN1, GANAB, GDF15, GEM, GNPDA1, GPAA1, GPC6, GPNMB, GPNMB, GUSB, H2AFV, H2AFV, HDAC9, HDLBP, HECW2, HMGA2, HMOX1, HSDL2, HSPBAP1, HSPC196, HYOU1, IDS, IGFBP3, IKBKAP, INSIG1,IPO4, IRS2, JAG1, KDELR3, KIAA0251, KIAA0586, KIAA1211, KIAA1462, KIAA1706, KIAA1754, KRT18, KRT7, KRTAP4-7, LAMP2, LEPR, LEPREL1, LHFPL2, LIF, LOC286044, LOC339229, LOC90693, LRRC8E, MAFG, MAGED2, MCTP1, MGC16291, MGC19764, MGC5618, MRPS30, MRPS31, MTERFD3, MYH9, NAGA, NAV2, NCSTN, NEK9, NEU1, NFKBIZ, NMT2, NPC2, NSUN5C, NTNG1, NUP188, OACT2, OS9, P4HA1, P8, PALM2-AKAP2, PALM2-AKAP2, PARVA, PBX2, PDE4DIP, PDIA4, PDIA6, PEG10, PHF19, PIK4CA, PLEKHM1, PLOD1, PLOD2, PPP1R15A, PPP1R15A, PRKDC, PRSS23, PRSS23, PSEN2, PSMD1, PTPRF, PTPRJ, RAB32, RAB9A, RG9MTD1, RGS4, RHOQ, RND3, RNF25, RNPEP, UBE2V1, Kua, Kua-UEV, RNU17D, ROBO4, RRAGC, RRS1, SEC31L1, SERPINB2, SERPINB7, SESN2, SGEF, SGSH, SKIV2L, SLC25A21, SLC35A3, SLC3A2, SMARCA1, SNAPC1, SNF1LK, SPOCD1, SPTAN1, SQSTM1, ST3GAL6, STC2, STX3A, TFPI2, TFPI2, TGFBI, TGM2, THRAP1, TLN1, TMEM60, TNFAIP3, TRIB3, TRIO, TSC2, UAP1L1, UBAP2L, UPP1, URB, USP11, USP5, VDR, WDR4, YTHDF2, ZCCHC9, ZDHHC20, ZFHX1B, ZNF185, ZNF278, ZNF690, ZNF697

Data obtained from our Microarray experiments disclose that Xanifolia Y inhibiting gene expression of the following genes (represented by gene symbol):

AKR1C3, SLC35A3, NEK9, CAV1, USP11, KRT7, TGM2, NCSTN, COG6, WDR4, GPAA1, GUSB, UBAP2L, NMT2, C9orf10, KIAA0251, BTD, EMP1, KRT18, OS9, CPSF1, PSMD1, RNPEP, UBE2V1, Kua, Kua-UEV, NAGA, PARVA, HYOU1, ARMC4, APEH, BTD, FER1L3, CFH, CFHL1, COL5A2, EFEMP1, COL18A1, HSDL2, NUP188, IDS, PLOD1, CPM, SPTAN1, LAMP2, ARNTL2, PLOD2, KDELR3, KIAA0586, SMARCA1, PRSS23, PTPRJ, LEPREL1, H2AFV, CAD, URB, CPNE3, DKFZP586J0619, SERPINB7, CNAP1, EEF2K, IKBKAP, SLC25A21, KDELR3, PDIA6, CAV2, COL4A2, MAGED2, PHF19, OACT2, JAG1, FAM62A, KDELR3, PIK4CA, USP5, ZDHHC20, H2AFV, PTPRF, PEG10, P4HA1, MAGED2, PRSS23, PTPRF, CHRDL1, C6orf65, APLP2, EXT2, COPG, SKIV2L, PDIA4, MYH9, SEC31L1, GANAB, COL5A1, ZNF185, DDB1, HDLBP, AP2B1, TSC2,IPO4, FLNA, TLN1, PRKDC, COL6A3, NTNG1, LEPR, RGS4, FN1, GPC6, LEPR, RGS4, IGFBP3

Data obtained from our Microarray experiments disclose that Xanifolia Y stimulates gene expression of the following genes (represented by gene symbol):

P8, KRTAP4-7, DUSP10, CLDN14, ANGPT2, DUSP10, GDF15, GPNMB, HDAC9, HECW2, C14orf78, UPP1, PPP1R15A, PLEKHM1, STX3A, ANGPT2, SQSTM1, RHOQ, STC2, PPP1R15A, LOC286044, ATF3, HMOX1, CXCL2, CD33L3, LRRC8E, SESN2, LIF, TFPI2, KIAA1706, RRAGC, DDIT3, DYRK3, CTNS, GPNMB, CEBPB, CCL20, AMIGO2, KIAA1462, HSPBAP1, EVC, CLN8, ABL2, SGEF, MCTP1, IRS2, C14orf109, TNFAIP3, RND3, ZFHX1B, LHFPL2, SNF1LK, SLC3A2, NAV2, SPOCD1, TFPI2, EVI2A, ST3GAL6, CSTB, ROBO4, GNPDA1, GEM, IRS2, HMGA2, PALM2-AKAP2, BRI3, KIAA1754, VDR, NEU1, INSIG1, C17orf32, ABL2, PALM2-AKAP2, MTERFD3, ZNF697, NFKBIZ, BCL6, THRAP1, MGC5618, ADAMTS1, MAFG, NPC2, CITED2, TRIB3, ZCCHC9, RNU17D, CITED2, RRS1, NSUN5C, PBX2, RG9MTD1, SGSH, INSIG1, MGC16291, RAB9A, ARMCX6, SERPINB2, ATP6V1B2, DKFZP56411171, ATP6V0E, HSPC196, MRPS30, ARMCX1, LOC339229, ANKRD11, C9orf103, PSEN2, ADAMTS1, SNAPC1, RNF25, ZNF278, TGFBI, UAP1L1, PDE4DIP, MGC19764, TMEM60, CEP4, KIAA1211, DDX20, CSRP2BP, ZNF690, TRIO, CLTA, ATP6V0E, RAB32, MRPS31, LOC90693, ATP6V1C1, CBLL1, YTHDF2, FLJ14466, ARL10C, BCL2A1

Data obtained from our Microarray experiments disclose that Xanifolia YM(ACH-Y) stimulate gene expression of the following genes (represented by gene symbol):

YM stimulate the gene: Gene Symbol CXCL2, CSF2, IL6, NFKBIZ, CXCL3, EGR1, CLDN14, ATF3, IL1A, CSF3, PTGS2, NFKBIZ, KRTAP4-9, TNFAIP3, ABL2, KRTAP4-7, MMP3, DUSP10, FOS, DUSP1, PPP1R15A, DDIT3, DUSP10, HECW2, DSCR1, SESN2, TSLP, SLC7A11, HES1, SESN2, CXCL1, TAGLN3, HBEGF, IER3, RAB2, P8, IL8, GADD45A, LOC441461, GEM, LIF, KLF6, MGC4504, CCL20, PRB1, PRB2, THRA, NR1D1, ERN1, NECAP2, DKK3, GNAO1, NFKBIA, CREB5, CLDN1, CDKN1A, PRDM1, SERPINB2, CD274, FST, LOC401317, BIRC3, PMAIP1, BMP2, IL24, BMP2, WHDC1L2, SGK, RND3, UPP1, C14orf34, ARID1B, KLF6, KLHL24, MAFF, IL12A, SAT, NSD1, JUNB, DUSP1, SLC3A2, ASNS, MAFF, PSAT1, CLTA, ZC3H12C, CLDN1, IL1B, ROBO4, RARA, BCL6, SLC7A11, PDE4DIP, ZNF697, ATP2A2, ZFP36, REST, HDAC9, STAC2, LOC153222, ZC3H12A, SLC25A37, IL17C, TRIB3, CEBPB, PTX3, TRIB3, KIAA1718, ZNF385, TTMP, MGC5618, CSF2, DUSP5, SLC25A25, ADAMTS1, TFRC, SEC15L2, SCNN1A, HES1, LOC153222, C20orf72, ETS1, GDF15, KIAA1754, PACRG, PRSS22, TFRC, AQP2, STX3A, REM1, LIMK2, STC2, ISG20L1, BCL2A1, HES4, TJP3, SLC7A5, CEBPG, LILRB2, LILRB3, LOC389429, LLGL1, KLF6, CSNK1E, DUSP1, ICAM1, PYY2, TPCN1, MFSD2, KIAA0690, SOD2, E2F7, GRIK5, PADI1, HIP1R, IRAK2, EIF1, CEBPG, G0S2, KIAA0690, NEDD4L, MXD1, TXNDC5, PERLDI, HIF1A, RDH13, CTH, ETS2, FAH, CLK4, RIMS4, FLJ12355, LDLR, WARS, IFRD1, LRCH4, SLC1A4, FST, PPIF, ARHGEF2, PMAIP1, PBEF1, C14orf159, ATF4, FLJ90119, TGFBR3, DDX21, MUC8, TNFSF7, SPTLC2, KBTBD8, CIAS1, KIAA0476, NFKB1, DES, FAM48A, ICAM1, INHBA, MARS, C1orf113, GRK6, TCF2, SLC7A1, TNFRSF10B, IER2, TFRC, SOS2, CARS, HAB1, LOC442496, KLHL24, SQSTM1, GIT1, IRS2, SARS, TRIM25, JUN, YRDC, ETS1, CTH, ABL2, CD274, FZD8, EREG, PFDN2, TMEM63B, DYRK3, GARS, RASSF8, CAMTA2, HOXC8, AARS, TBX3, RRAGC, BCAP29, TNFRSF10B, MCL1, PALM2-AKAP2, TMEM22, ZNF548, PCBP2, SLC1A4, FSTL3, TA-PP2C, PIM3, MAFG, NOL1, PEA15, ETS2, IQCG, BEX2, C12orf39, LDLR, VEGF, CCNL1, LOC440069, SNAPC1, SLC27A5, MARS, ICAM1, AXUD1, KCNIP2, LOC146177, FLJ40941, GOT1, C11orf17, NUAK2, TTBK1, SNCA, NFRKB, GRB2, ADAMTS1, PALM2-AKAP2, CCNL1, JUN, SPRY4, SLC38A1, E2F7, MGC27165, IDS, SLC7A1, FLJ11021, KCNK5, GYPC, MYC, CACNG6, PHLDA1, INSIG1, FLJ13448, LOC202051, GALNT10, TFEB, ABL2, MTHFD2, SERPINB8, TNPO2, MCF2L, SERTAD1, SPRY2, PHLDA1, SLC7A11, CXCL5, COMT, GTPBP2, RAB4B, ATXN7, OTUD5, VEGF, ADAMTS6, YARS, NAV3, SAMD4, C17orf32, SHMT2, CHIC2, ORAOV1, CREM, ALS2CL, AMIGO2, MGC19764, SFPQ, MGC11257, PLEKHMI, MMP28, SLC4A5, DNAJB9, ERRFI1, FZD8, MGC4399, GUCA1B, ATP13A3, KIAA0020, XBP1, ATP6VI B2, IGLV3-25, CHD4, GRB10, FLJ40089, CLDN19, NPC1, RIPK2, PLEKHF2, LOC283314, RSPO3, GSK3A, ANKRD11, WARS, GNPDA1, IGKC, IGKV1-5, RCL1, C9orf91, TIMM10, SLC1A4, ODC1, SLC38A1, EIF4EBP1, ZNF267, YRDC, CHD4, PER1, NFKBIE, INSIG1, FLJ11259, NCOA3, TNPO2, BAZ2A, SLC1A5, KRTAP2-1, PDE4D1P, EPB41 L3, CITED2, JTV1, TA-PP2C, METRNL, BCL10, C1orf19, PTP4A1, PDE4DIP, CPSF1, TIMM10, IGSF21, TM4SF1, CDK6, BANP, PHLDA1, PAPPA2, MGC17337, TNFRSF19L, ADAMTS10, CBFB, HERPUD1, RTTN, FLJ13855, SYNPO, NAV2, FLJ34208, DDX10, C6orf66, L0056902, CHMP1B, HIPK2, H3F3B, NAV3, ELL2, NSUN5C, PLAUR, UCK2, PBEF1, TP53BP2, TEX10, B3GNT5, USP36, INHBA, SPIRE1, CSTB, NSUN5C, TFPI2, Our experiment disclosed that Xanifolia Y and ACH-Y inhibited genes expression of the following genes: FN1, ITGAV, LAMA4, LAMB2, LAMC1, LAMB1, LAMB1, LAMA4, LAMA5, LAMC1, LAMA2, LAMB1, LAMA3, SCAMP1, TICAM2, SCAMP1, TICAM2, SCAMP1, SCAMP1, CAMK2B, DL1, ICAM3, CEECAM1, ICAM5, SCAMP1, CAMK1G, CAMSAP1, MCAM, CAMTA1, CKN1, ALCAM, DCAMKL2, CEACAM3, CAMK2D, CAMK2B, SCAMP5, CAMK4, NCAM1, CAMK2G, MYH9, MYH10, MYO1D, MYO5A, MYLK, MYO6, MYO5A, MYO1C, MYLK, MYO6, MYLC2PL, MYO10, MYO6, TPM3, MYO1C, BECN1, MYO1E, TPM3, M-RIP, MYO1B, MYO10, MYO5A, M-RIP, MYO10, MYL6, MYOHD1, BECN1, TPM4, MYLK, MYH10, MYOHD1, LOC221875, LOC402643, MYO15B, LOC129285, MYH11, MYO1B, MYO1C, MYO9B, CDH13, CTNNAL1, CDH13, CDH12, CTNNB1, CDH5, CTNND1, CDH2, CTNNA1, CDH2, PCDHB16, CTNNA1, CELSR2, PCDHB6, PCDHB7, CTNND2, PCDHGC3, PCDHGB4, PCDHGA8, PCDHGA12, PCDHGC5, PCDHGC4, PCDHGB7, PCDHGB6, PCDHGB5, PCDHGB3, PCDHGB2, PCDHGB1, PCDHGA11, PCDHGA10, PCDHGA9, PCDHGA7, PCDHGA6, PCDHGA5, PCDHGA4, PCDHGA3, PCDHGA2, PCDHGA1, CTNND1, CDH23, PCDHB12, PCDHB10, PCDH18, CDH20, PCDH9, PCDHGA12, PCDHGA11, PCDHGA10, PCDHGA6, PCDHGA5, PCDHGA3, PCDH7, CDH18, CDH6, CCBE1, COL10A1, COL12A1, COL13A1, COL18A1, COL1A1, COL21A1, COL4A1, COL4A2, COL4A5, COL4A6, COL5A1, COL5A2, COL6A1, COL6A2, COL6A3, COL9A1, MMP9, P4HA1, P4HA2, P4HB, PCOLCE, PCOLCE2, PCOTH, PLOD1, PLOD2, PLOD3, CIB1, ILK, ITGA2, ITGA3, ITGA4, ITGA6, ITGAV, ITGB1, ITGB1BP1, ITGB2, ITGB5, ITGBL1, TNC, EMILIN1, ICAM1, HSPG2, HPSE, HS2ST1, SDC2, Determination of gene expression by Real-time PCR method (Brilliant QPCR, Agilent Technologies): The real-time polymerase chain reactions further confirm the results obtained from micro array analysis. The Real-time PCR results (shown below) confirmed that Compound Y3 and YM increase the expression of the genes: ANGPT2, DDIT3, LIF and NFKB1Z

TABLE 19

| % of control | ANGPT2 | DDIT3 | LIF | NFKB1Z |
|---|---|---|---|---|
| Control | 100 | 100 | 100 | 100 |
| Y3 | 300 | 213 | 163 | 142.9 |
| YM | 216 | 660 | 447 | 784.8 |

D = DMSO control
Y = Y3
YM = Y3 without sugar

TABLE 20

The experimental results confirmed that compound Y3 inhibit the gene expression of adhesion proteins: ITGAV, TNC, COL1A1, FN1 and LAMA4

| % of control | ITGAV | TNC | COL1A1 | FN1 | LAMA4 |
|---|---|---|---|---|---|
| Control | 100 | 100 | 100 | 100 | 100 |
| Y3 | 63.8 | 41.1 | 49.9 | 44.1 | 53.6 |

With the same method, we also confirmed that the compound YM inhibits the expression of adhesion proteins COL1A1, FN1 and LAMA4

TABLE 21

| % of control | COL1A1 | FN1 | LAMA4 |
|---|---|---|---|
| Control | 100 | 100 | 100 |
| YM | 42 | 72.8 | 81 |

ANGPT2 = angiopoietin 2,
ITGAV = inttegrin alpha V,
TNC = Tenascin C,
COL1A1 = collagen type 1 alpha 1,
FN1 = fibronectin 1,
LAMA4 = lamin alpha 4,
LIF = Leukemia inhibitory factor (cholinergic differentiation factor),
NFKB1Z = nuclear factor of kappa light polypeptide gene enhancer in B-cells inhibitor, zeta ANGPT2= angiopoietin 2, LIF= Leukemia inhibitory factor ITGAV= integrin alpha V, (cholinergic differentiation factor), TNC= Tenascin C, NFKB1Z= nuclear factor of kappa light COL1A1= collagen type 1 alpha 1, polypeptide gene enhancer in B-cells
FN1= fibronectin 1, inhibitor zeta
LAMA4= laminin alpha 4
DDIT3= DNA-damage-inducible transcript 3, Data obtained from our Microarray experiments disclose that Xanifolia Y modulates gene expression. This invention provides compositions and methods for modulating the gene expression in cancer cells, wherein the modulating comprises of positive and negative regulation, wherein genes being modulated are adhesion proteins; wherein modulation includes expression, production and secretion of adhesion proteins, wherein the adhesion proteins comprise fibronectin, integrins family, Myosin, vitronectin, collagen, laminin, cadherin, heparin, Glypican, tenascin, CD 54, CAM. This invention provides compositions and methods for modulating angiopoietins, wherein comprises positive regulating the angiopoietin 2, wherein comprises negative regulating angiopoietin 1. The composition and method of this invention comprises a triterpene wherein acylated group at carbon position 21 and/or 22 of the triterpene is necessary for the function and are selected from angeloyl, acetyl, alkanoyl, and alkenoyl and acyl group. The sugar moiety (ies) at position 5 of the triterpene is important for enhancing activity of these compounds.

Leptin is a promoter in breast cancer cells. The Xanifolia Y and YM inhibit the expression of leptin.

The thrombospondins are a family of multifunctional proteins. The family includes thrombospondins 1-5. Thrombospondin-1 TSP1 is a multifunctional, matricellular glycoprotein, containing interacting domains for a large variety of adhesion, migration and proliferation, angiogenesis and tumor cell metastasis.

The insulin-like growth factor binding protein (IGFBP) is a multifunctional protein that relate to metastasis, tumor growth and angiogenesis. Compounds in this application modulate gene expression of RAB3B, inhibiting metastasis, tumor growth and angiogenesis.

The activation of cell migration and cancer cells metastasis requires the sensitive of potassium channel. The results of the micro array experiment showed that compound Y and YM inhibit gene expression of family protein relate to potassium channel in ES2 cells.

RAB3B is member RAS oncogene family protein. Compounds in this application modulate gene expression of RAB3B, inhibiting metastasis, tumor growth and angiogenesis.

In mild conditions, the saponin can be partially hydrolyzed into a mixture of products which are separated by HPLC. Specific partial hydrolysis of saponins can also be achieved with enzymes. The glycosidases catalyze the hydrolysis of the glycosidic linkage. Galactosidase is an enzyme which catalyzes the hydrolysis of galactosides. The glucosidase is an enzyme which breaks glucose from saponin. Other enzyme examples are xylanases, lactase, amylase, chitinase, sucrase, maltase, and neuraminidase.

The sugar moiety of the triterpenoid saponin (example Xanifolia Y) can be removed by acid hydrolysis. The synthetic compound of ACH-Y is obtained. The ACH-Y is a triterpene with acyl groups but no sugar moiety. The acyl group of the saponin (example Xanifolia Y) can be removed by alkaline hydrolysis. A synthetic compound of AKOH-Y can be obtained. The AKOH-Y is a pentacyclic triterpene with sugar moieties. A pentacyclic triterpene can be obtained by acid and alkaline hydrolysis of saponin from natural source. A pentacyclic triterpene also can be obtained by other methods (Reference: Surendra et al., Rapid and Enantioselective Synthetic Approches to Germanicol and Other Pentacyclic Triterpenes). The pentacyclic triterpene with sugar moieties can also be obtained with synthesis (Reference: Ple et al., Synthesis of L-arabinopyranose containing hederagenin saponins). Acylation is the process of adding an acyl group to a compound. Friedel-Crafts reaction is an example of the process. An active compound can be obtained by acylating a pentacyclic triterpene. In an embodiment, acylating C21 and C22 of a pentacyclic triterpene gives an anticancer compound. In an embodiment, sugar moiety(s) at C3 can increase the activities of pentacyclic triterpene, wherein the triterpene has acyl group(s), wherein the acyl group(s) may be at C21, 22, or 28. In an embodiment, a sugar moiety is at C21, 22, or 28, wherein the sugar moiety is substituted with 2 acyl groups. Reference in PCT/US/US05/319000, WO20061029221, filed Sep. 7, 2005, U.S. Ser. No. 11/289, 142 filed Nov. 28, 2005)

Determination of cell growth of Leishmania parasites by MTT assay shows that Y10 is cytotoxic to Leishmania Major (promastigotes) with IC50 of 15 ug/ml. IC50 of Y is 15 ug/ml, Y0 is 25 ug/ml, Y1 is 23 ug/ml, Y5 is 16 ug/ml, Y7 is 18 ug/ml, ACH-Y Is 30 ug/ml, Mb5 is 15 ug/ml, ACH-Mb5 is 18 ug/ml, Z12 is 23 ug/ml, and Ba1 is 15 ug/ml. AKOH-Y and AKOH-Mb5 are not cytotoxic to Leishmania Major (promastigotes).

The invention will be better understood by reference to the Experimental Details which follow, but those skilled in the art will readily appreciate that the specific experiments detailed are only illustrative, and are not meant to limit the invention as described herein, which is defined by the claims which follow thereafter.

Throughout this application, various references or publications are cited. Disclosures of these references or publications in their entireties are hereby incorporated by reference into this application in order to more fully describe the state of the art to which this invention pertains. It is to be noted that the transitional term "comprising", which is synonymous with "including", "containing" or "characterized by", is inclusive or open-ended and does not exclude additional, un-recited elements or method steps.

EXPERIMENTAL DETAILS

Experiment details of herb extraction, analysis of extract components by HPLC, determination of the cell-growth activity effected by Xanifolia Y with cells derived from different human organs using MTT Assay, purification of the bioactive components from plant extract, fractionation of plant extracts with FPLC, isolation of component Ys with preparative HPLC, determination of the chemical structure, cell experiments and animal studying are disclosed in PCT/US05/31900, U.S. Ser. No. 11/289,142, U.S. Serial 10/906,303, U.S. Ser. No. 11/131,551 and U.S. Ser. Nos. 11/683,198, filed on Mar. 7, 2007, PCT/US2007/077273, filed Aug. 30, 2007, U.S. Ser. No. 60/890,380, filed on Feb. 16, 2007, U.S. Nos. 60/947,705, filed on Jul. 3, 2007, PCT/US2008/002086, 1188-ALA-PCT, filed Feb. 15, 2008, the contents of which are incorporated herein by reference. Experiments 1-23 of PCT/US2008/002086, 1188-ALA-PCT, filed Feb. 15, 2008 are incorporated herein by reference.

Experiment 1

Removal of the Sugar Moiety from Saponin by Acid Hydrolysis

Method: 15 mg saponin was dissolved in 1 ml of Methanol. 1 ml of 2N HCl was then added. The mixture was refluxed in 80° C. water bath for 5 hours. The solution was then neutralized by adding 2 ml of 1N NaOH (to final pH 4-6). The aglycone was then extracted with ethylacetate 3 ml×2. The extracts were collected and pooled. Further isolation of aglycone (sugar-removed saponin) was achieved by HPLC with isocratic elution of 80-100% acetonitrile.

Experiment 2

Removal of the Acyl Group by Alkaline Hydrolysis

Method: 20 mg of saponin was dissolved in 0.5 ml of 1M NaOH. The solution was incubated in 80° C. water bath for 4 hours. It was cooled to room temperature before neutralized with 0.5 ml 1 N HCl (adjust pH to about 3). The mixture was extracted with 2 ml 1-butanol 3 times. The butanol fractions were collected and lyophilized. The hydrolyzed saponin with further purified with HPLC in a C-18 column eluted with 25% acetonitrile.

Experiment 3

Analysis of Genesis of Blood Vessel in Xenograft Tumor Treated with Compound Y

Method: Athymic Nu/Nu mice (5-6 weeks old) are divided into two groups (1 and 2) with 5 animals in each group. On day 0, all mice were transplanted intra-peritoneally with one million ES2 (human ovarian cancer) cells. Animals were randomly divided into two groups:

Group 1: Control group. Animals did not receive drug-treatment.

Group 2: Drug-treatment group. On days 10-15 and 18-22, animals received daily drug administration of Xanifolia-Y, by i.p. route at dosage of 2.5 mg/kg.

Results: Animals showed high tumor burden after 18 days. Animals with high tumor burden were euthanized and solid tumors were taken out from these mice (between 18-27 days). Tumor tissues fixed with formalin at room temperature. The fixed tissues were sectioned and stained with Haematoxylin and eosin (H&E). The red blood cells inside the micro blood vessels were identified under a microscope. FIG. 1 shows that more blood vessels were observed in the control Group1 than those in the drug-treated Group 2

Experiment 4

Determination of Cell Growth of *Leishmania* Parasites by MTT Assay

Method: *Leishmania* parasites (*Leishmania major*: MRHO/SU/59/P/LV39) were grown in culture medium in a T75 flask at room temperature. Promastigotes of *Leishmania major* (approximately 40 million per ml) were used in the experiment. 1.2 ml cell culture was transferred to a well of the 24-wells plate. Saponin Y10 (0.2 ml in medium) with different concentrations (final 6.25-200 ug/ml) was added to culture and cells were grown for 1-5 days at room temperature. At the end of drug-treatment, 150 ul of MTT (5 mg/ml in PBS) was added to each well and incubated for 4 hours. Formazan formed in cells was dissolved with DMSO and the OD at 490 nm was determined by an ELISA reader.

Results: this experiment shows that Y10 is cytotoxic to *Leishmania Major* (promastigotes) with IC50 approximately equal to 15 ug/ml. Experiments are repeated with Y, ACH-Y, AKOH-Y, Mb5, ACH-Mb5, AKOH-Mb5 and Ba1.

Experiment 5

Adding the Acyl Group to Triterpene by Esterification

Method: 40 mg of triterpene core (fraction IV) was dissolved in 1 ml pyridine in a 50 ml tube. Reaction is started by adding 0.2 ml of acyl chloride (including Tigloyl chloride, angeloyl chloride or benzoyl chloride). The mixture is stirred for 3 days at room temperature. At the end of reaction, 3 ml of NaHCO3 is slowly added to the reaction mixture. The solution is then extracted 3 times with 10 ml of ethyl acetate which is then evaporated under vacuum and at 45 C and lyophilization. The active esterification products are purified with HPLC.

Experiment 6

Adding the Acyl Group to Triterpene by Esterification

Method: 40 mg of triterpene core (fraction IV) was dissolved in 1 ml pyridine in a 50 ml tube. Reaction is started by adding 0.2 ml of acyl chloride (including Tigloyl chloride, angeloyl chloride or benzoyl chloride). The mixture is stirred for 0.5 hr, 1 hr, 2 hrs, 3 hrs, 4 hrs, 8 hrs or 1 day at room temperature. At the end of reaction, 3 ml of NaHCO3 is slowly added to the reaction mixture. The solution is then extracted 3 times with 10 ml of ethyl acetate which is then evaporated under vacuum and at 45 C and lyophilization. The active esterification products are purified with HPLC.

What is claimed is:

1. A method for treating parasites in a subject, comprising contacting said subject with an effective amount of compound, or its salt, or ester thereof,
wherein the parasitics comprise leishmaniases, amoebiasis, trypanosomiasis, toxoplasmosis or malaria; wherein the compound is selected from the following: a) A compound having structure Xanifolia(Y),

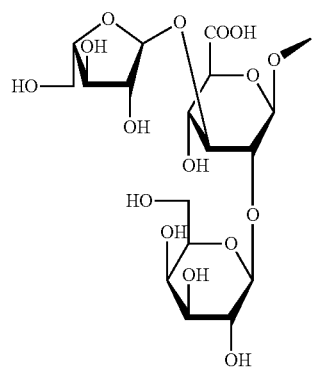

Y₃ or chemical name: 3-O-[β-D-galactopyranosyl (1→2)]-α-L-arabinofuranosy (1→3)-β-D-glucuronopyranosyl-21,22-O-diangeloyl-3β, 15α, 16α, 21 β, 22α, 28-hexahydroxyolean-12-ene;

b) A compound having structure Xanifolia (Y1),

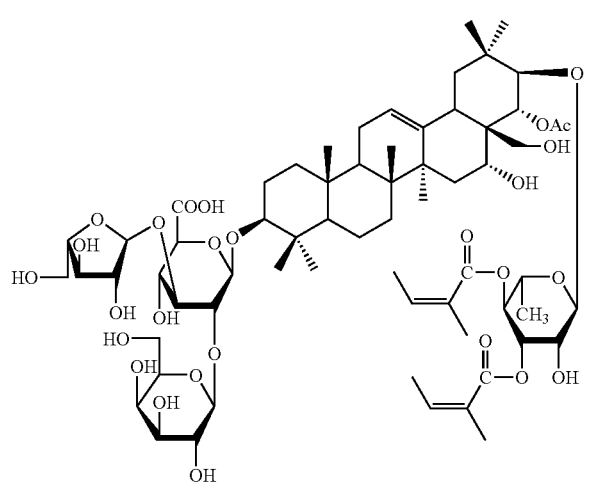

Y₁ or chemical name: 3-O-[β-D-galactopyranosyl (1→2)]-α-L-arabinofuranosyl (1→3)-β-D-glucuronopyranosyl-21-O-(3,4-diangeloyl)-α-L-rhamnophyranosyl-22-O-acetyl-3β,16α, 21β, 22α, 28-pentahydroxyolean-12-ene;

c) A compound having structure Xanifolia (Y2),

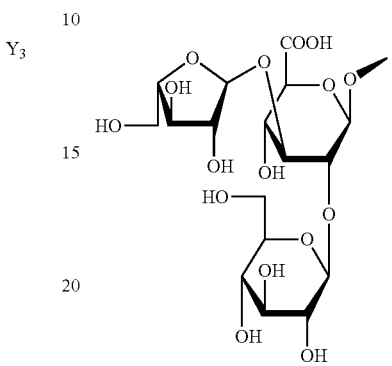

Y₂

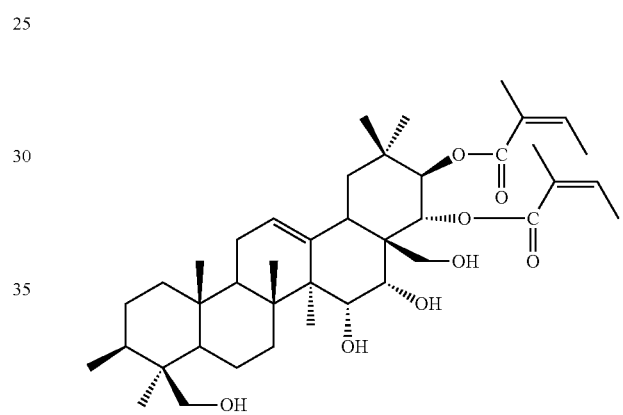

or chemical name: 3-O-[β-D-glucopyranosyl-(1→2)]- α-L-arabinofuranosy (1→3) -β-D-glucuronopyranosyl-21, 22-O-diangeloyl-3β, 15α, 16α, 21β, 22α, 24β, 28-heptahydroxyolean-12-ene;

d) A compound having structure Xanifolia (Y8),

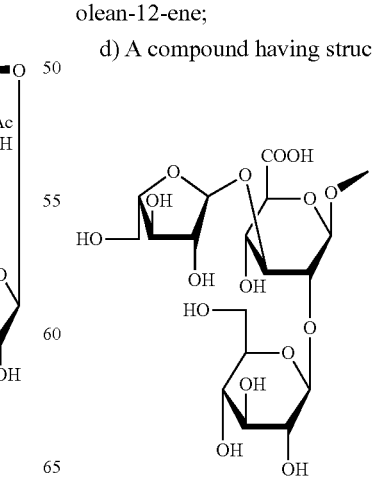

Y-8

75

-continued

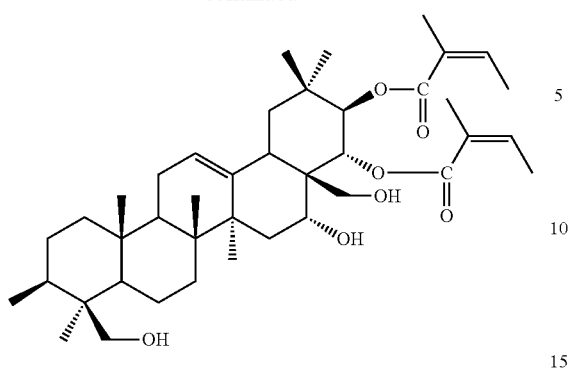

or chemical name: 3-O- [β-glucopyranosyl (1→2) ]-α-arabinofuranosyl (1→3) -β-glucuronopyranosyl-21, 22-O-diangeloyl-3β, 16α, 21β, 22 α, 24β, 28-hexahydroxyolean-12-ene;

e) A compound having structure Xanifolia (Y9),

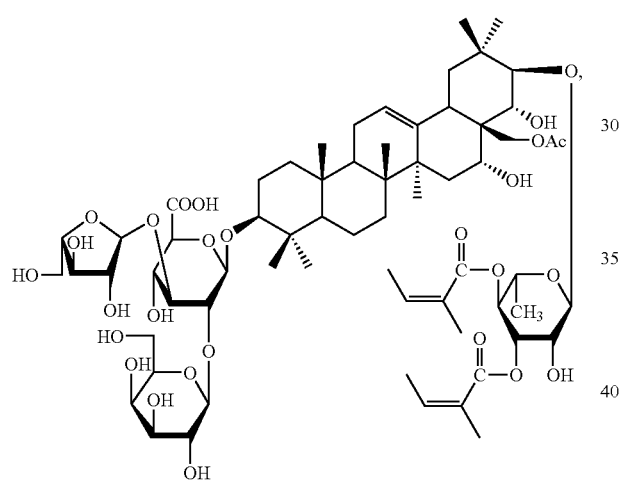

Y9 or chemical name: 3-O-[β-galactopyranosyl (1→2) ]-α-arabinofuranosyl (1→3) -β-glucuronopyranosyl-21-O- (3, 4-diangeloyl) -α-rhamnopyranosyl-28-O-acetyl-3β, 16α, 21β, 22α, 28-pentahydroxyolean-12-ene; and f) A compound having structure Xanifolia (Y10),

Y-10

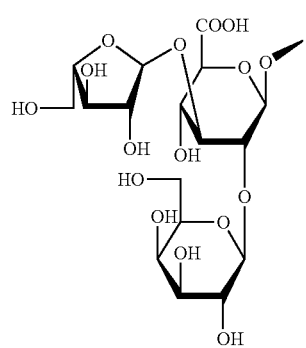

76

-continued

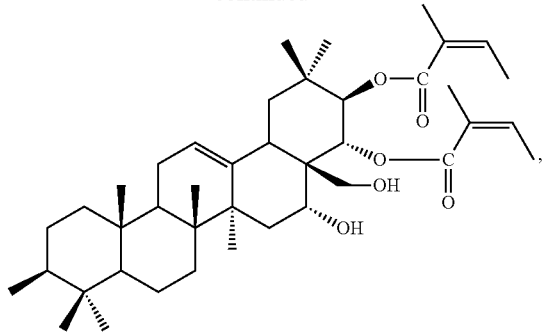

or chemical name:

3-O- [β-galactopyranosyl (1→2) ]-α-arabinofuranosyl (1→3) -β-glucuronopyranosyl-21, 22-O-diangeloyl-3 β, 16α, 21 β, 22α, 28-pentahydroxyolean-12-ene, g) A compound having structure Xanifolia (Y0),

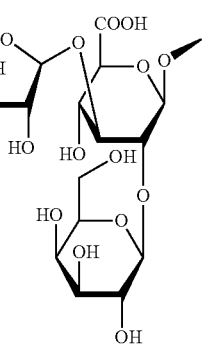

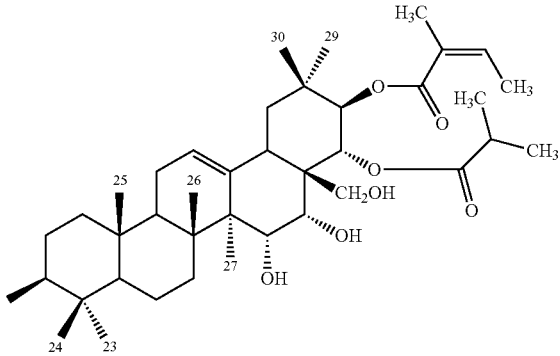

or chemical name: 3-O-[β-D-galactopyranosyl(1→2)]-α-L-arabinofuranosyl(1→3)-β-D-glucuronopyranosyl-21-O-angeloyl, 22-O-(2-methylpropanoyl)-3β, 15α, 16α, 21β, 22α, 28-hexahydroxyolean-12-ene, h) A compound having structure Xanifolia (X),

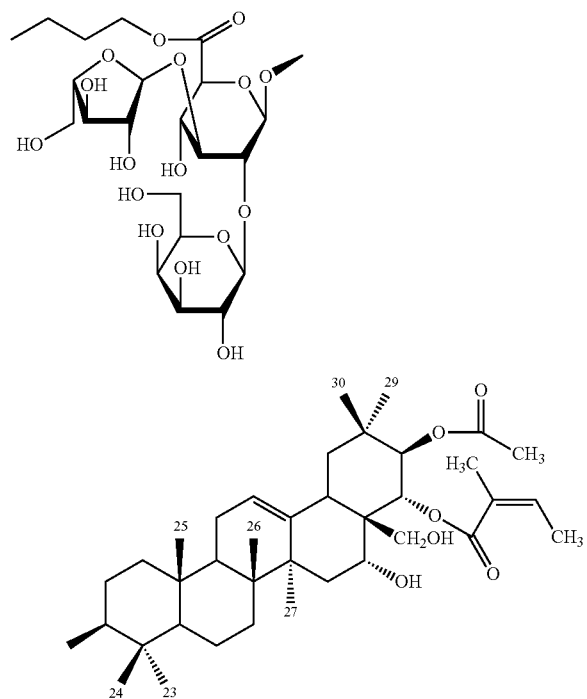

or chemical name: 3-O-{[β-galactopyranosyl (1→2)]-[α-L-arabinofuranosyl (1→3)]-β-D-glucuronopyranoside butyl ester}-21-O-acetyl-22-O-angeloyl-3β,16 α,21β,22α,28-pentahydroxyolean-12-ene, i) A compound having structure (Y7),

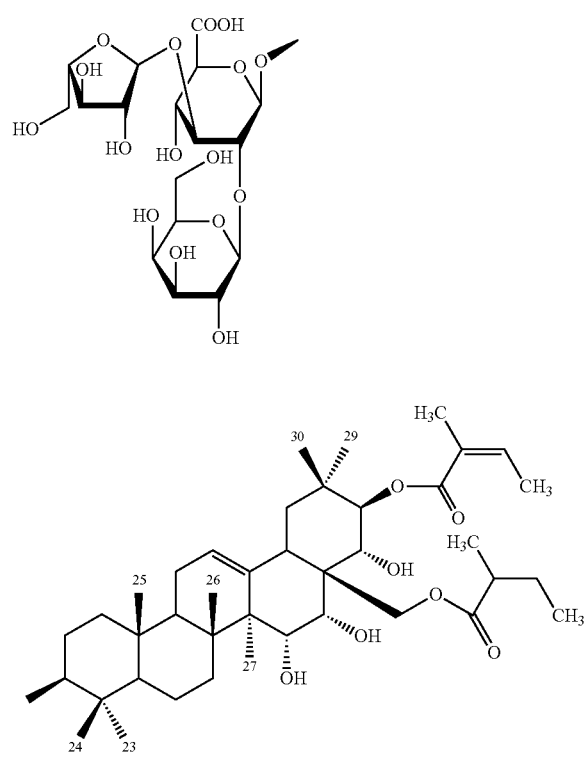

or chemical name: 3-O-[O-D-galactopyranosyl-(1→2)]-α-L-arabinofuranosyl-(1→3)-β-D-glucuronopyranosyl-21-O-angeloyl-28-O-2-methylbutanoyl-3β, 15 α, 16α, 21β, 22α, 28-hexahydroxyolean-12-ene;

j) A compound having structure (ACH-Y): k) A compound having structure:

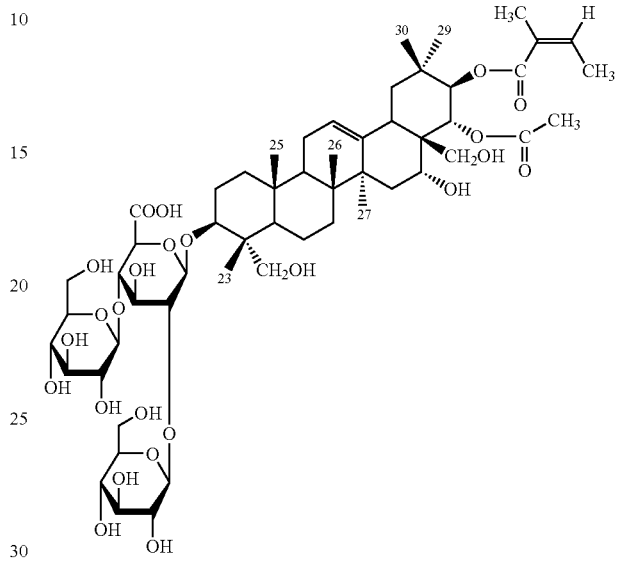

or chemical name:

3-O- [β-glucopyranosyl (1→2) ]-β-arabinofuranosyl (1→4) -β-glucuronopyranosyl-21-O-angeloyl-22-O-acteyl-3β, 16 α, 21β, 22α, 24β, 28-hexahydroxyolean-12-ene;

l) A compound having structure (Y5):

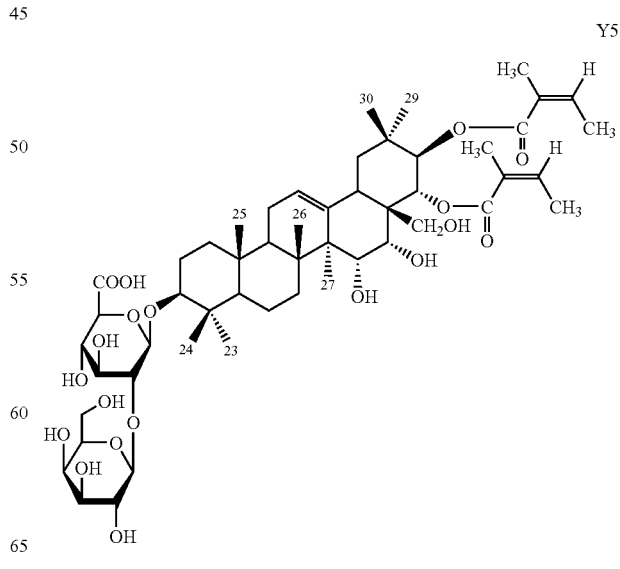

m) A compound having structure:
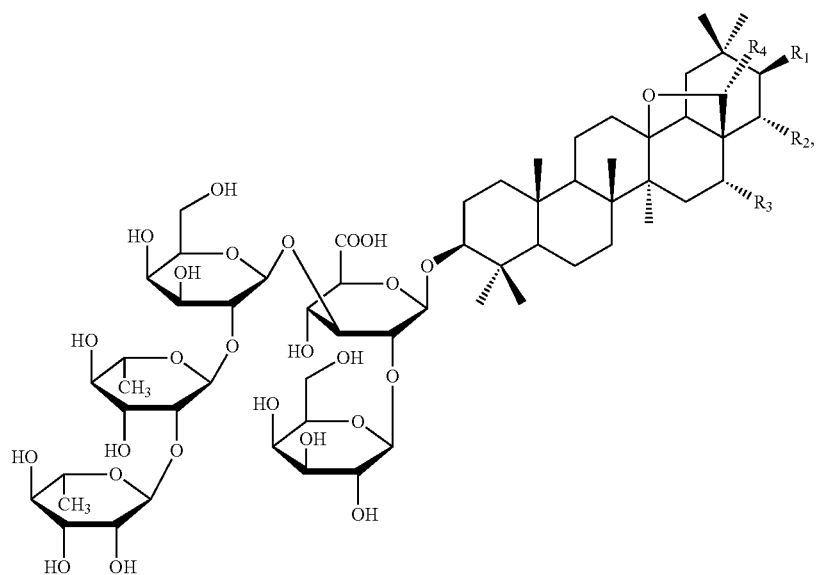
wherein R1 and R2 are O(C=O)C(CH3)=CH(CH3), R3 is OH, and R4 is OH;
(n) A compound having structure (ACH-Mb5):
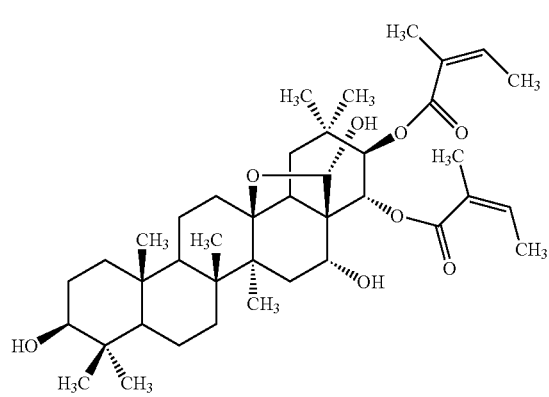
ACH-Mb5
(o) A compound having structure (Ba 1):
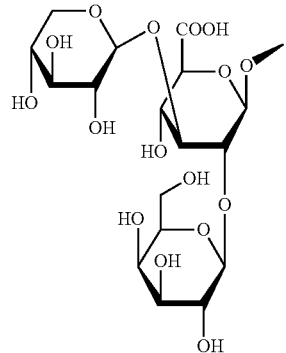
-continued
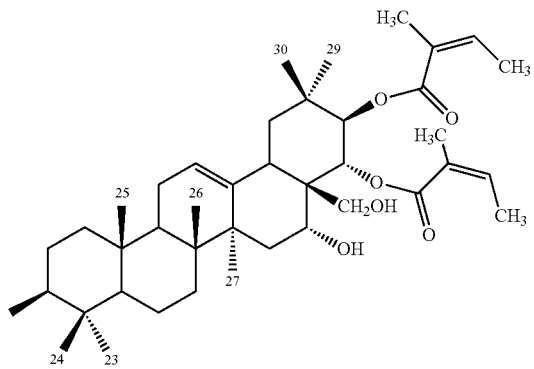
3-O-[β-D-galactopyranosyl(1→2)]-β- D-xylopyranosyl (1→3)-β-D-glucuronopyranosyl-21-O-angeloyl, 22-O-angeloyl-3β, 15α, 21β, 22α, 28-pentahydroxyolean-12-ene, named Ba 1; and
(p) A compound having structure (Z12):
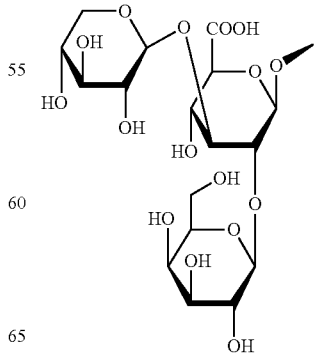
Z12

-continued

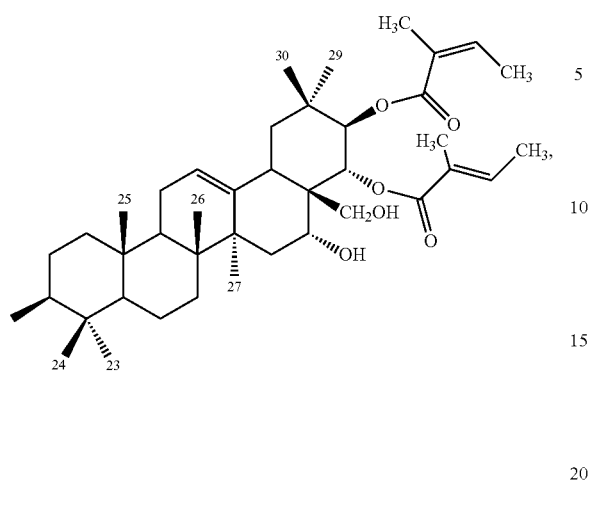

3-O-[β-D-galactopyranosyl(1→2)]-β-D-xylopyranosyl (1→3)-β-D-glucuronopyranosyl-21-O-angeloyl, 22-O-tigloyl-3β, 16α, 21β, 22α, 28-pentahydroxyolean-12-ene.

2. The method of claim 1, wherein the antiparasitics comprise inhibiting leishmaniases, amoebiasis, trypanosomiasis, toxoplasmosis or malaria.

3. The method of claim 1, wherein the compound is selected from the following:
a) A compound having structure:

wherein R1 and R2 are O(C=O)C(CH3)=CH(CH3), R3 is OH, and R4 is OH; and (b) A compound having structure (ACH-Mb5):

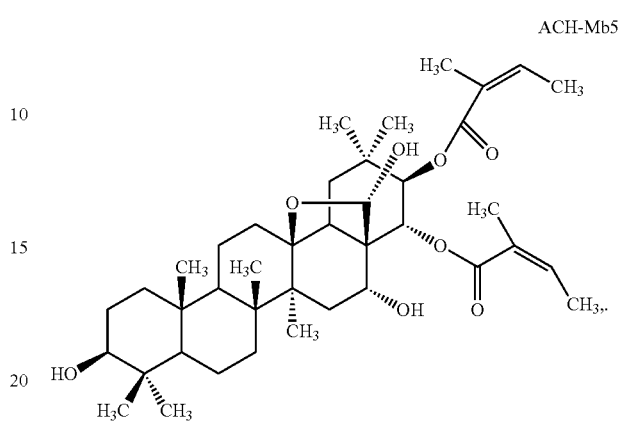

ACH-Mb5

4. A pharmaceutical composition for modulating the secretion or expression of adhesion protein of cells, modulating the gene expression, wherein the composition comprises a pharmaceutically acceptable excipient and a compound selected from the following:

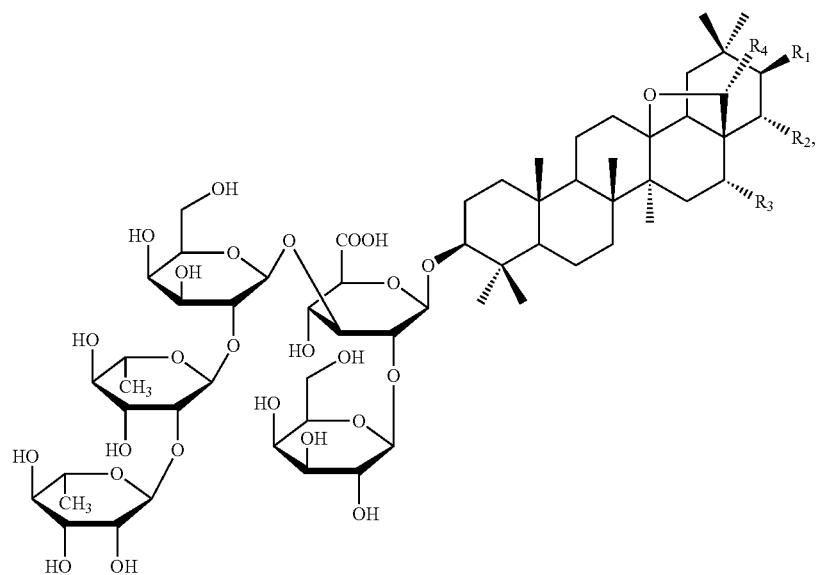

(a) A compound having the structure:

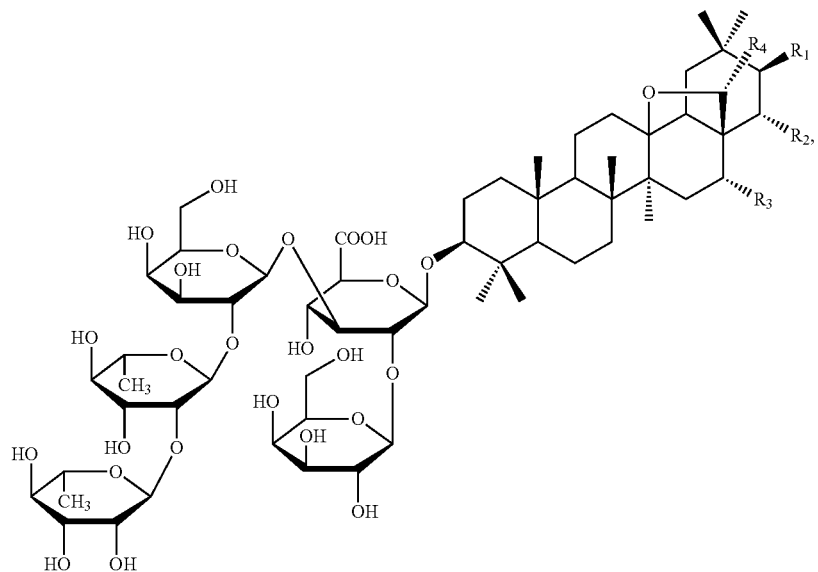

wherein R1 and R2 are O(C=O)C(CH3)=CH(CH3), R3 is OH, and R4 is OH; and (b) A compound having structure:

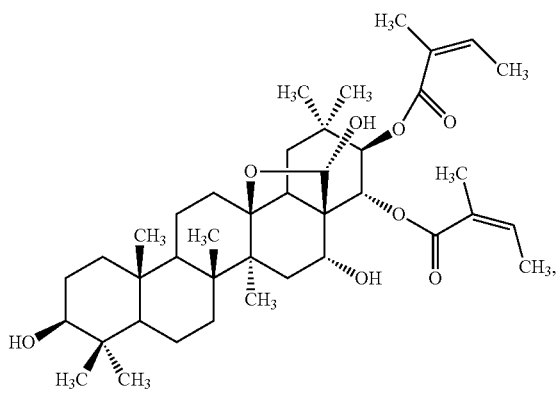

Also named as ACH-Mb5.

5. The pharmaceutical composition of claim 4, wherein the modulating secretion or expression of adhesion of a cell comprises inhibiting the secretion or expression of adhesion protein, wherein the adhesion proteins comprise fibronectin, integrins family, Myosin, vitronectin, collagen, laminin, polyglycans, cadherin, heparin, tenascin, CD 54and CAM; wherein the inhibiting protein expressed from genes, including ITGAV, TNC, COLIAI, FNI, LAMA4, family protein relate to potassium channel, RAB3B, thrombospondin, insulin-like growth factor, G-protein and Glypican.

6. The pharmaceutical composition of claim 4, wherein the modulating the secretion or expression of adhesion protein comprises reducing the secretion or expression of fibronectin for inhibiting the metastasis or growth of cancer cells, wherein the cancer is selected from breast, leukocyte, liver, ovarian, bladder, prostate, skin, bone, brain, leukemia, lung, colon, CNS, melanoma, renal, cervix, esophagus, testis, spleen, kidney, lymph, pancreas, stomach and thyroid cancer.

7. The pharmaceutical composition of claim 4, wherein the angiopoietin comprises angiopoietin 1, angiopoietin 2, angiopoietin 3, angiopoietin 4, angiopoietin 5, angiopoietin 6, angiopoietin 7, angiopoietin-like 1, angiopoietin-like 2, angiopoietin -like 3, angiopoietin-like 4, angiopoietin-like 5, angiopoietin-like 6 and angiopoietin-like 7; wherein the modulating comprises positive and negative regulating; wherein modulating secretion or expression of angiopoietin comprises stimulating secretion or expression of the angiopoietin 2in order to inhibit angiogenesis; or wherein modulating angiopoietin comprises inhibiting secretion or expression of the angiopoietin 1 in order to inhibit angiogenesis; or wherein modulating secretion or expression of angiopoietin comprises inhibiting secretion or expression of the angiopoietin-like 1; or wherein modulating secretion or expression of angiopoietin comprises inhibiting the secretion or expression of angiopoietin-like 4.

8. The pharmaceutical composition of claim 4, wherein the modulating gene expression includes increasing the expression of the protein phosphatase 1, dual specificity phosphatase 10; or increasing expression of the genes of ANGPT2, DDIT3, LIF and NFKB1Z.

9. A pharmaceutical composition comprising a compound is selected from the following:
(a) A compound having structure:
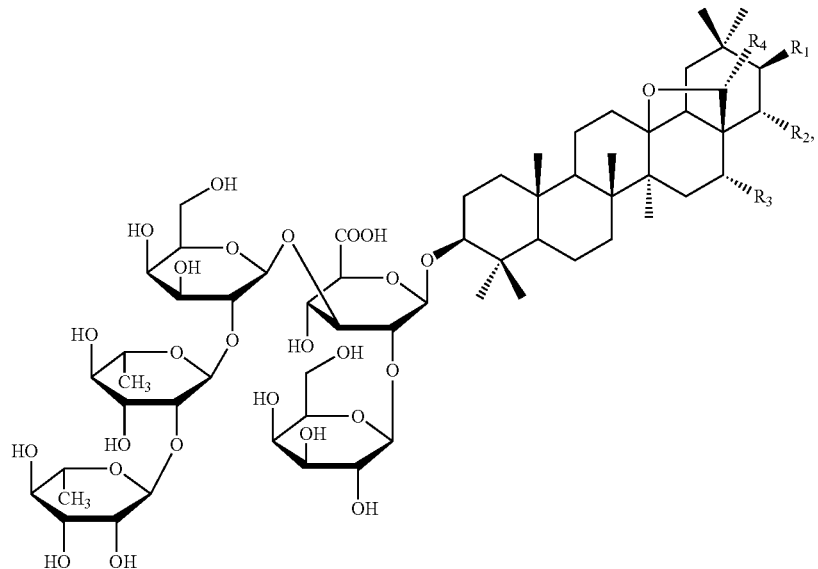
wherein R1 and R2 are O(C=O)C(CH3)=CH(CH3), R3 is OH, and R4 is OH; and
(b) A compound having structure:
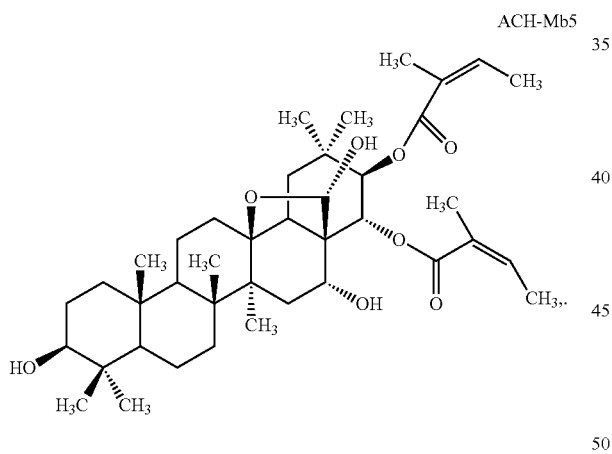
ACH-Mb5
also named ACH-Mb5.
10. The pharmaceutical composition of claim 9 wherein the compound is administered with a pharmaceutically acceptable carrier or diluent.
* * * * *